(12) United States Patent
Rudolf et al.

(10) Patent No.: US 7,439,237 B2
(45) Date of Patent: Oct. 21, 2008

(54) SELECTED CGRP-ANTAGONISTS, PROCESS FOR PREPARING THEM AND THEIR USE AS PHARMACEUTICAL COMPOSITIONS

(75) Inventors: Klaus Rudolf, Warthausen (DE); Stephan Georg Mueller, Warthausen (DE); Philipp Lustenberger, Basel (CH); Dirk Stenkamp, Biberach (DE); Gerhard Schaenzle, Biberach (DE); Kirsten Arndt, Biberach (DE); Henri Doods, Warthausen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/688,123

(22) Filed: Mar. 19, 2007

(65) Prior Publication Data

US 2007/0238715 A1  Oct. 11, 2007

Related U.S. Application Data

(63) Continuation of application No. 11/107,195, filed on Apr. 15, 2005, now abandoned.

(51) Int. Cl.
C07D 401/14 (2006.01)
A61K 31/4545 (2006.01)
A61P 25/06 (2006.01)

(52) U.S. Cl. ...................... 514/221; 540/500
(58) Field of Classification Search ............... 540/500; 514/221
See application file for complete search history.

(56) References Cited

U.S. PATENT DOCUMENTS

| | | |
|---|---|---|
| 6,344,449 B1 | 2/2002 | Rudolf et al. |
| 6,521,609 B1 | 2/2003 | Doods et al. |
| 2004/0076587 A1 | 4/2004 | Kruss et al. |
| 2004/0132716 A1 | 7/2004 | Rudolf et al. |
| 2004/0192729 A1 | 9/2004 | Rudolf et al. |
| 2005/0147568 A1 | 7/2005 | Trunk et al. |
| 2005/0234067 A1 | 10/2005 | Mueller et al. |
| 2005/0250763 A1 | 11/2005 | Mueller et al. |
| 2006/0079504 A1* | 4/2006 | Rudolf et al. .......... 514/217.04 |
| 2006/0252750 A1 | 11/2006 | Mueller et al. |

FOREIGN PATENT DOCUMENTS

| | | |
|---|---|---|
| AU | 2003276156 A1 | 5/2004 |
| CA | 2387613 A1 | 5/2001 |
| CA | 2503455 A1 | 5/2004 |
| WO | 9811128 | 3/1998 |
| WO | 0018764 | 4/2000 |
| WO | 0110425 A2 | 2/2001 |
| WO | 0132649 A1 | 5/2001 |
| WO | 03070753 A1 | 8/2003 |
| WO | 2004000289 A2 | 12/2003 |
| WO | 2004037810 A1 | 5/2004 |
| WO | 2004037811 A1 | 5/2004 |
| WO | 2004063171 A1 | 7/2004 |

OTHER PUBLICATIONS

Brittain, Polymorphism in Pharmaceutical Solids, 1999, pp. 5-8.
Rudolf et al. "Preparation of modified amino acids and their use as calcitonin gene-related peptide antagonists in pharmaceutical compositions" Patent No. WO 9811128, CAPLUS 128:257695 (1998).
Mallee et al. "Receptor activity modifying protein 1 determines the species selectivity of non-peptide CGRP receptor antagonists" Journal of Biological Chemistry 2002; CAPLUS 137:304712.
John J. Mallee et al; Receptor Activity-modifying Protein 1 Determines the Species Selectivity of Non-peptide CGRP Receptor Antagonists; The Journal of Biological Chemistry (Apr. 19, 2002) vol. 277 No. 16 p. 14294-14928; The American Society for Biochemistry and Molecular Biology, Inc.

* cited by examiner

*Primary Examiner*—Bruck Kifle
(74) *Attorney, Agent, or Firm*—Michael P. Morris; Mary-Ellen M. Devlin; Alan R. Stempel

(57) ABSTRACT

The present invention relates to the CGRP antagonists of general formula

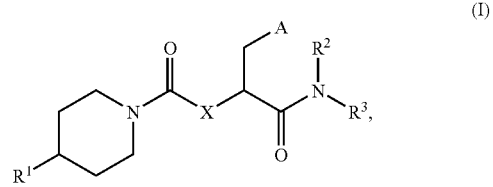

(I)

wherein A, X and $R^1$ to $R^3$ are defined as in claim 1, the tautomers, the diastereomers, the enantiomers, the hydrates thereof, the mixtures thereof and the salts thereof and the hydrates of the salts, particularly the physiologically acceptable salts thereof with inorganic or organic acids, pharmaceutical compositions containing these compounds, the use thereof and processes for the preparation thereof.

5 Claims, No Drawings

SELECTED CGRP-ANTAGONISTS, PROCESS FOR PREPARING THEM AND THEIR USE AS PHARMACEUTICAL COMPOSITIONS

The present invention relates to the CGRP antagonists of general formula

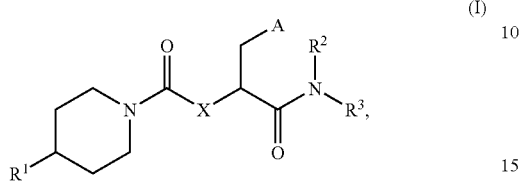

the tautomers, the diastereomers, the enantiomers, the hydrates thereof, the mixtures thereof and the salts thereof as well as the hydrates of the salts, particularly the physiologically acceptable salts thereof with inorganic or organic acids or bases, pharmaceutical compositions containing these compounds, the use thereof and processes for the preparation thereof.

In the above general formula (I)

A denotes a group of formula

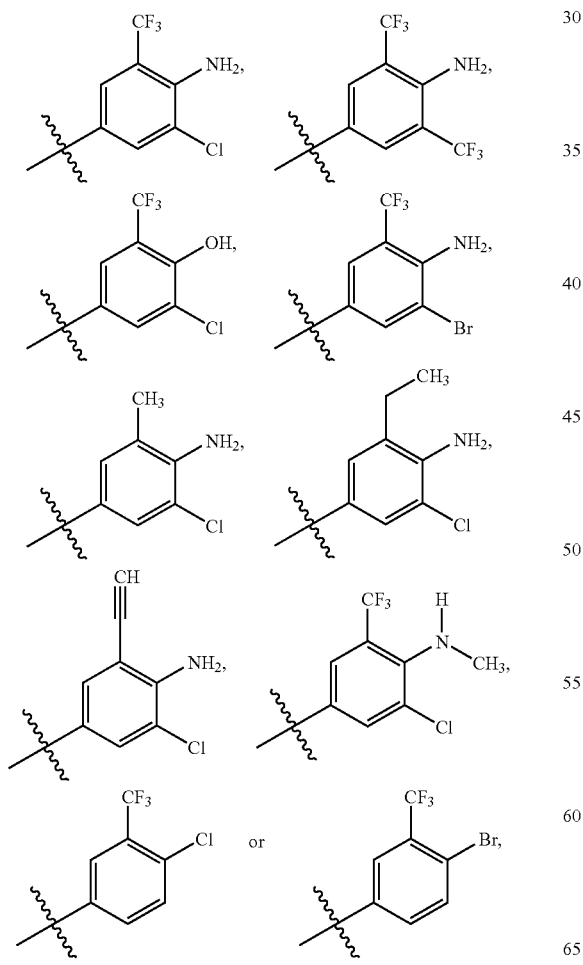

X denotes an oxygen atom, a methylene or NH group, $R^1$ denotes a group of formula

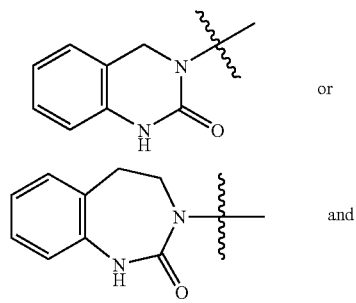

$-NR^2R^3$ denotes a group of formula

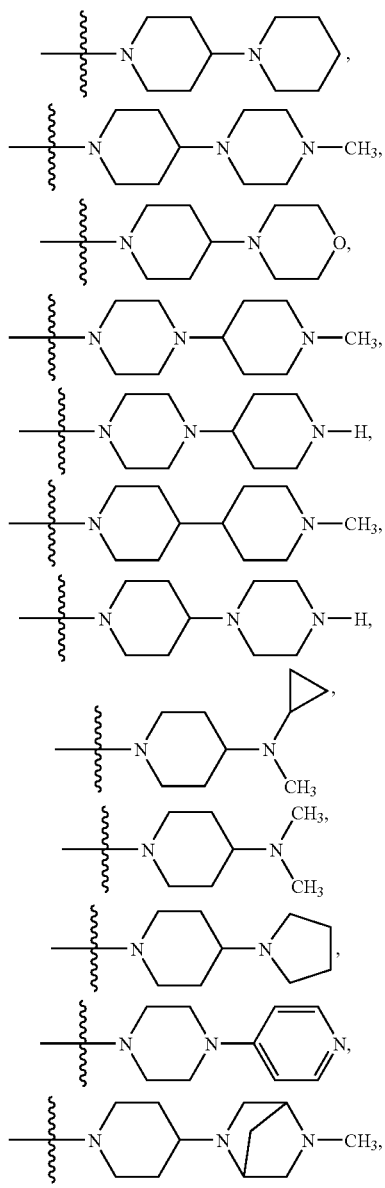

-continued
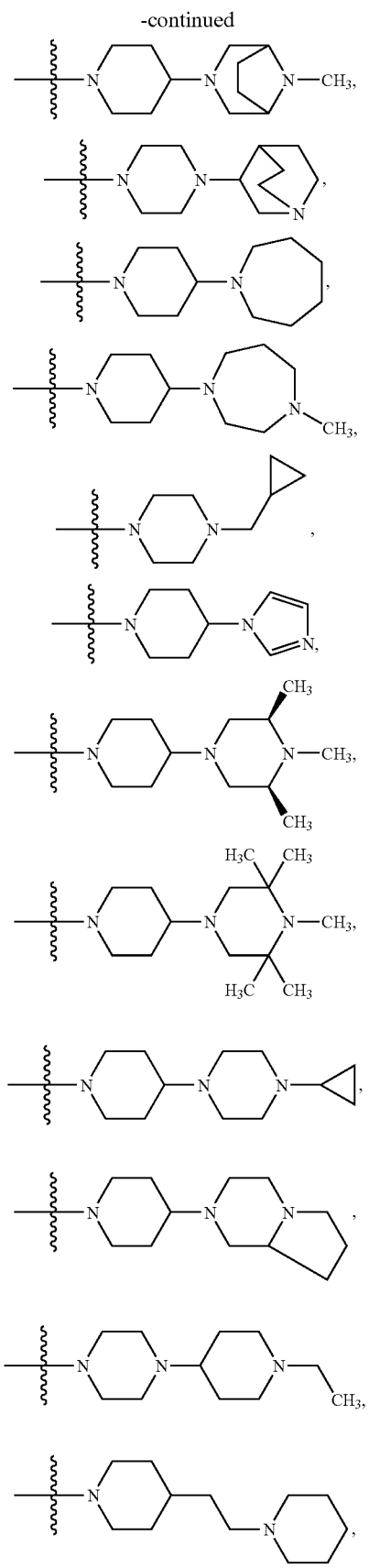
-continued
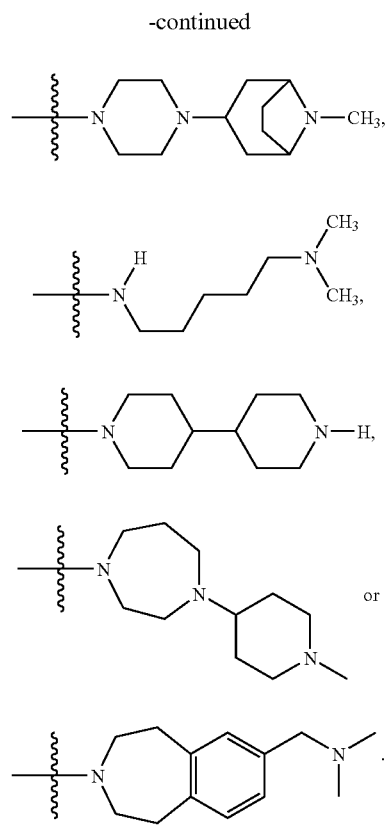
Particularly preferred compounds of the above general formula (I) are as follows, for example:
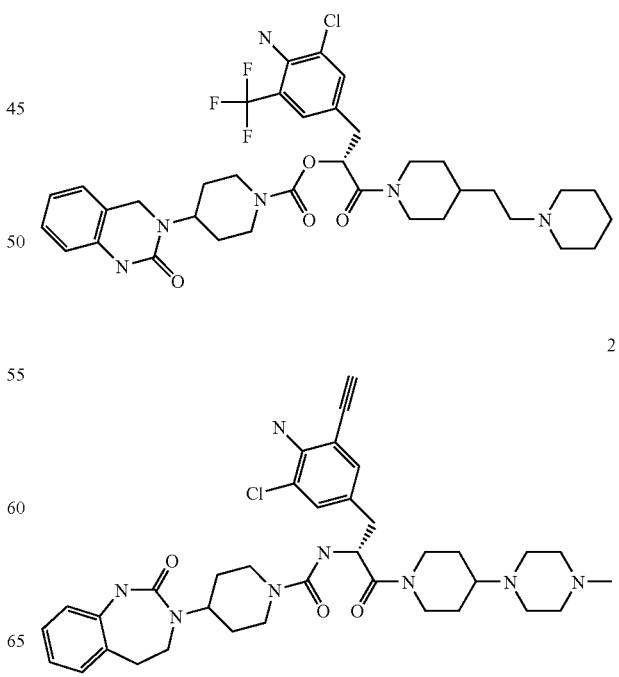

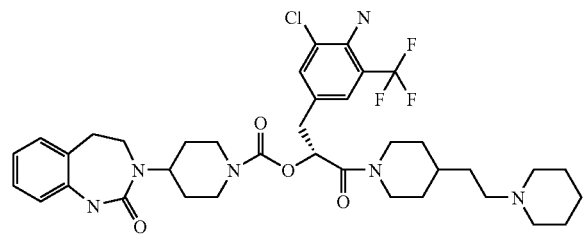
3
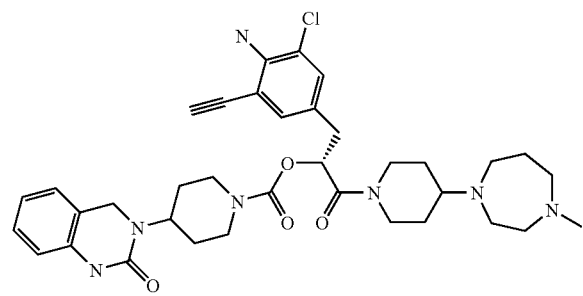
4
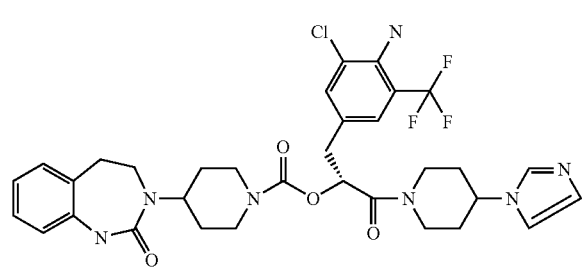
5
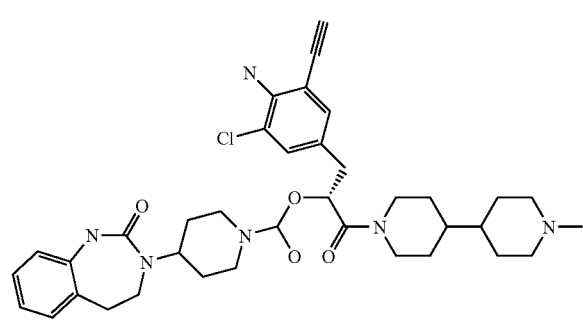
6
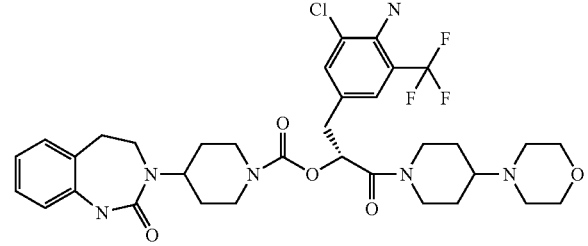
5
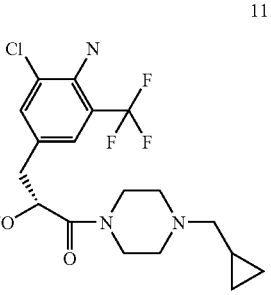
7
8
9
10
11

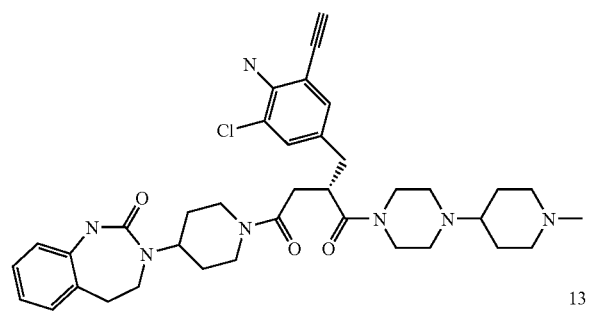
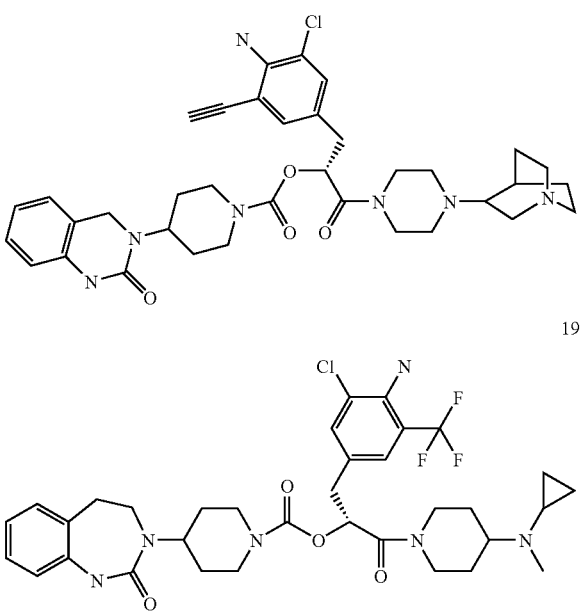
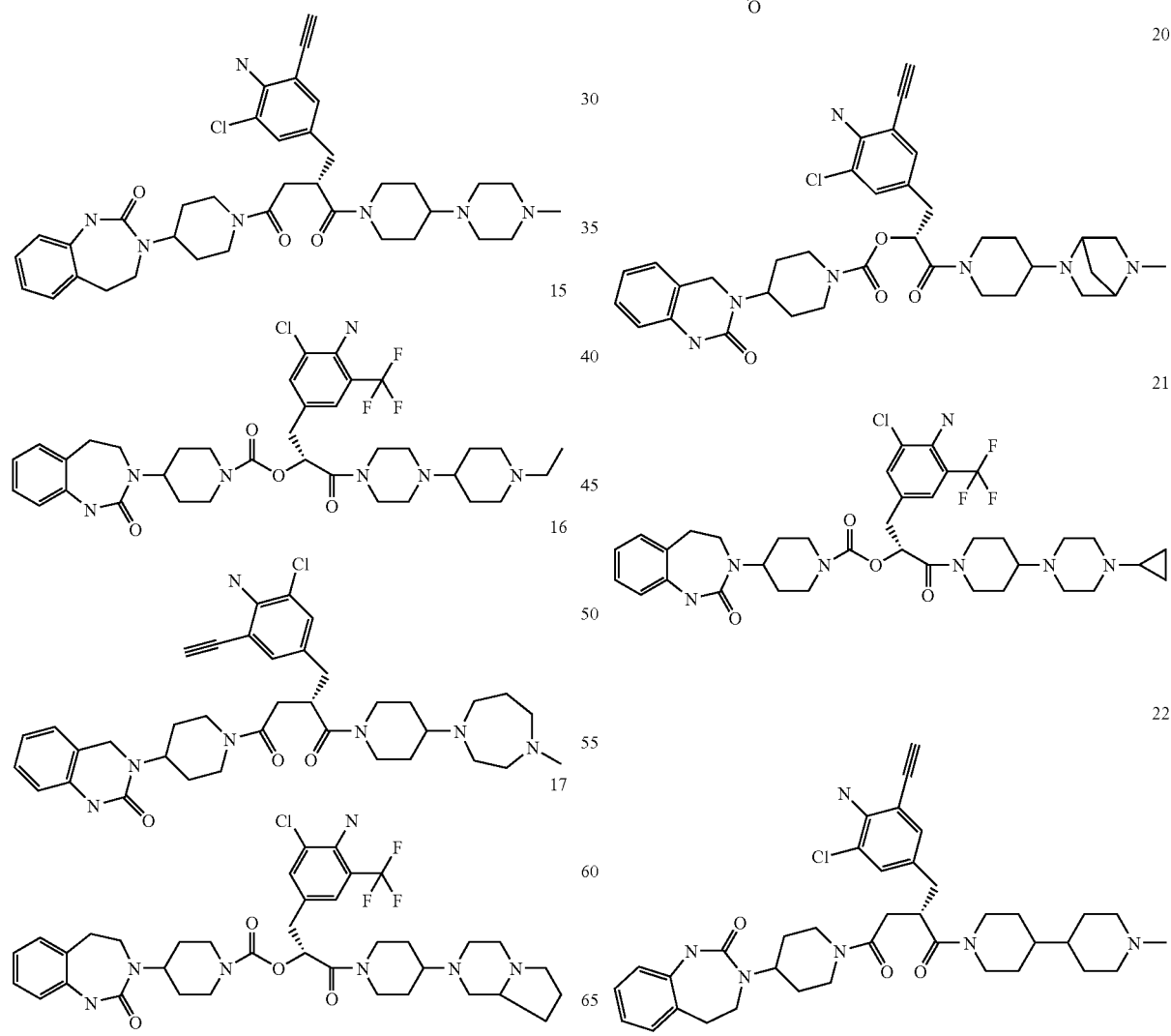

-continued
23
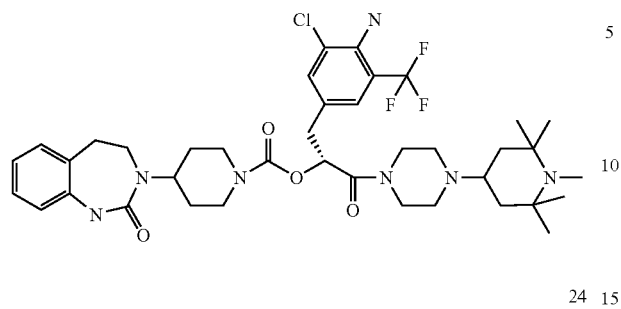
24
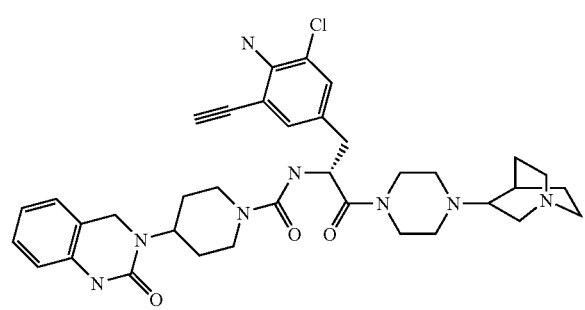
25
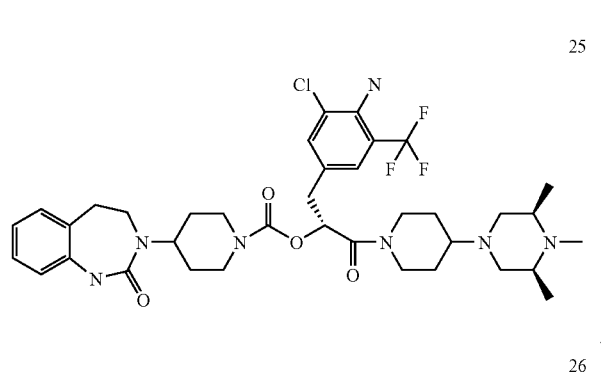
26
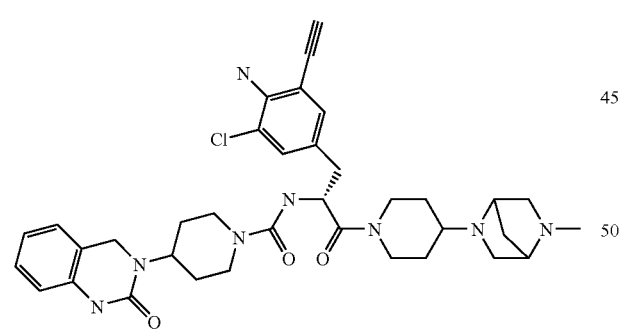
27
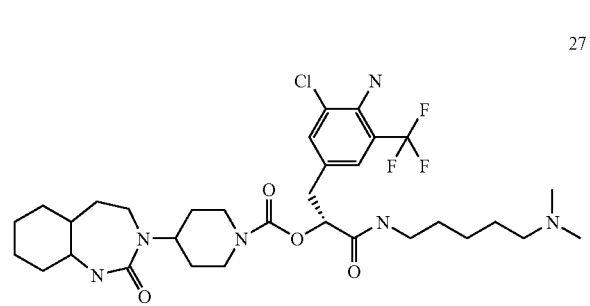
-continued
28
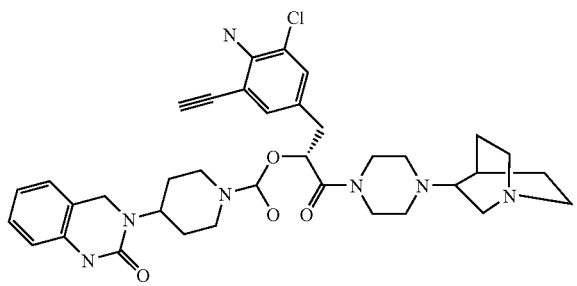
29
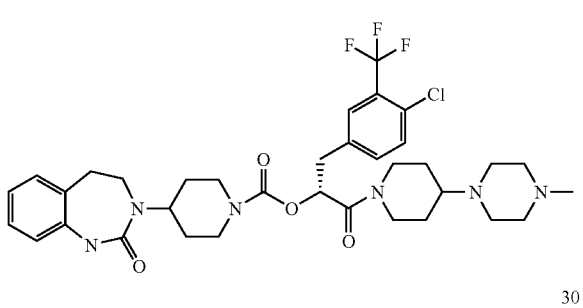
30
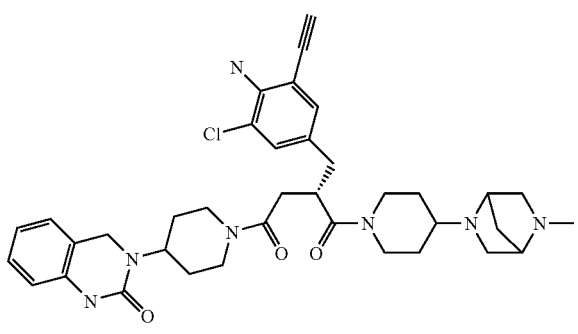
31
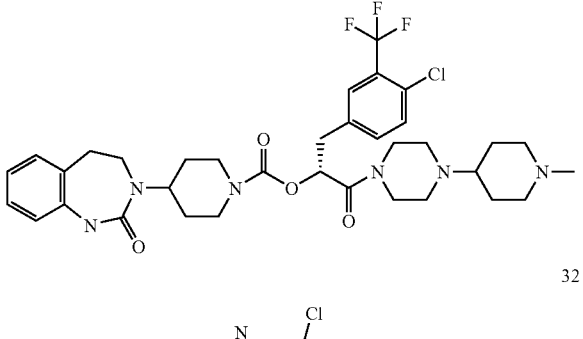
32
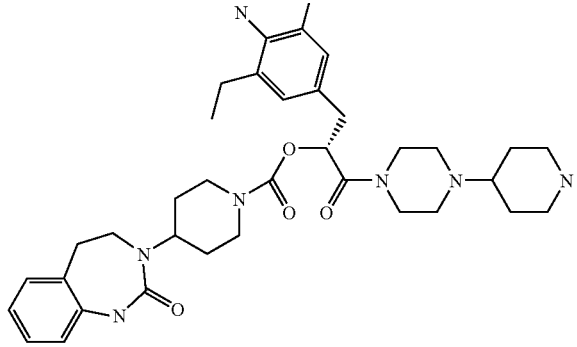

-continued
33
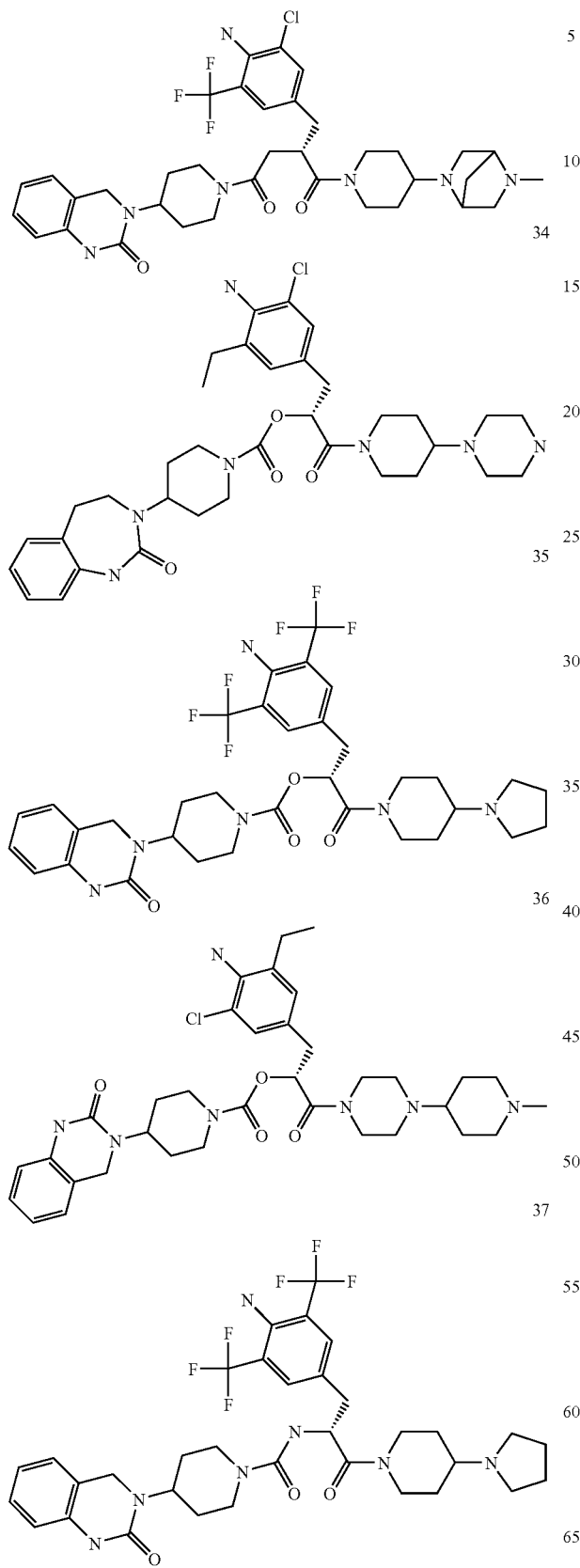
34
35
36
37
-continued
38
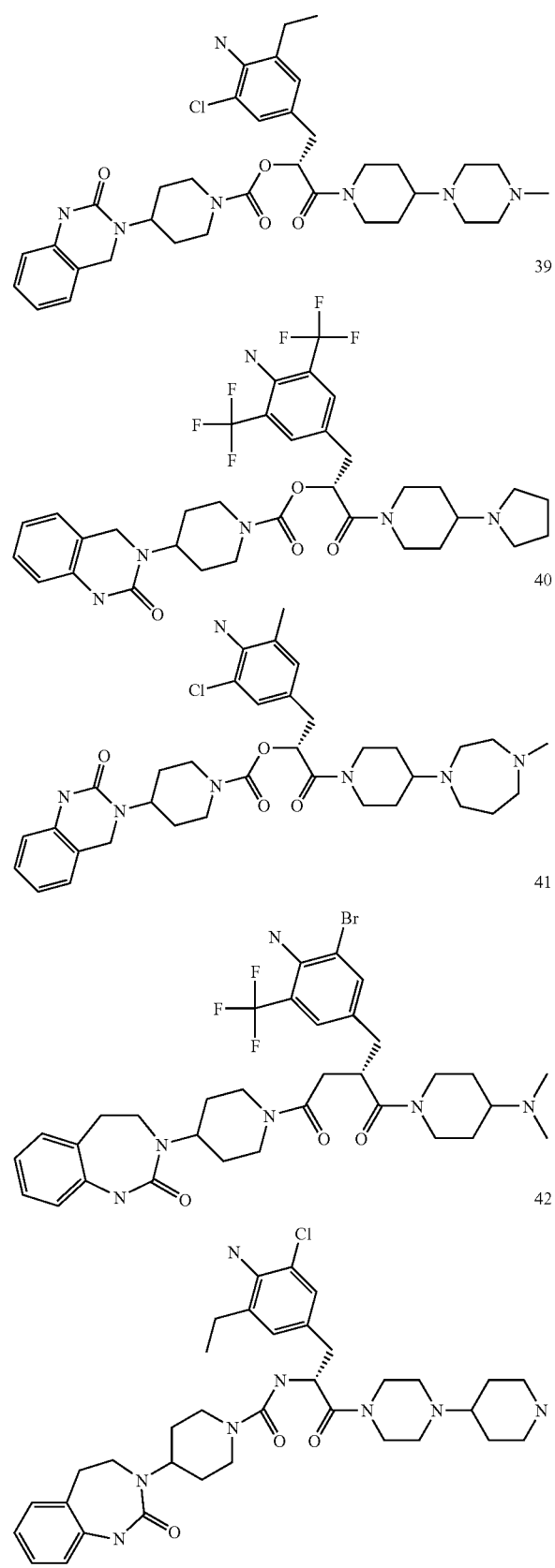
39
40
41
42

-continued
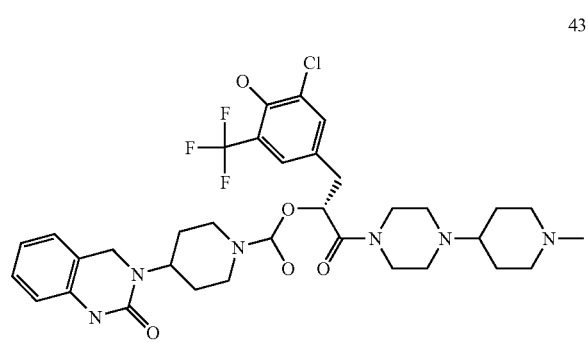
43
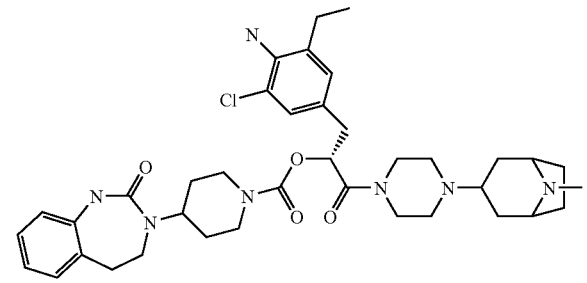
47
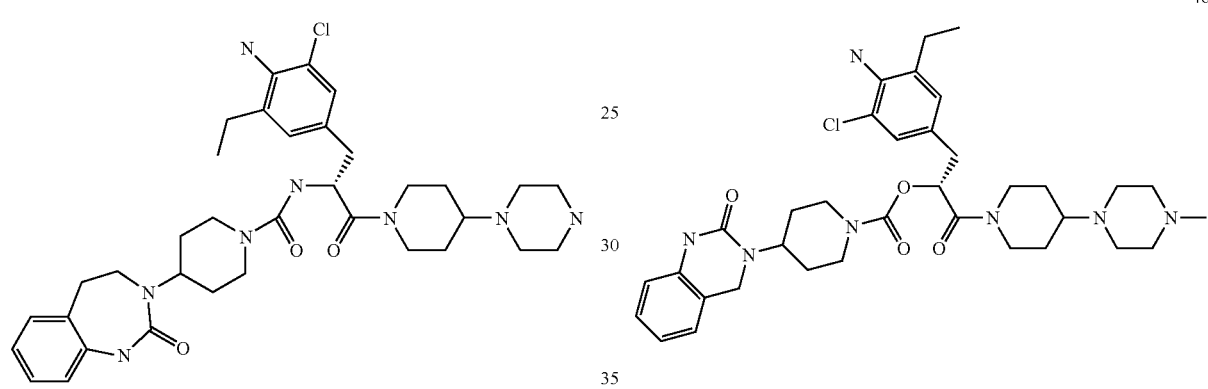
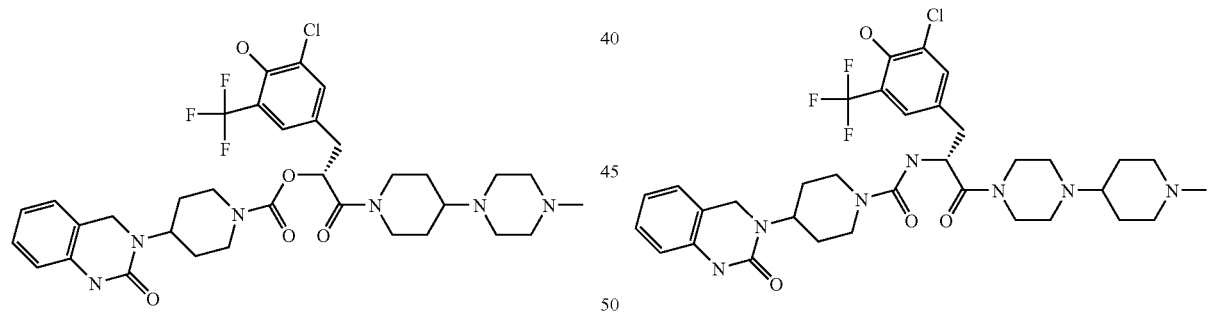
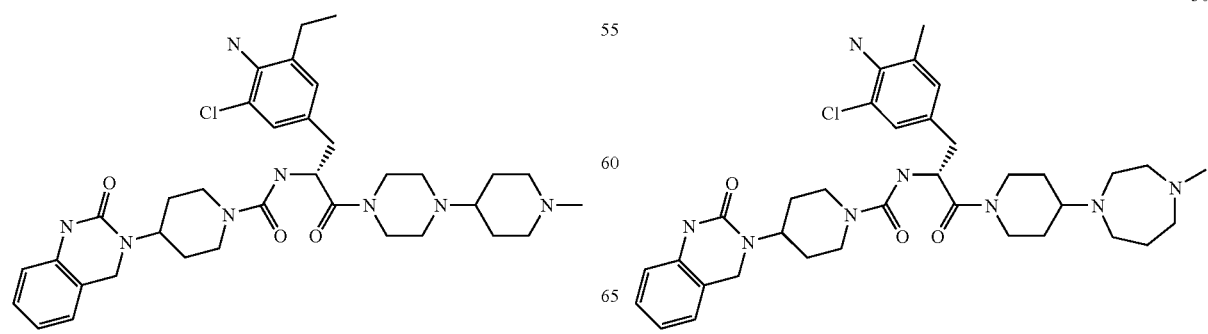

-continued
51
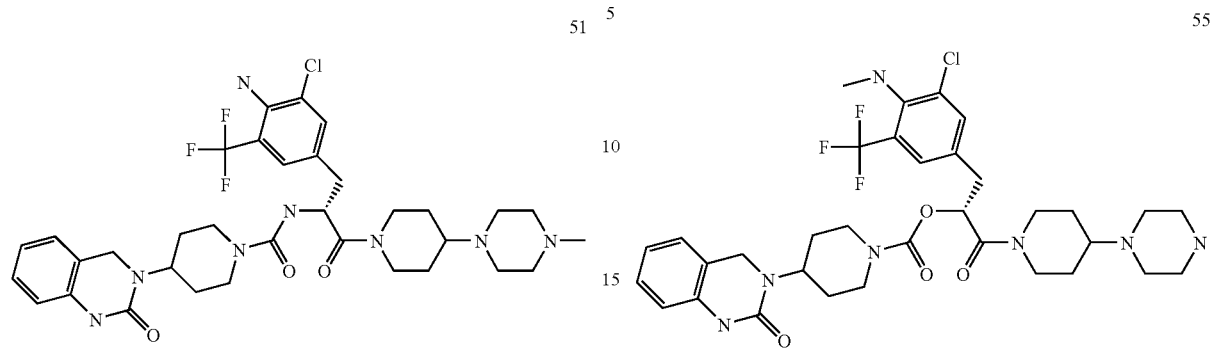
52
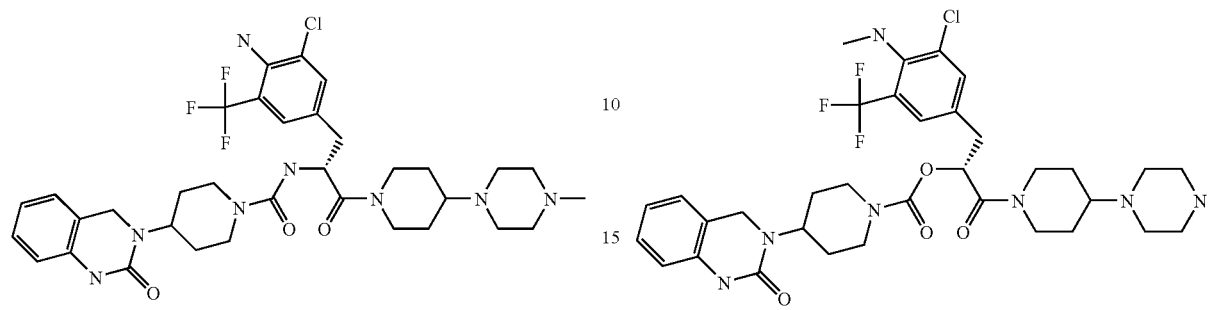
53
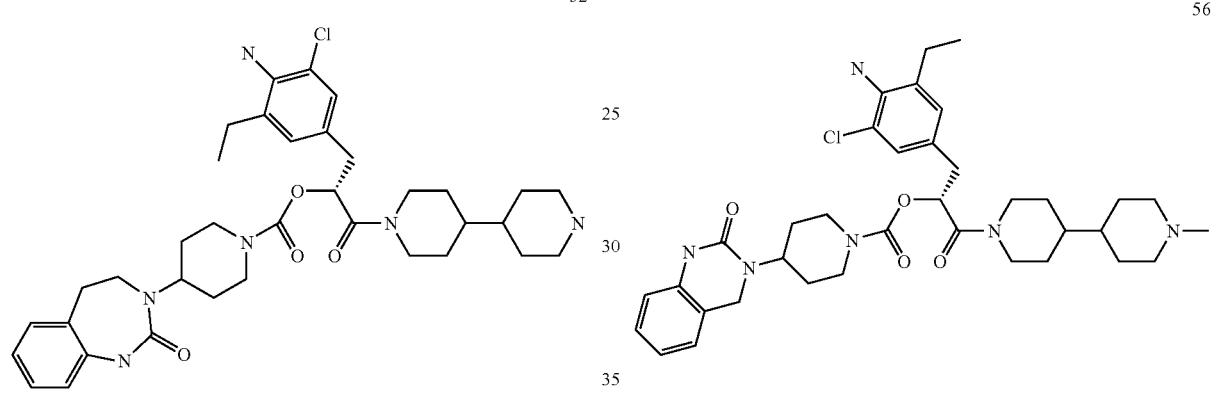
54
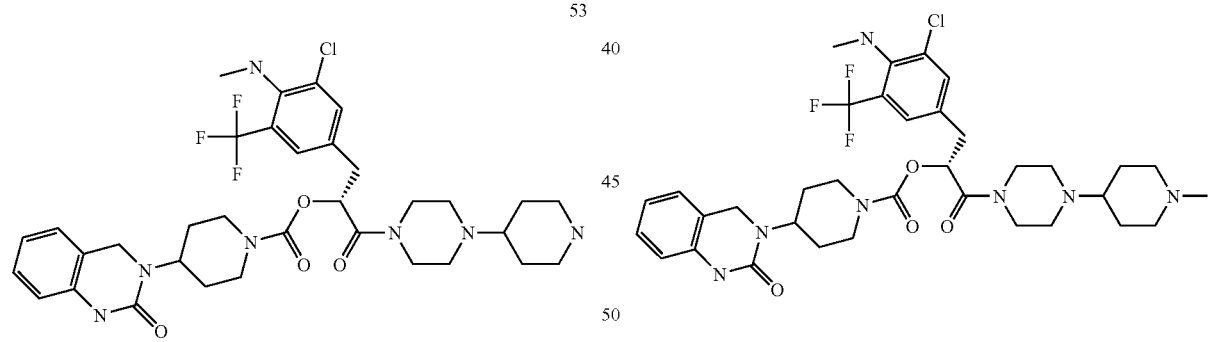
-continued
55
56
57
58
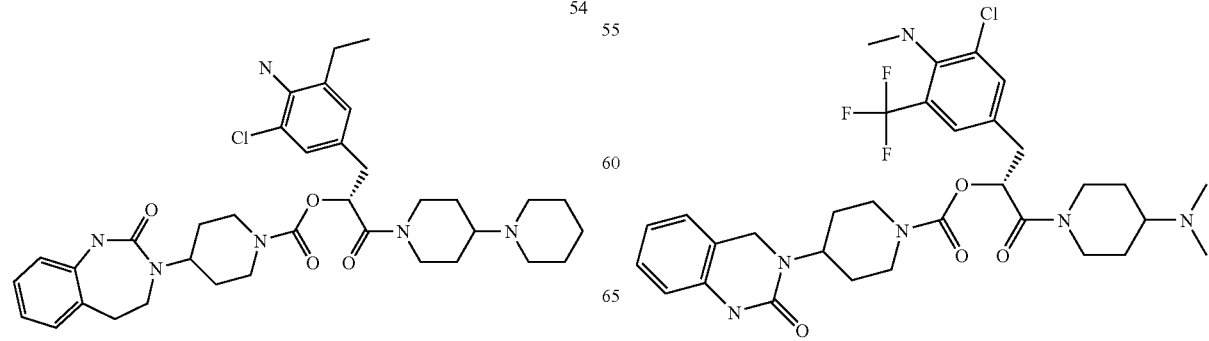

59
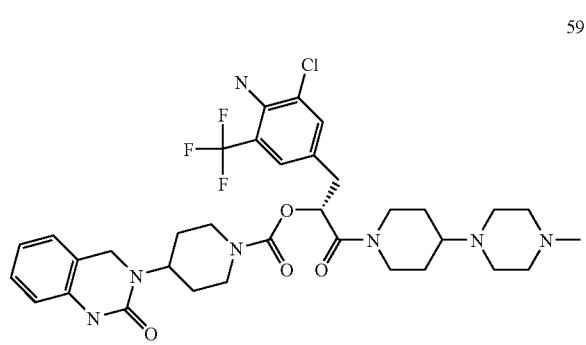
63
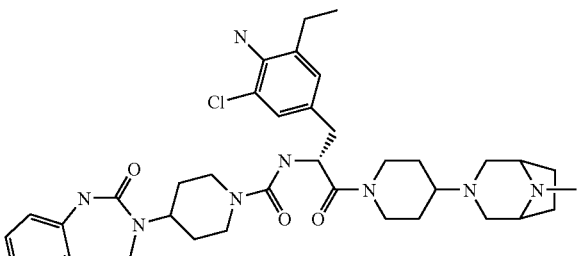
60
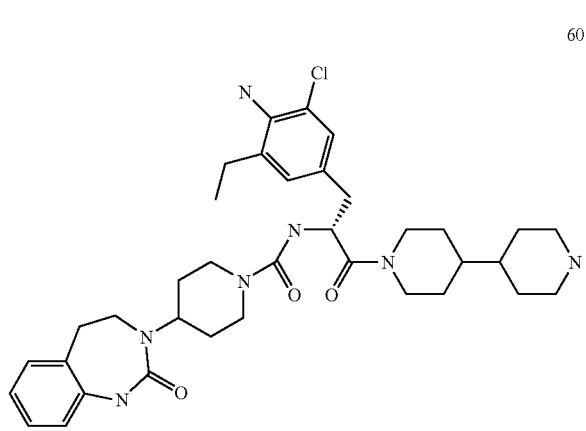
64
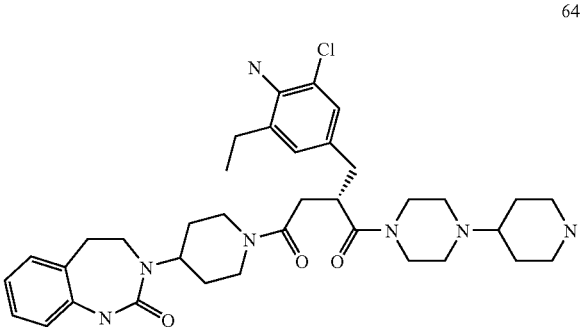
61
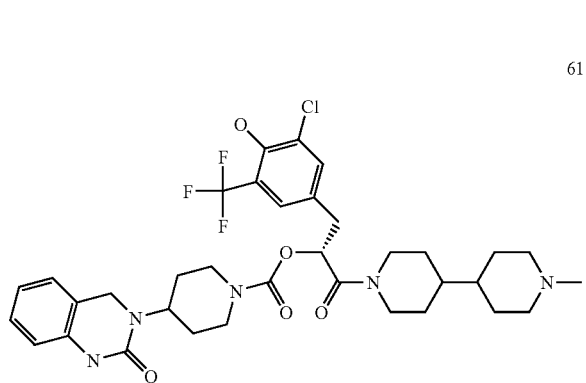
65
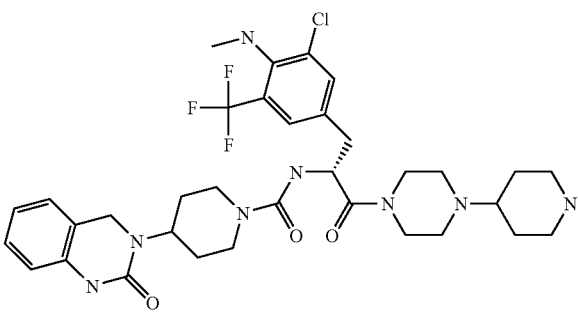
62
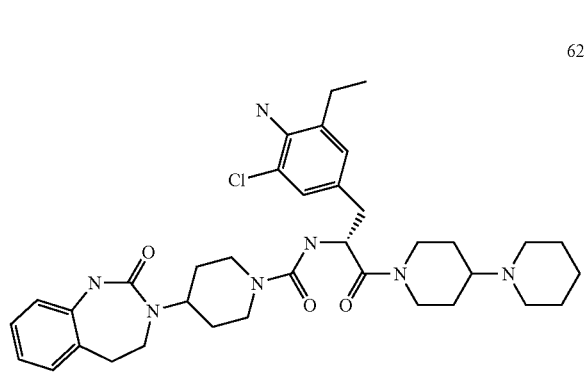
66
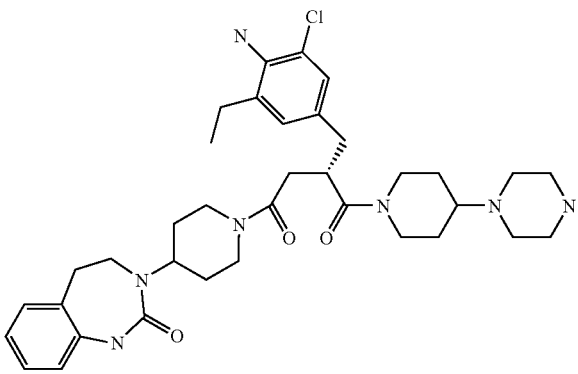

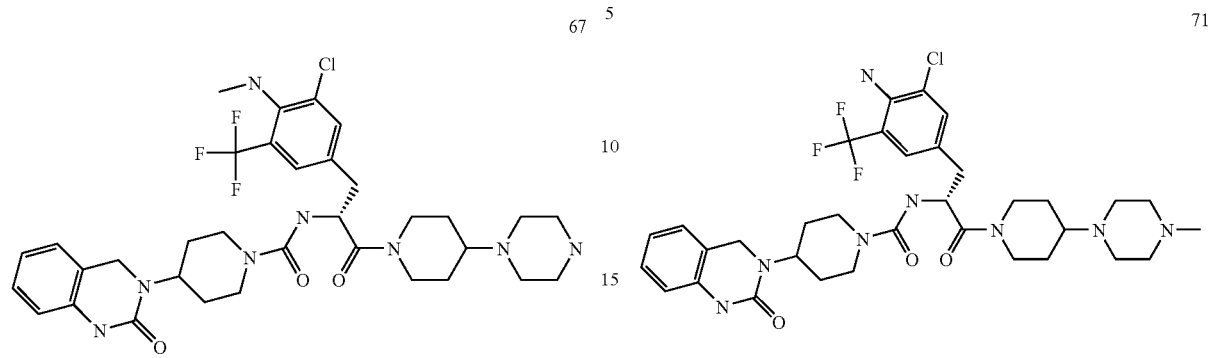
67
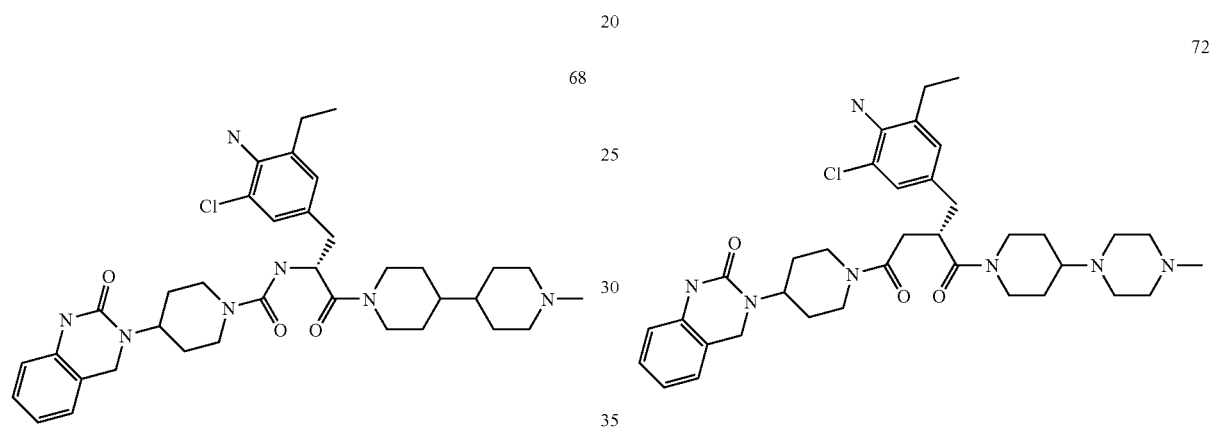
68
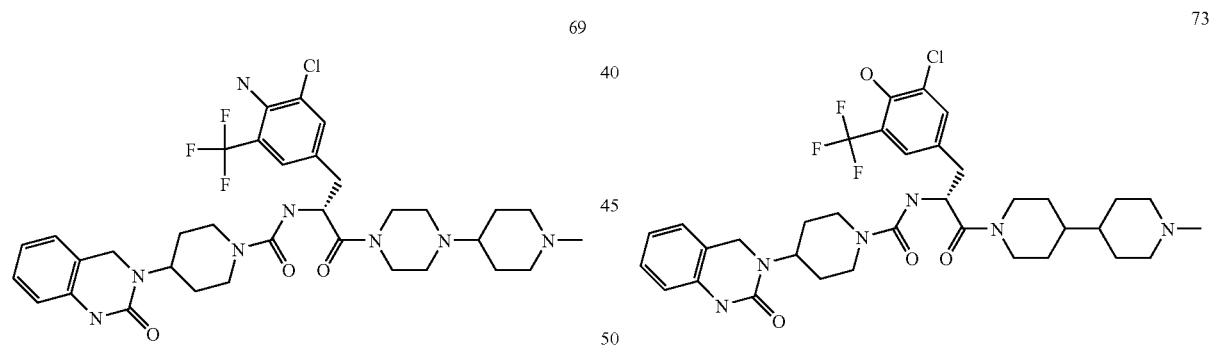
69
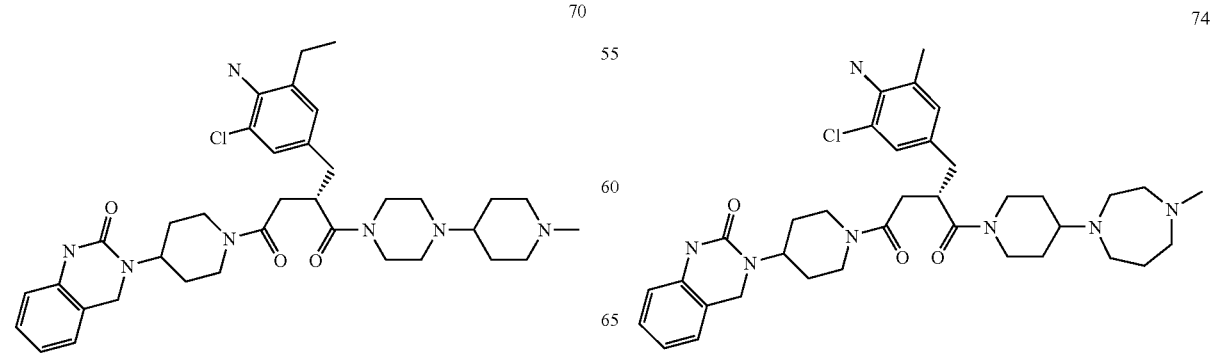
70
71
72
73
74

-continued

-continued

85

86

87

88

89

-continued

90

91

92

93

94

-continued
95
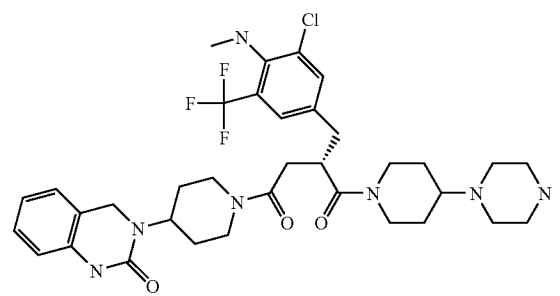
96
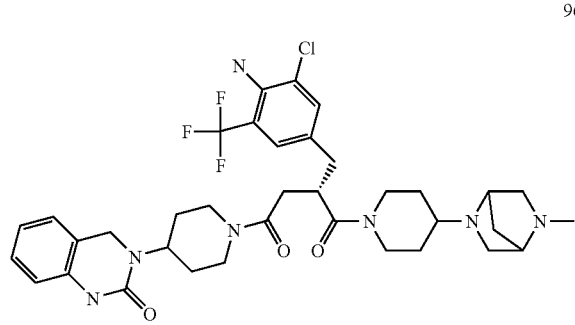
97
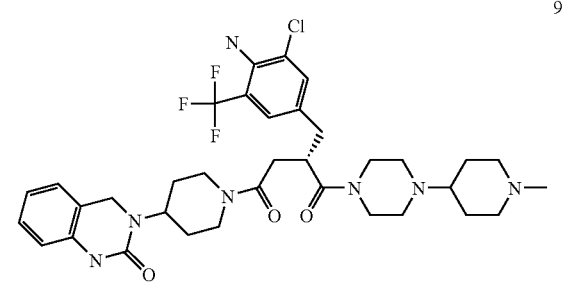
98
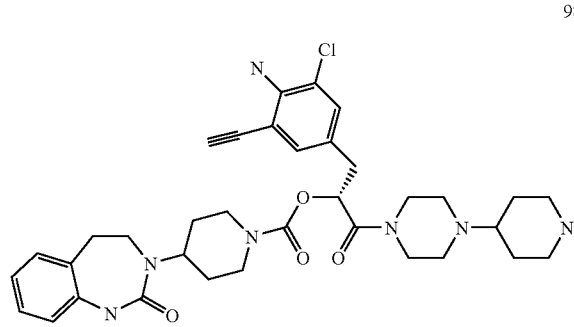
99
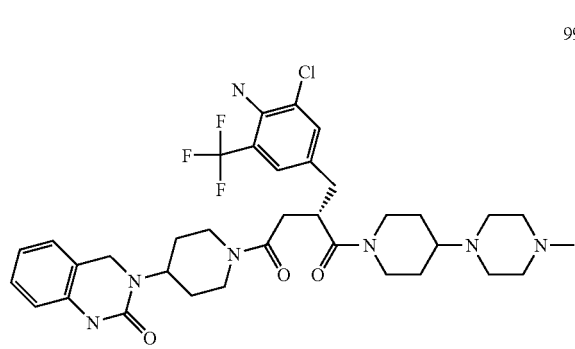
-continued
100
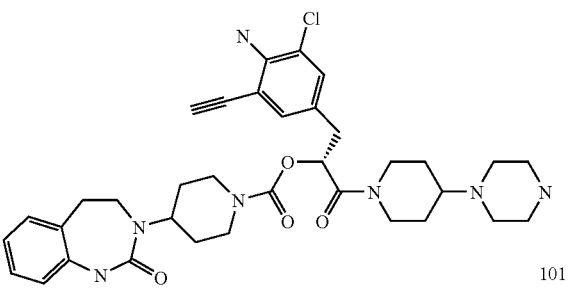
101
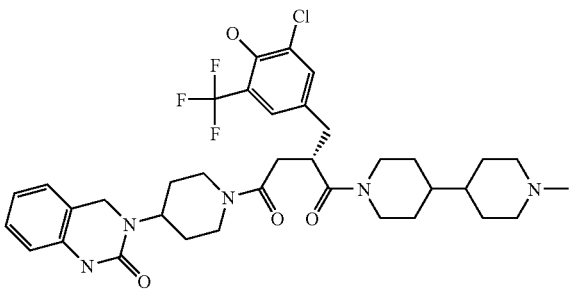
102
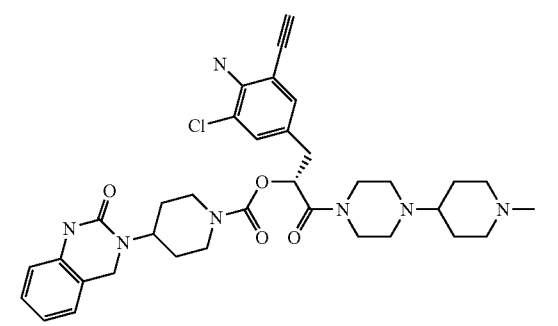
103
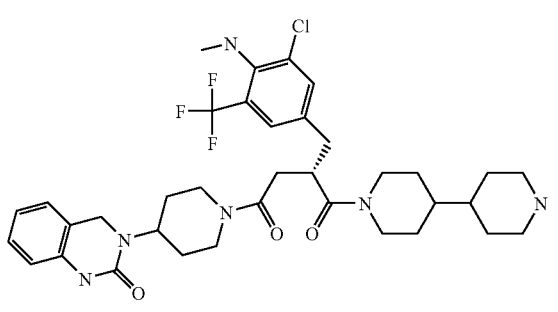
104
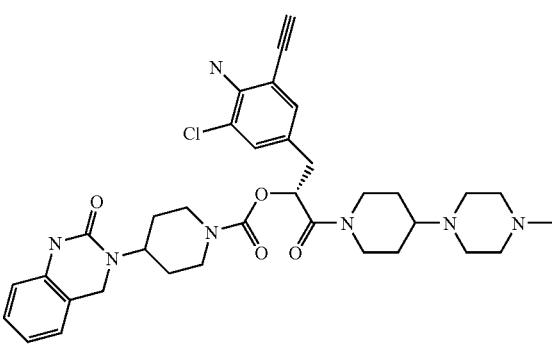

-continued
105
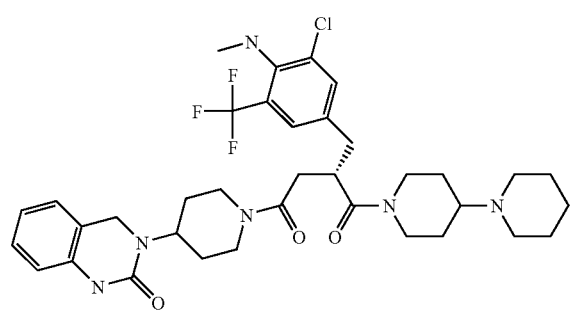
106
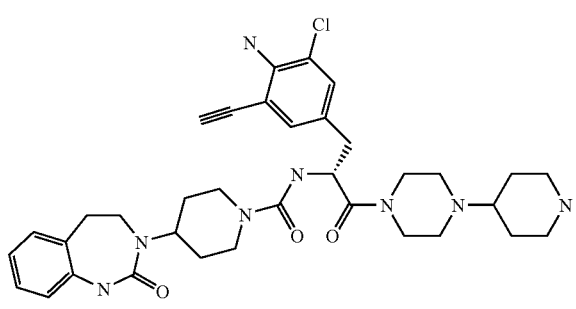
107
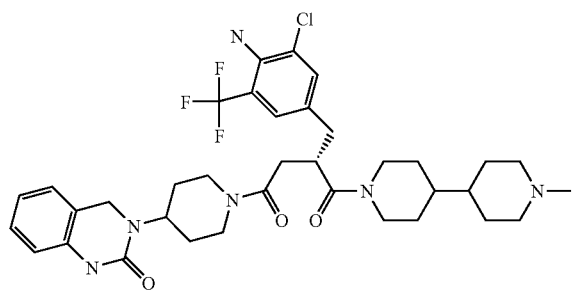
108
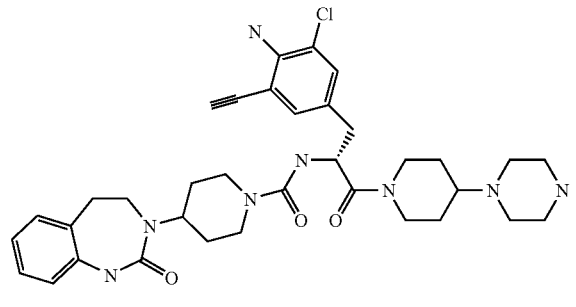
109
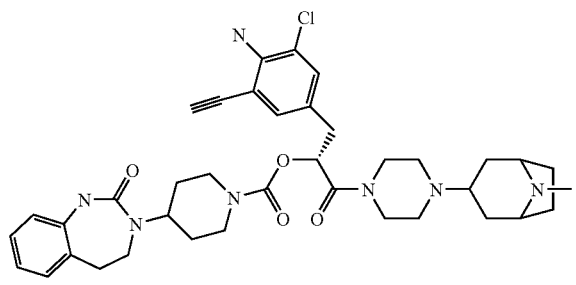
-continued
110
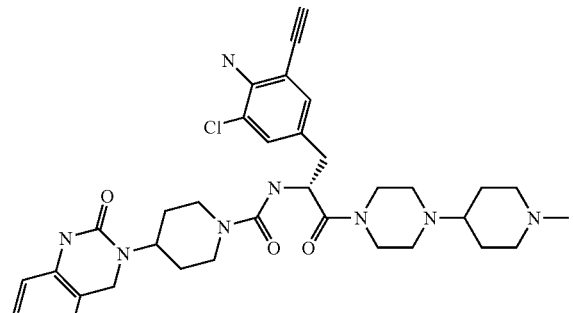
111
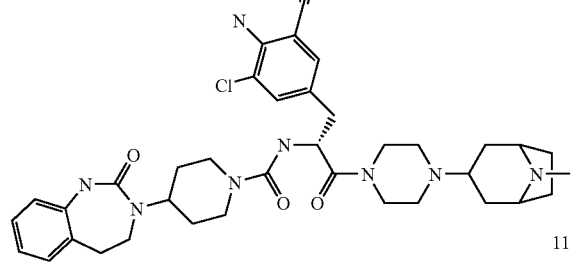
112
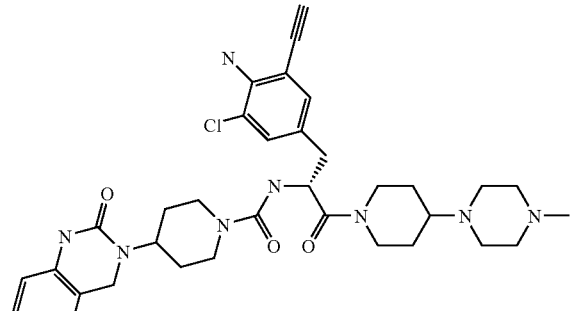
113
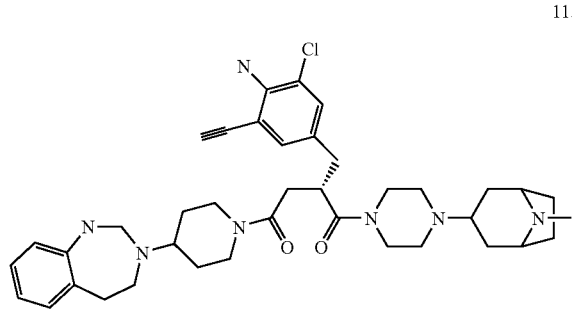
114
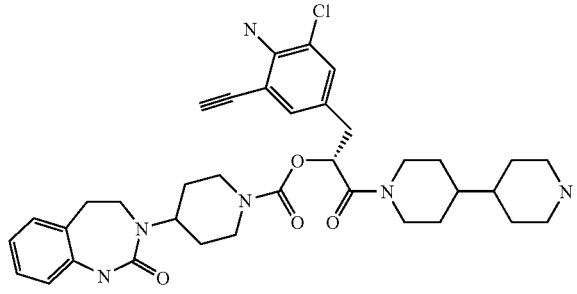

-continued
115
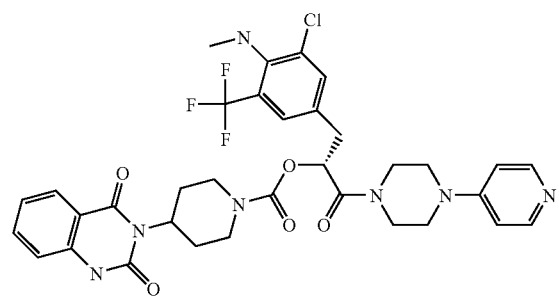
116
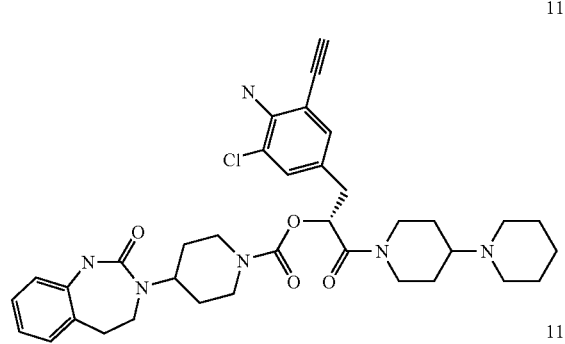
117
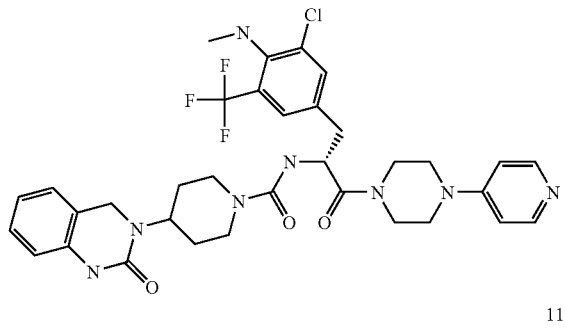
118
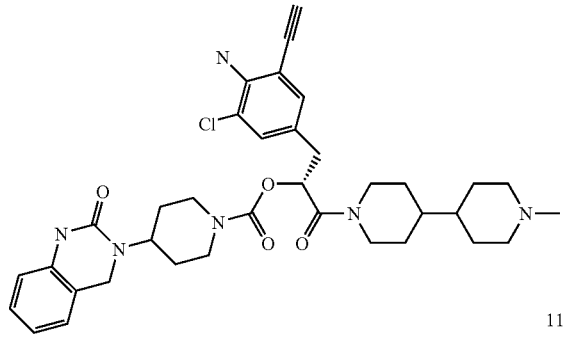
119
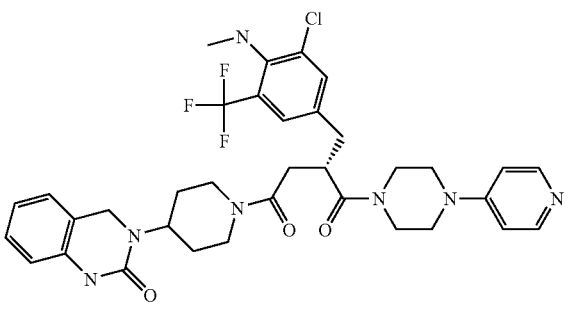
-continued
120
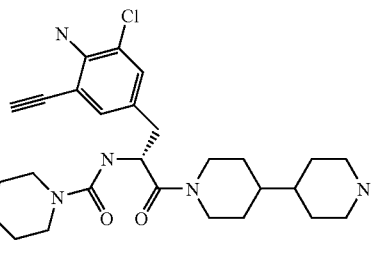
121
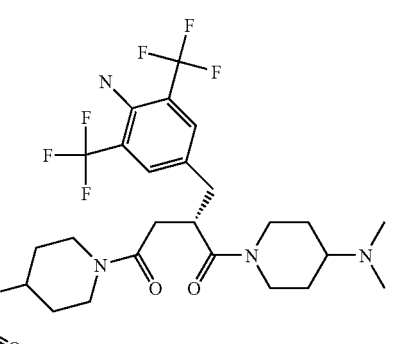
122
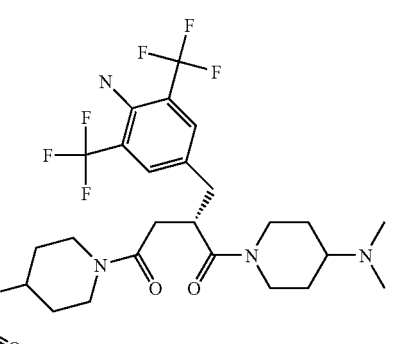
123
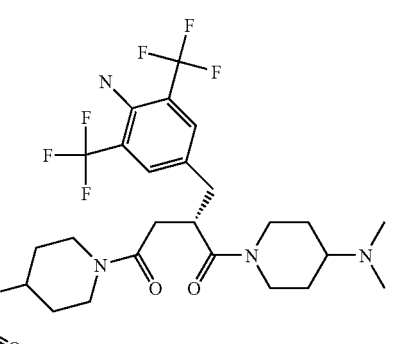
124
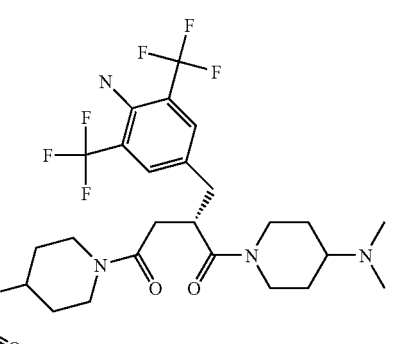

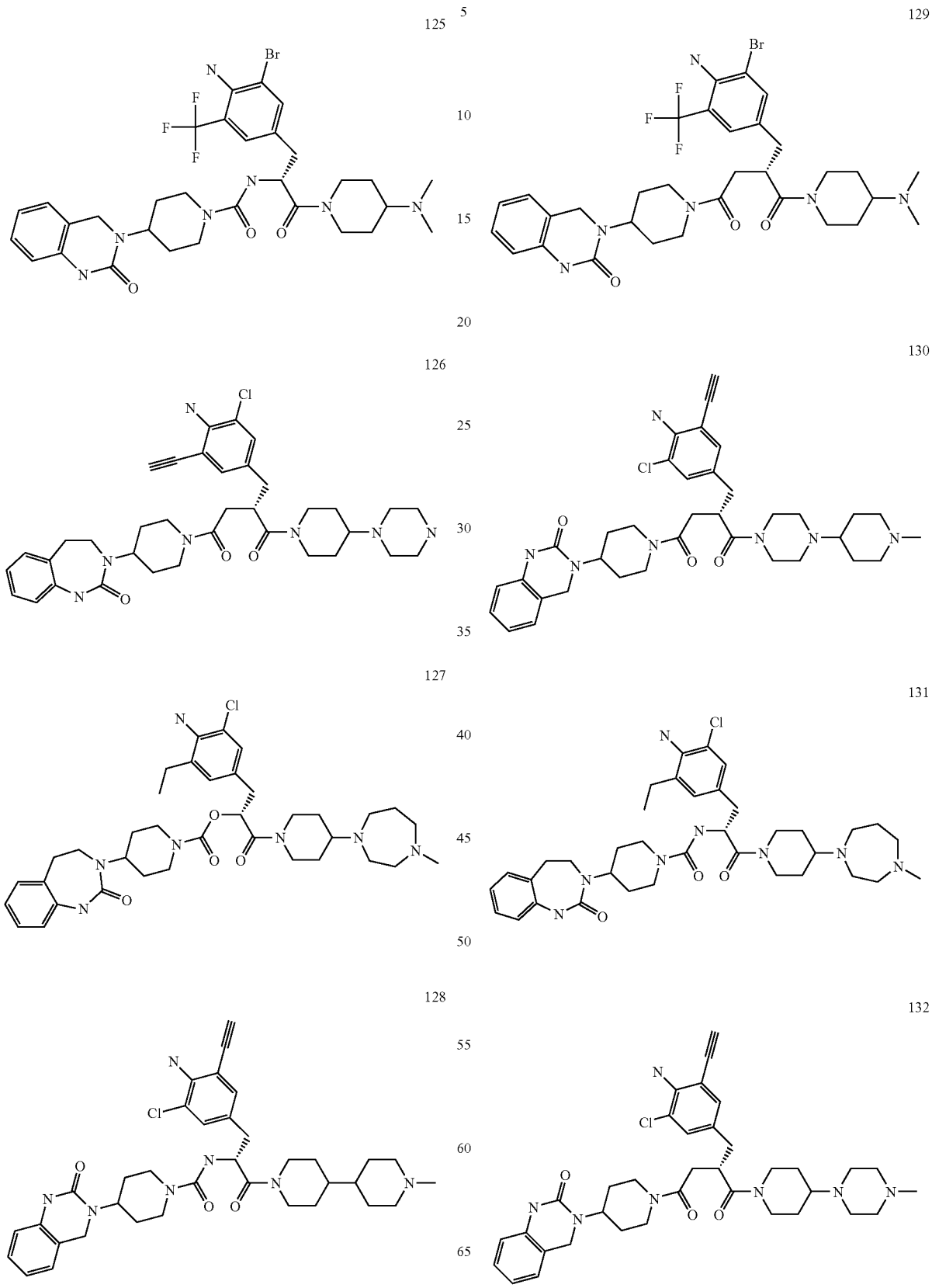

133
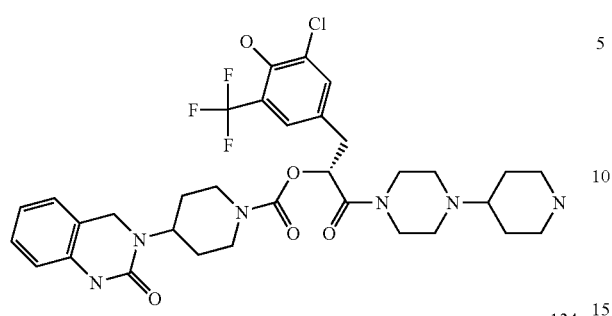
134
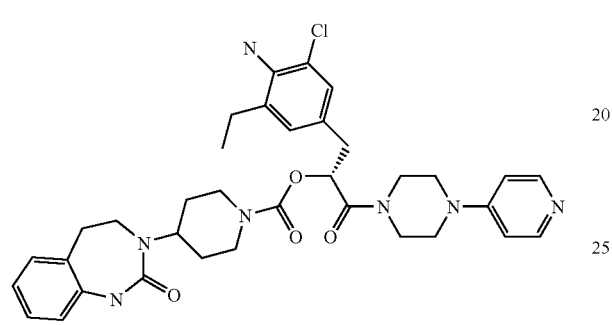
135
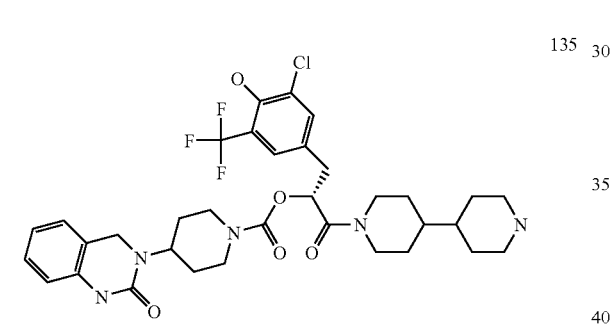
136
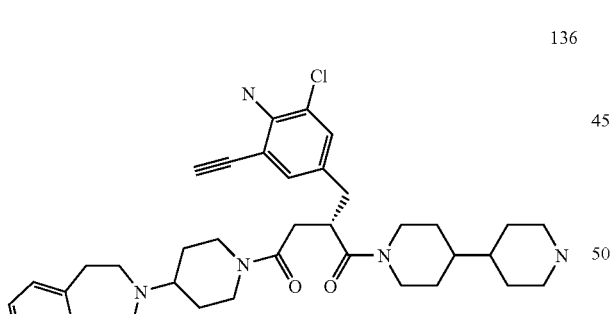
137
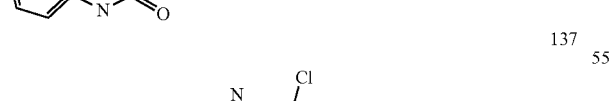
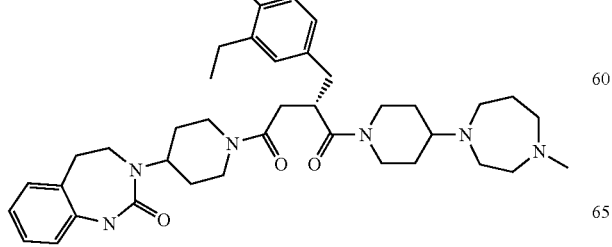
138
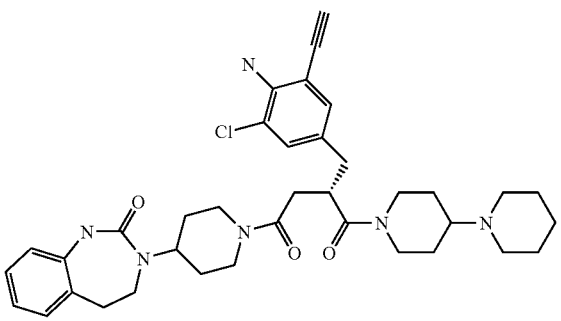
139
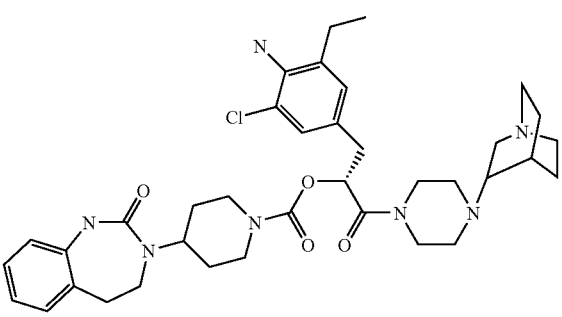
140
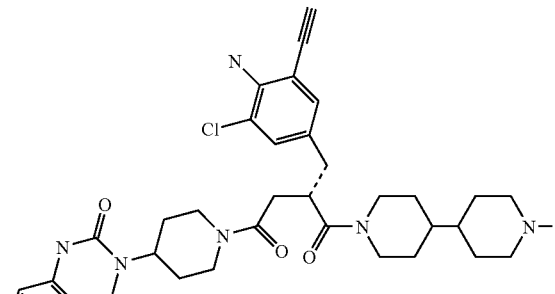
141

142
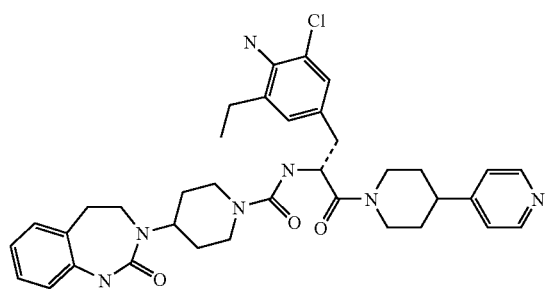
143
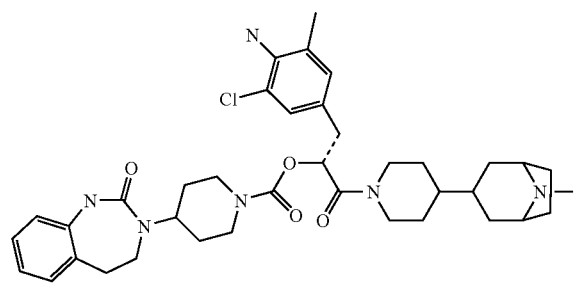
144
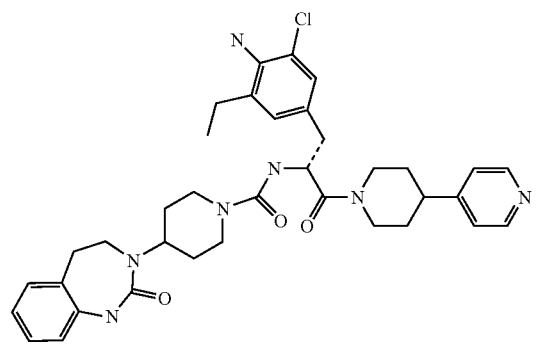
145
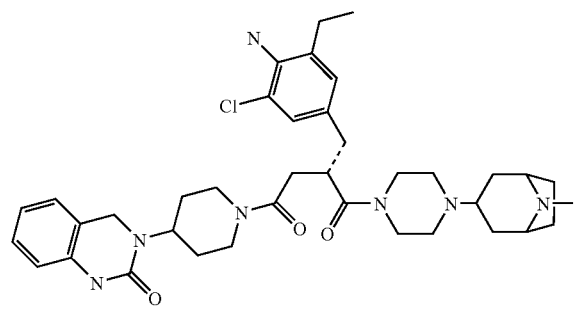
146
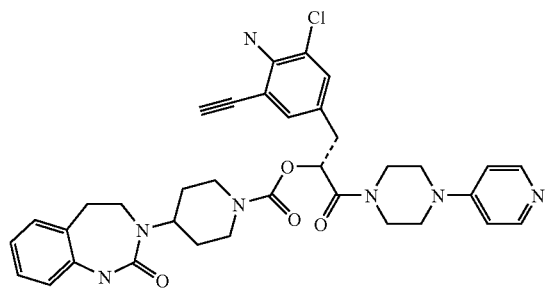
147
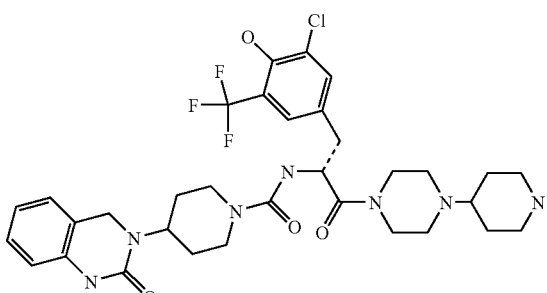
148
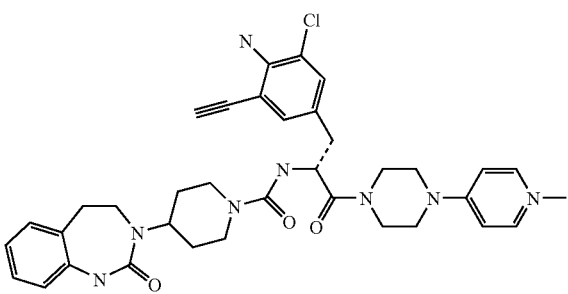
149
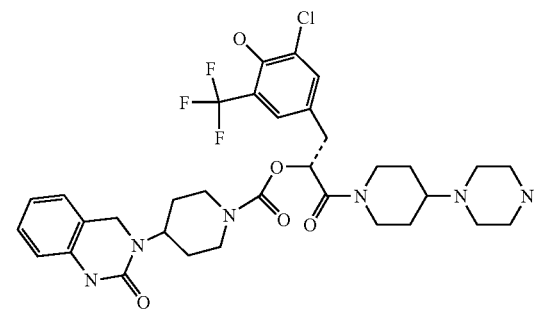
150
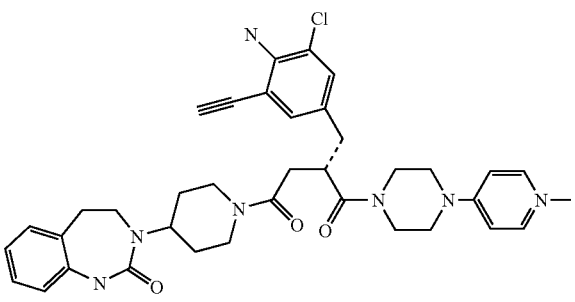
151
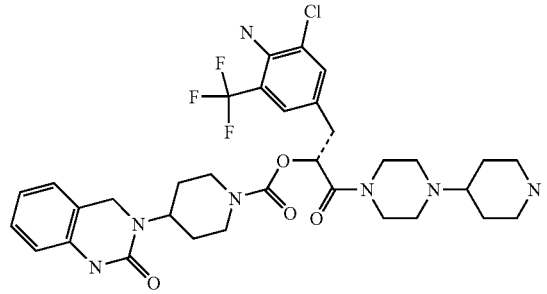

152
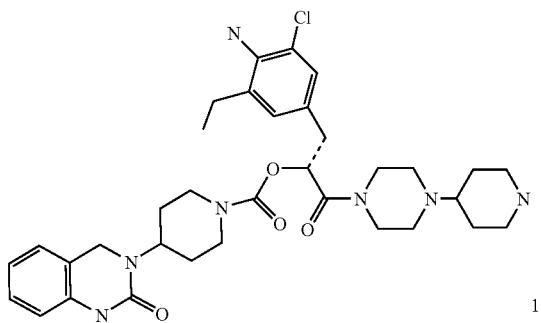
153
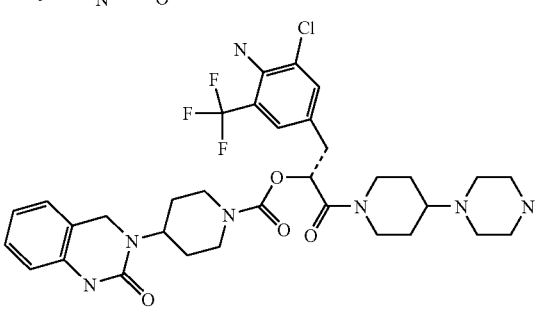
154
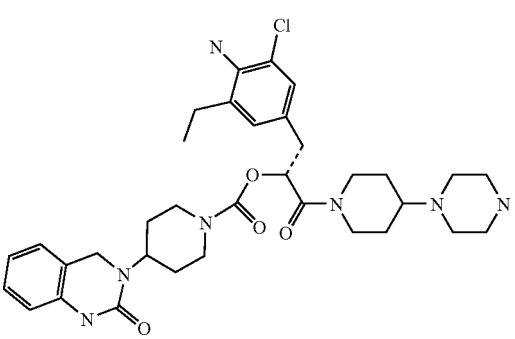
155
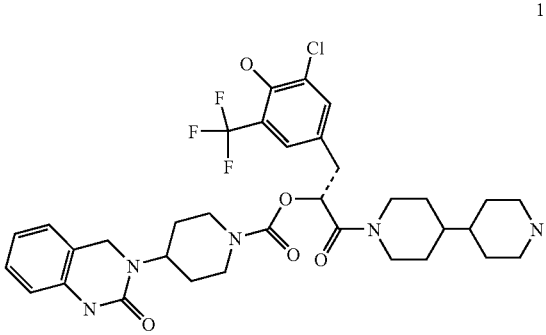
156
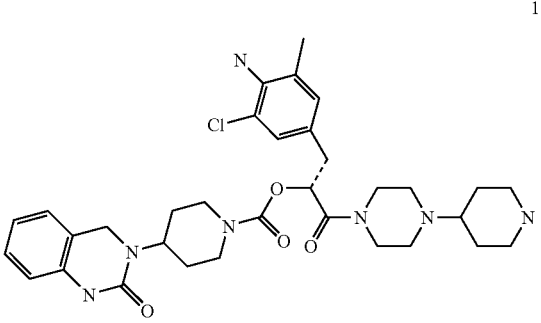
157
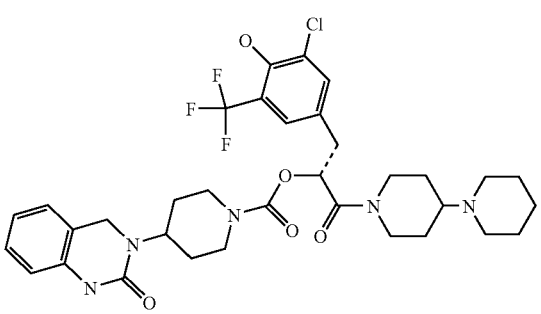
158
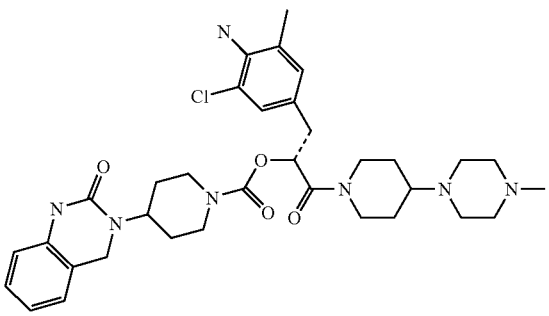
159
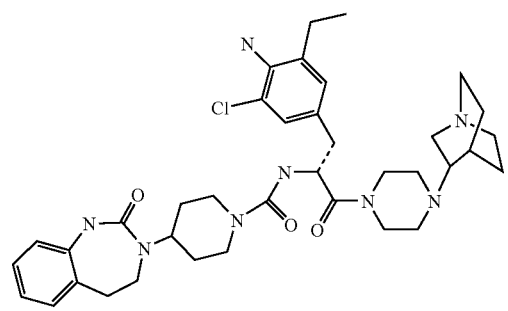
160
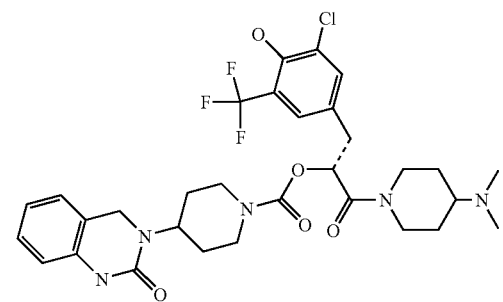

-continued

171
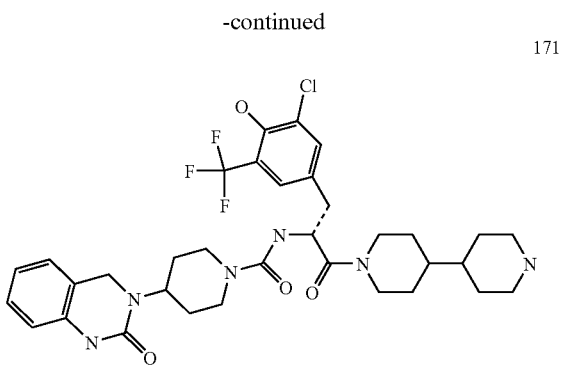
172
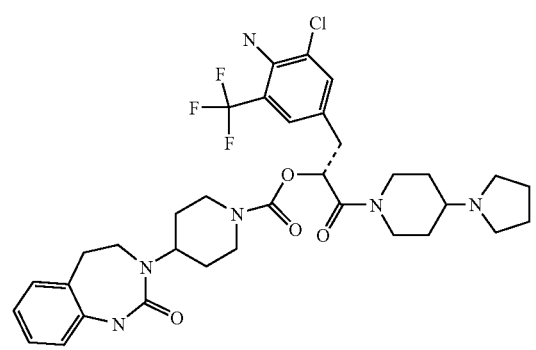
173
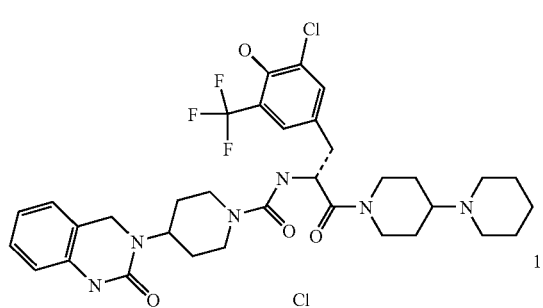
174
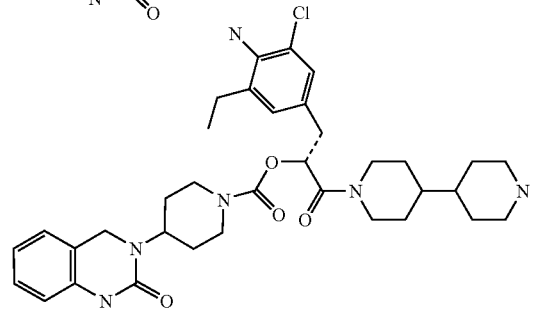
175
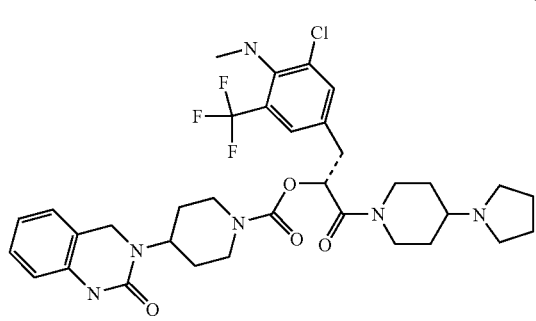
176
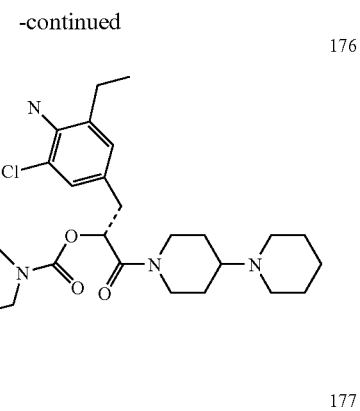
177
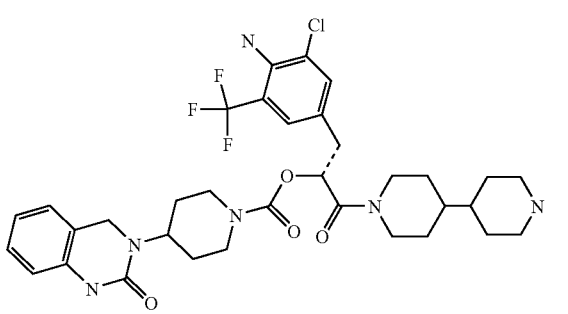
178
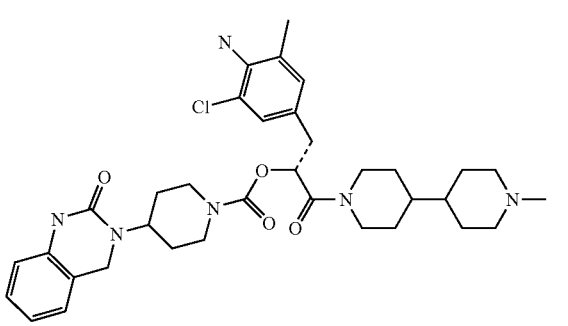
179
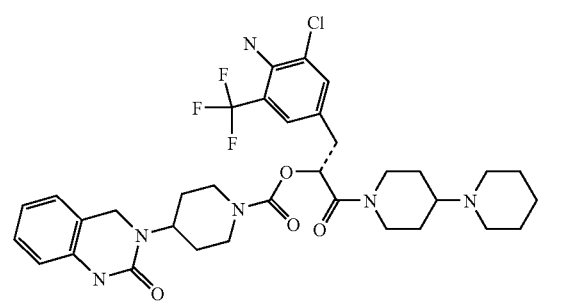
180
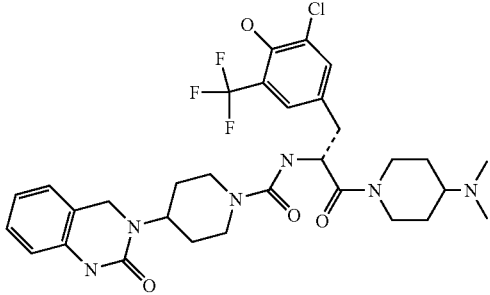

181
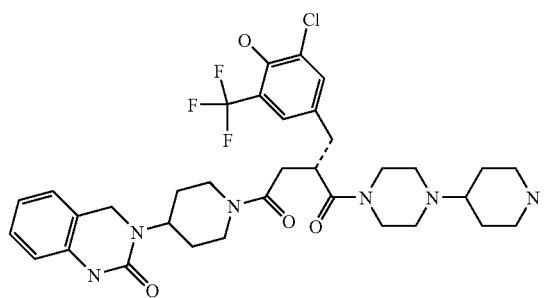
182
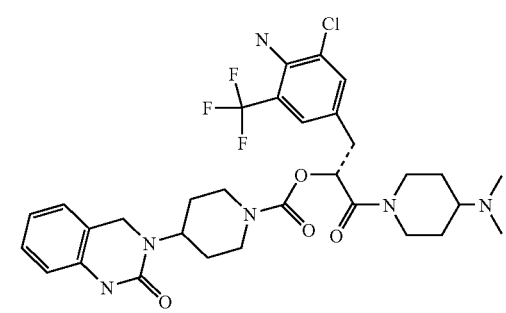
183
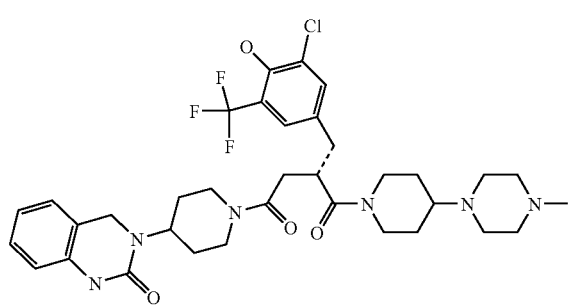
184
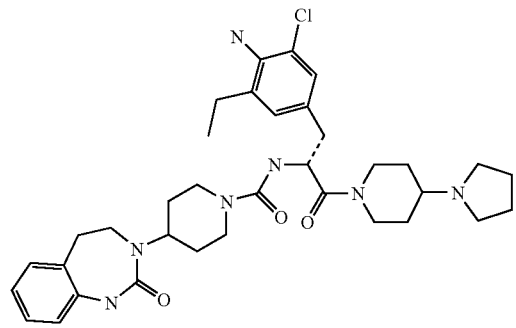
185
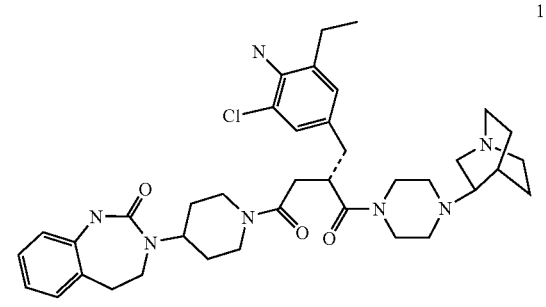
186
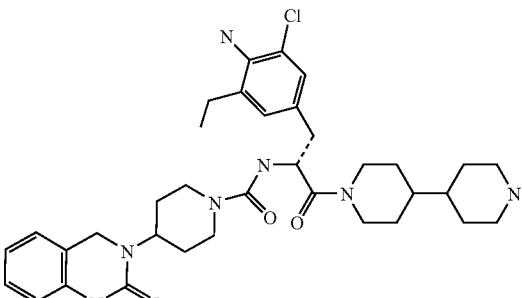
187
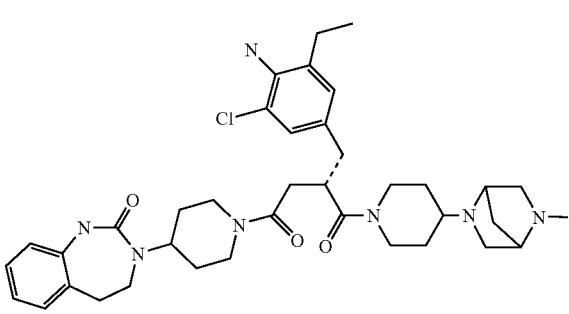
188
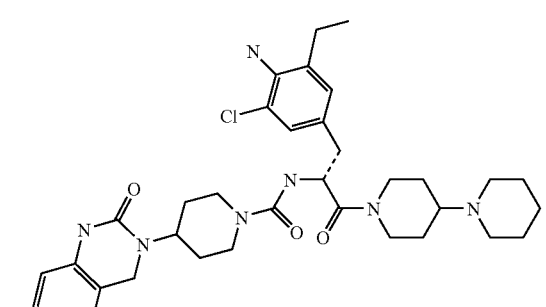
189
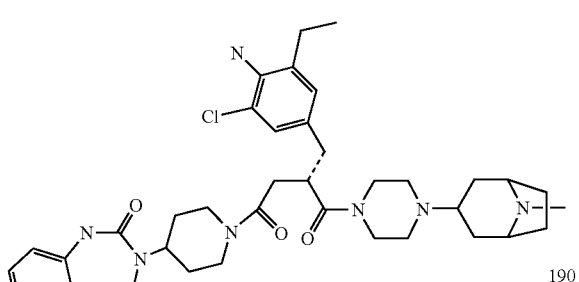
190
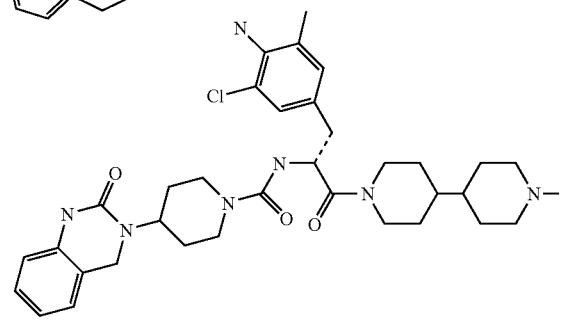

191
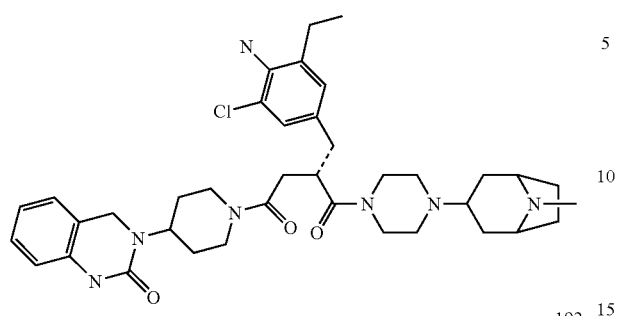
192
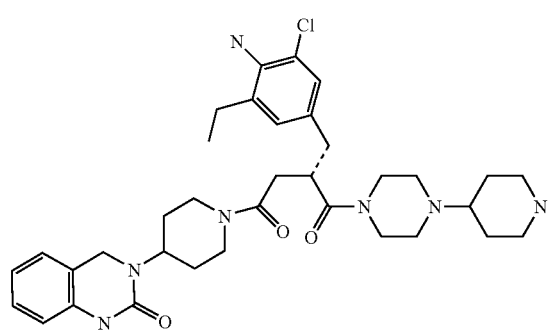
193
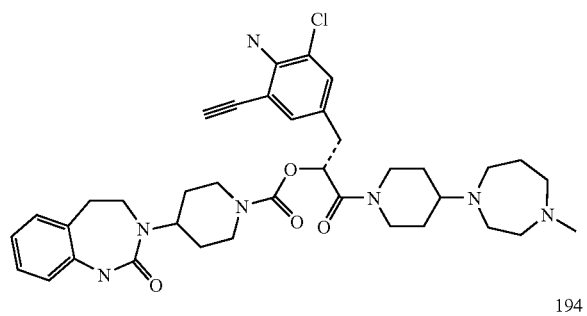
194
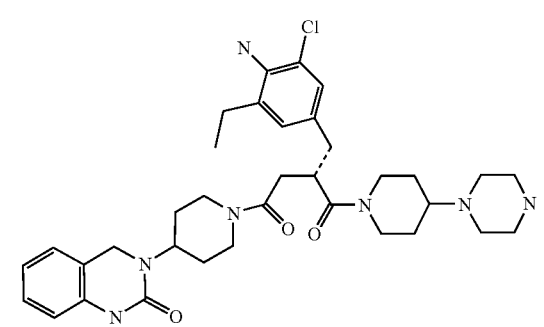
195
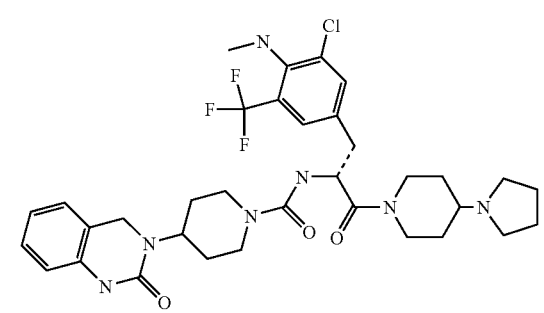
196
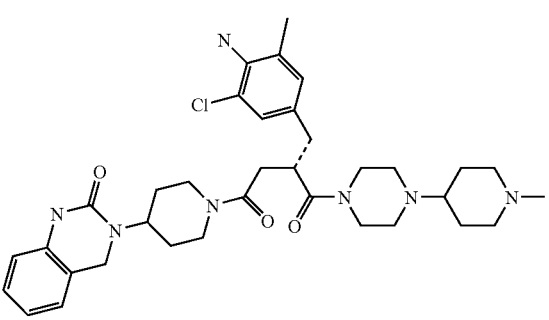
197
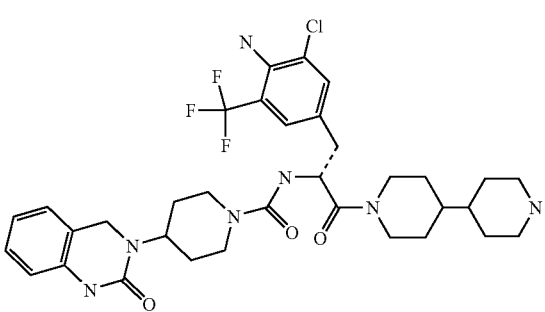
198
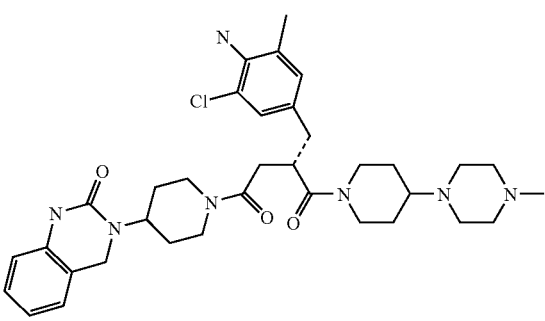
199
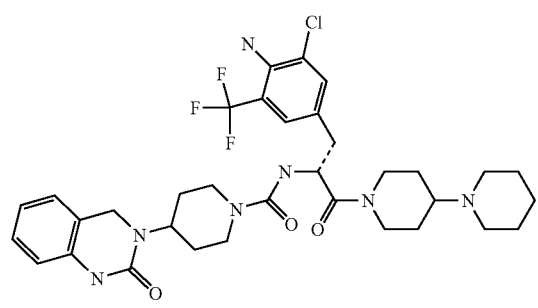
200
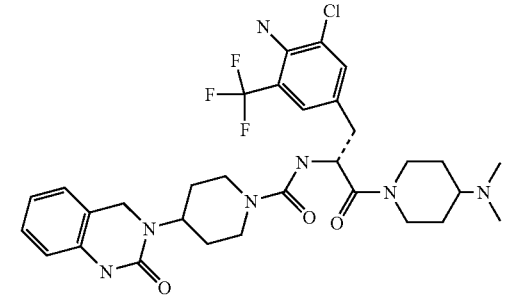

-continued

211 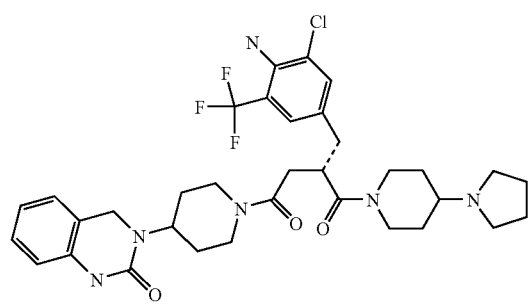
212 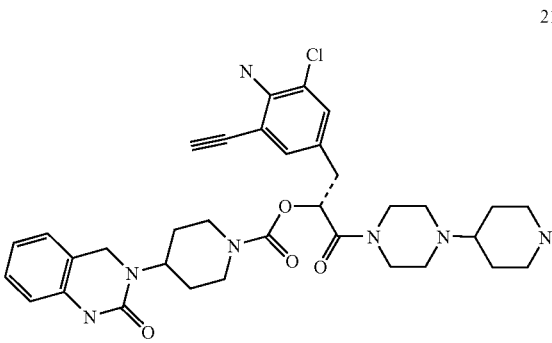
213 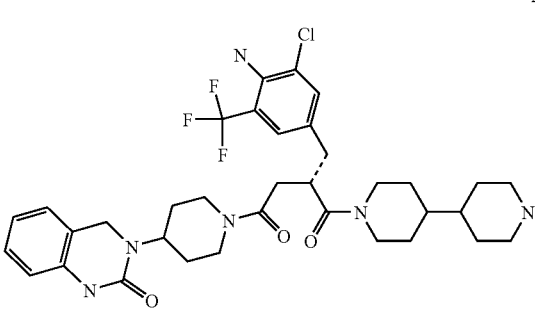
214 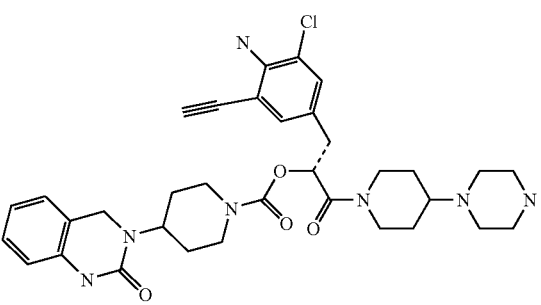
215 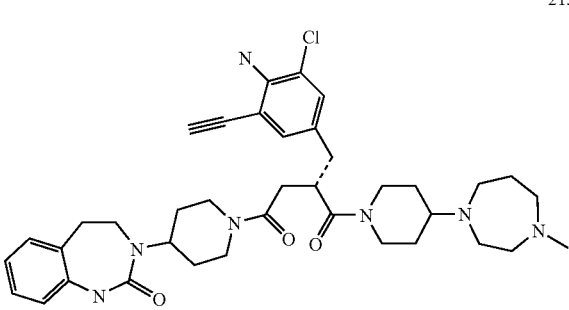
216 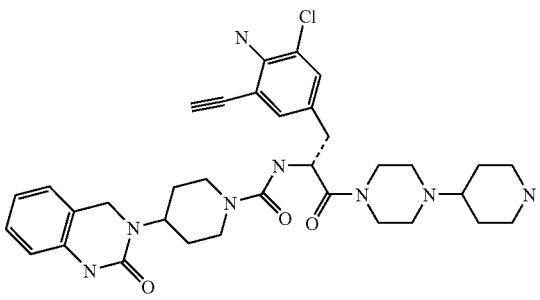
217 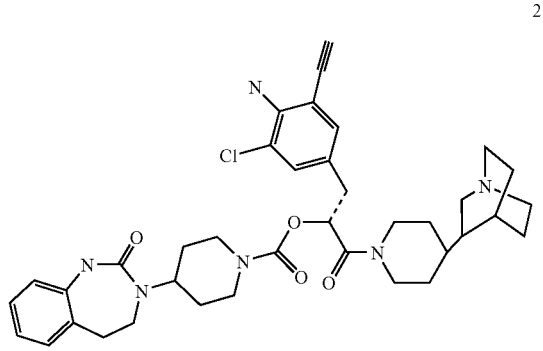
218 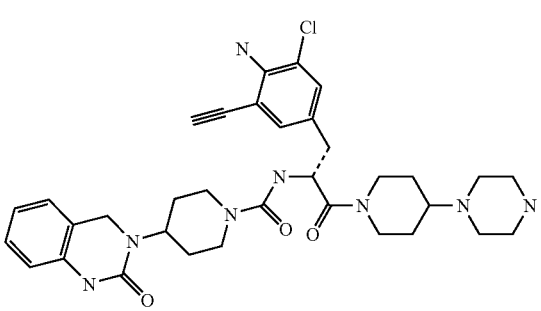
219 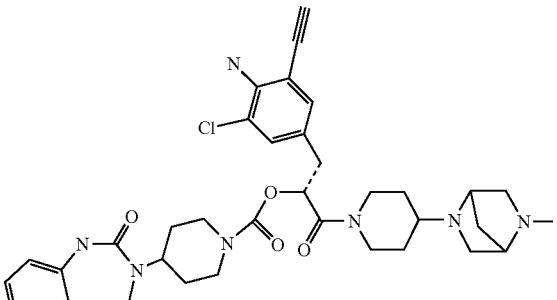
220 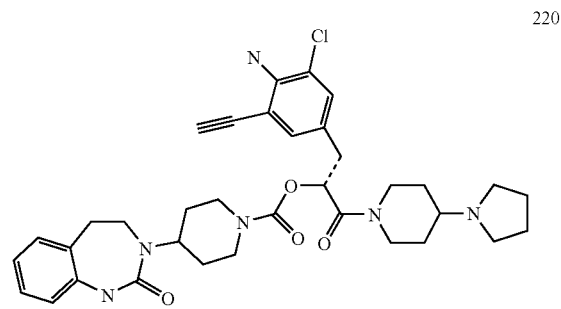

-continued

-continued
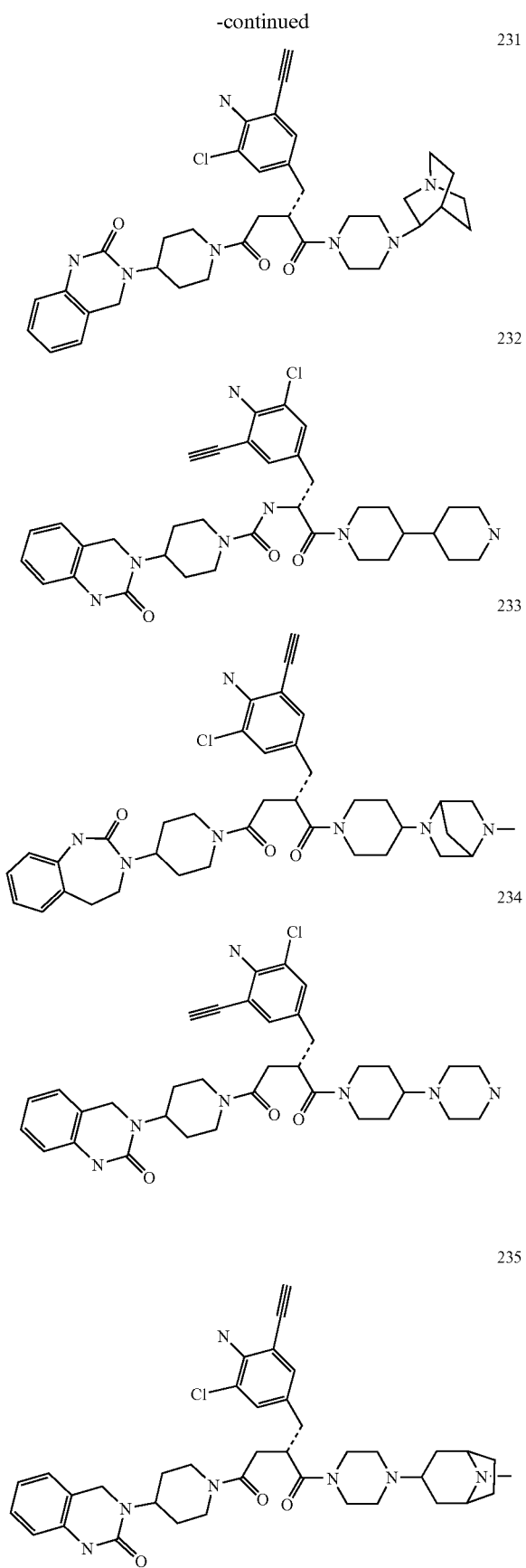
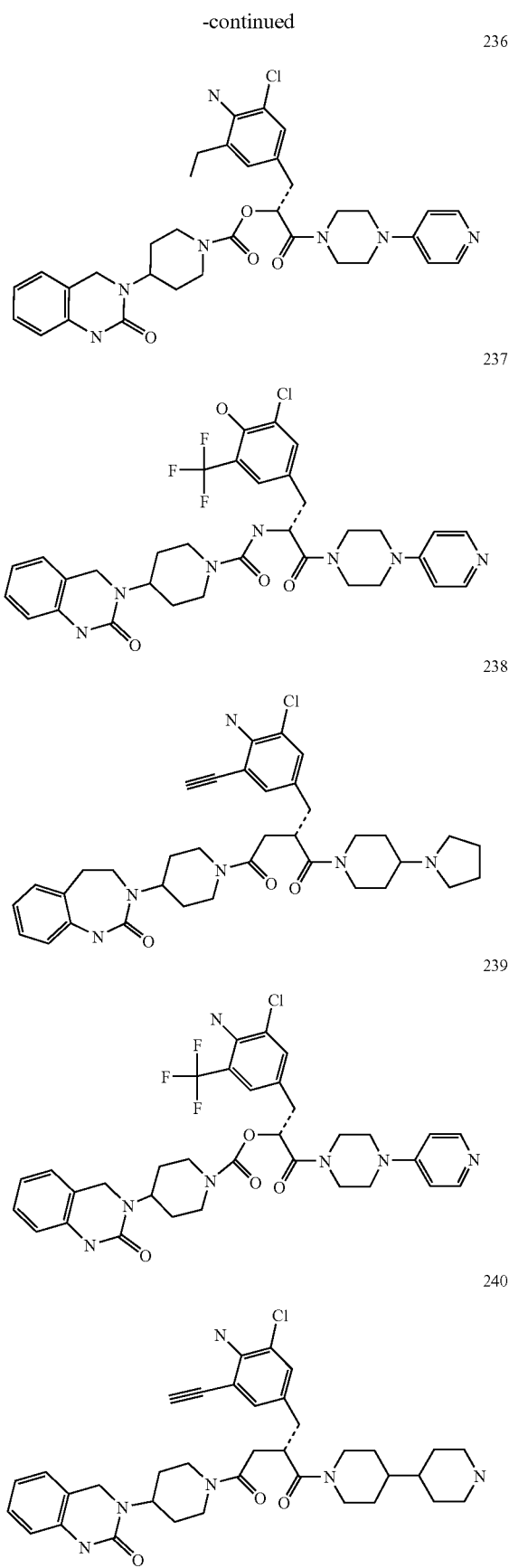

241
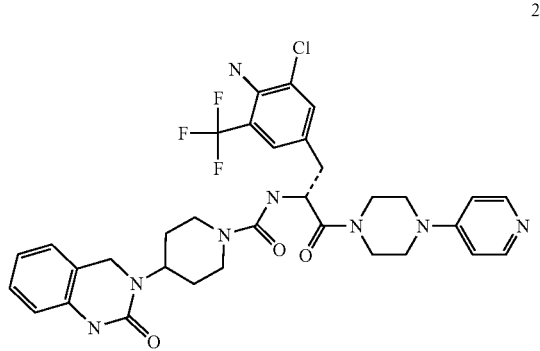
242
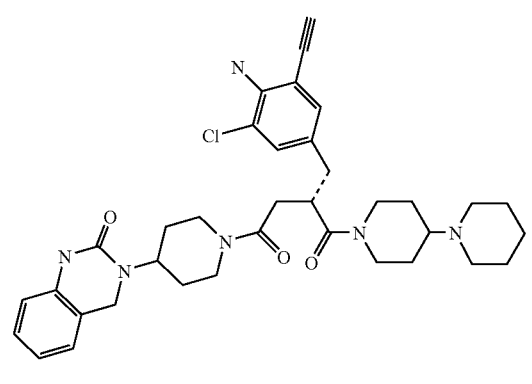
243
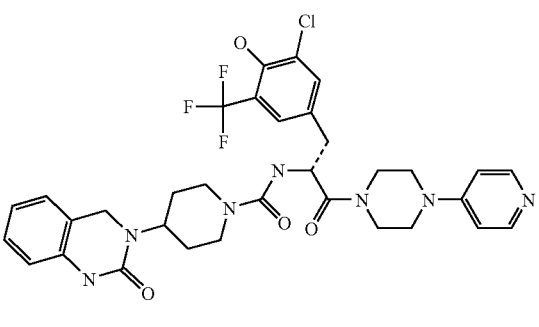
244
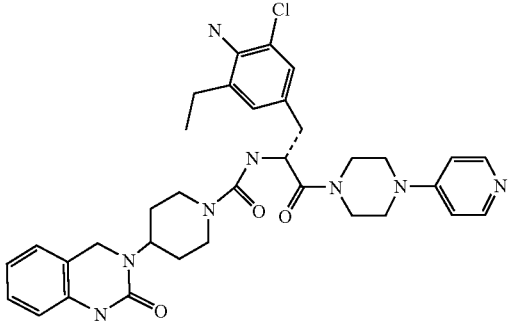
245
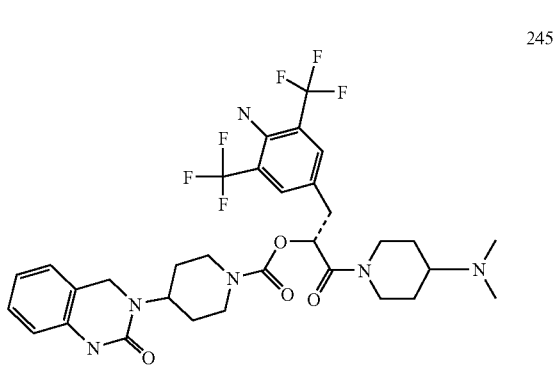
246
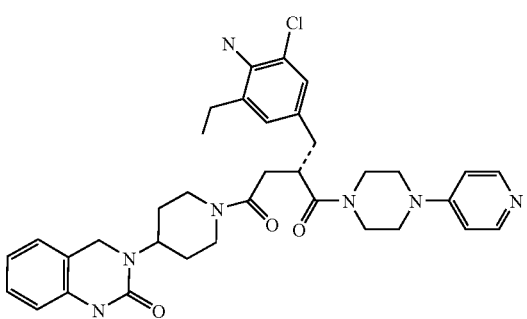
247
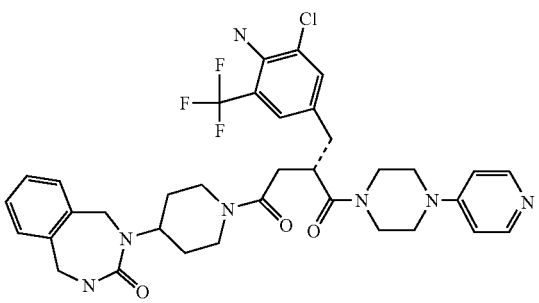
248
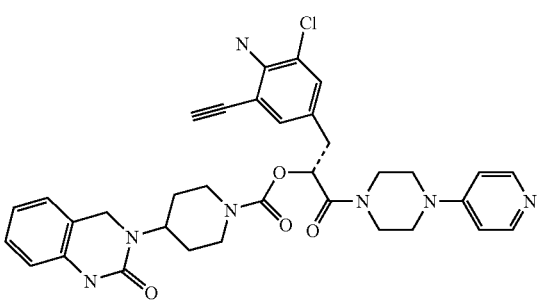

-continued
249
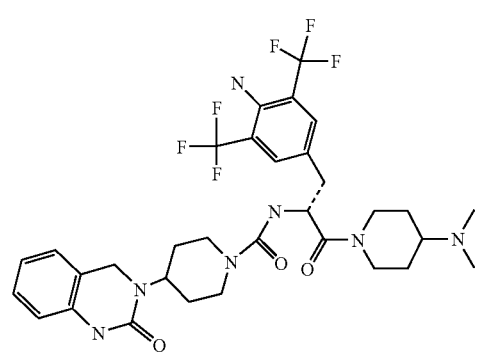
250
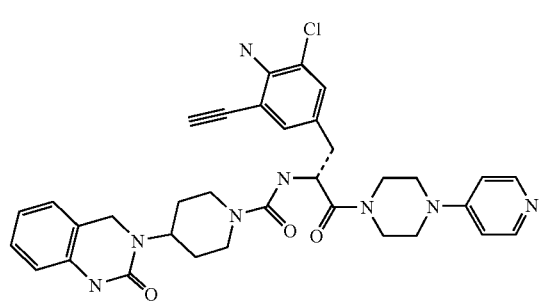
251
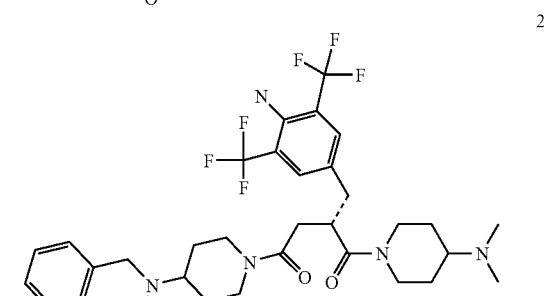
252
253
-continued
254
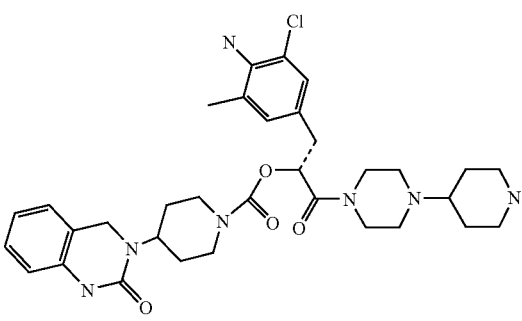
255
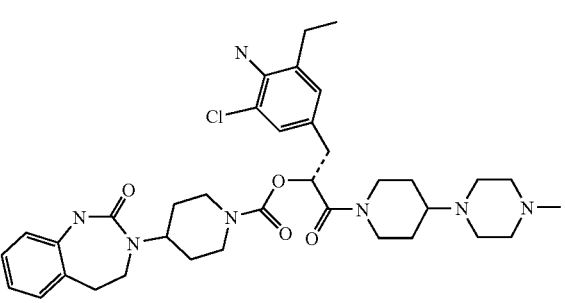
256
257
258

259
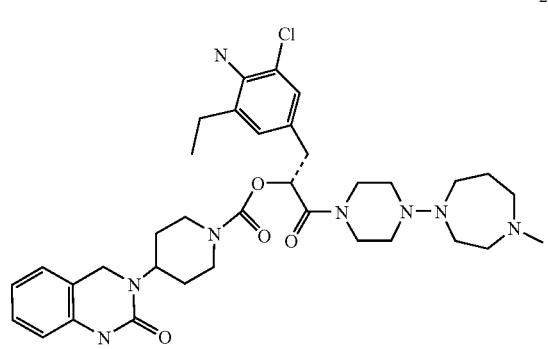
263
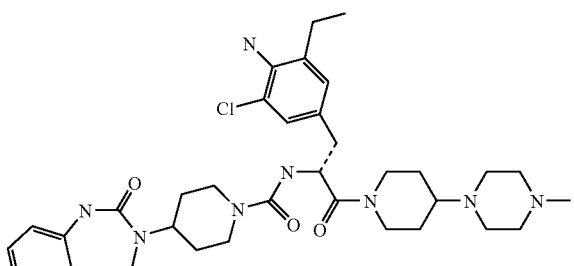
260
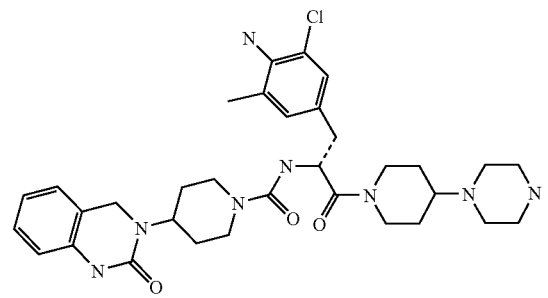
264
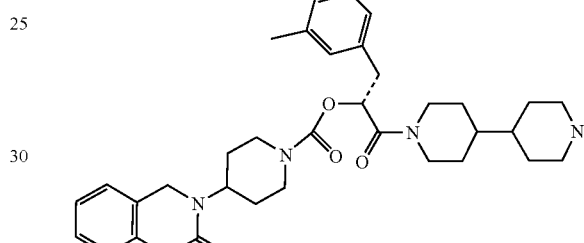
261
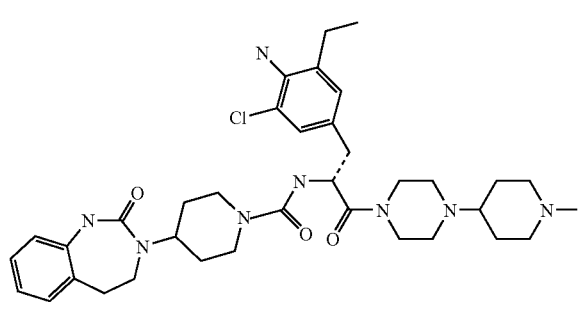
265
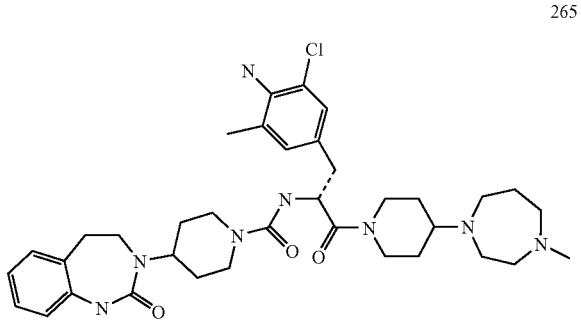
262
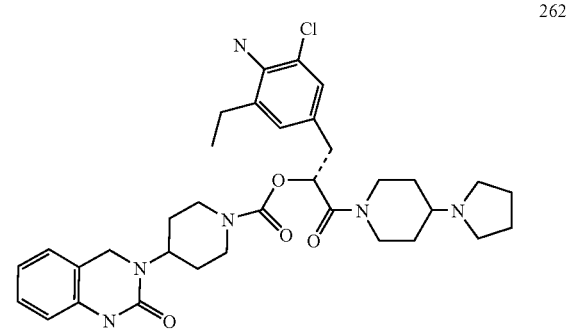
266
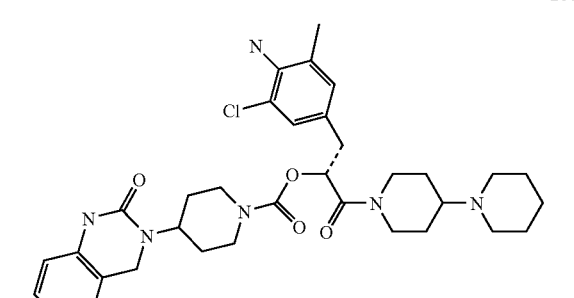

61
-continued
267
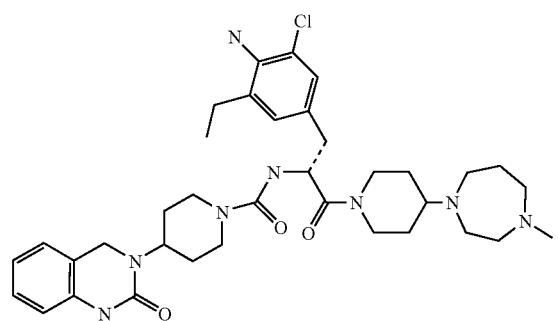
268
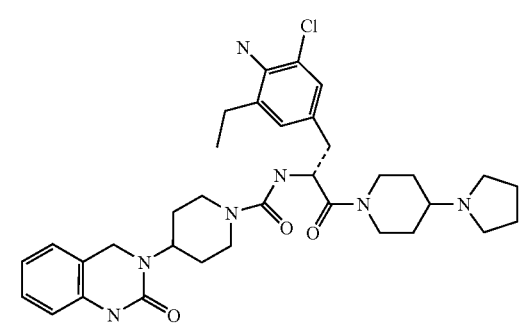
269
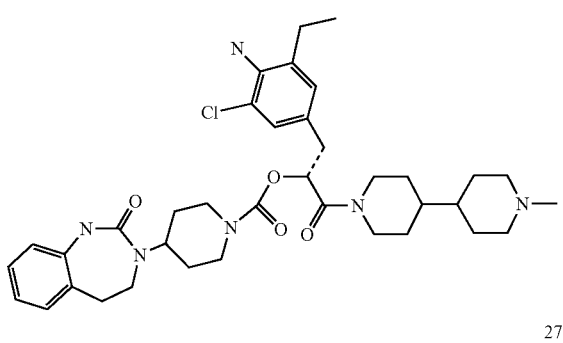
270
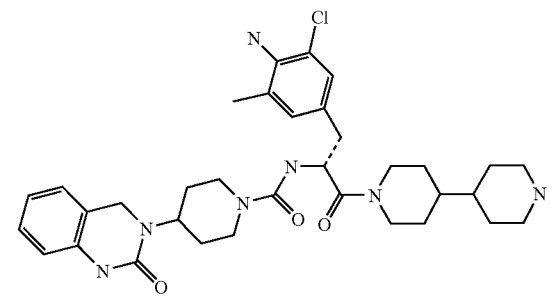
271
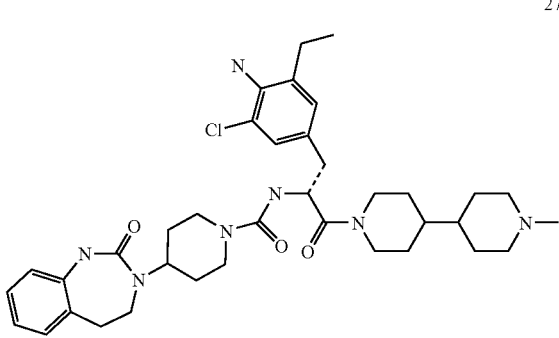
62
-continued
272
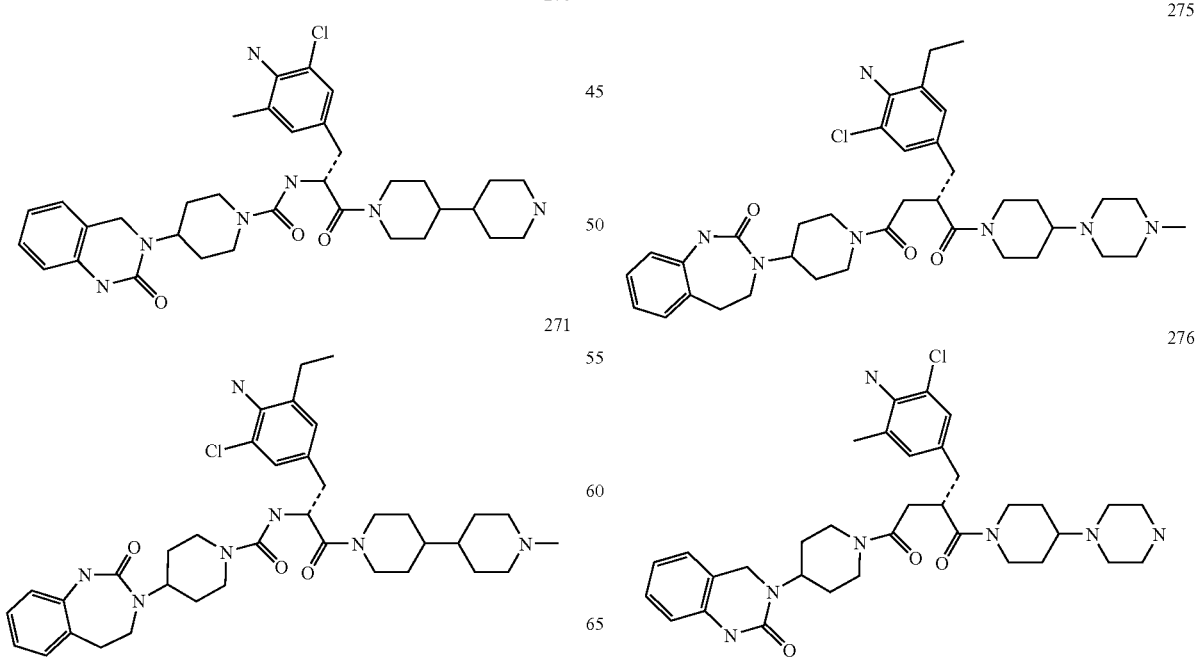
273
274
275
276

277
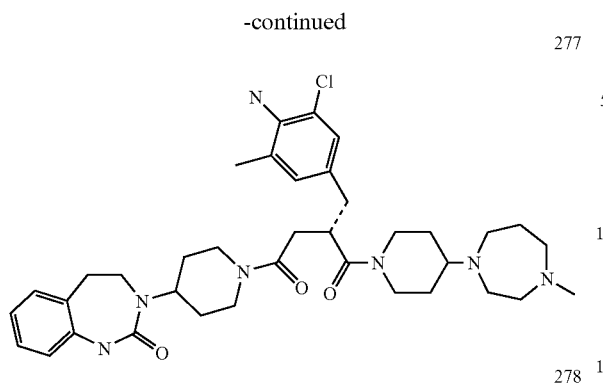
278
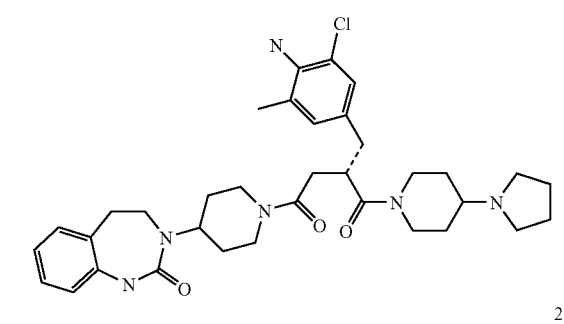
279
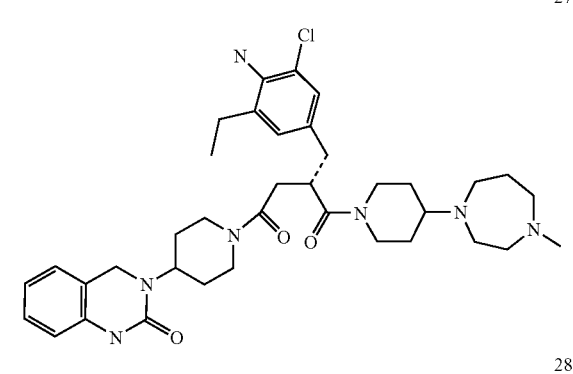
280
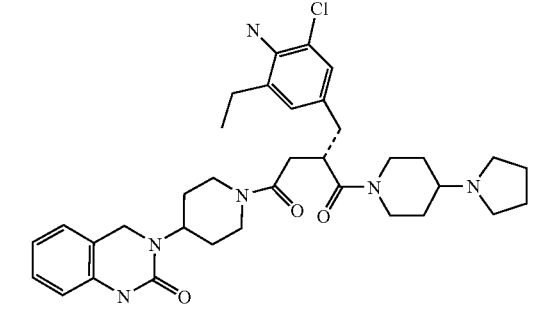
281
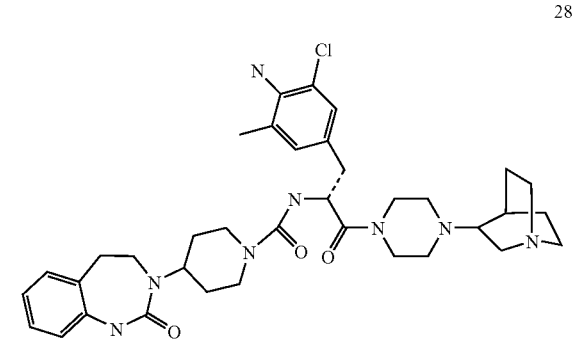
282
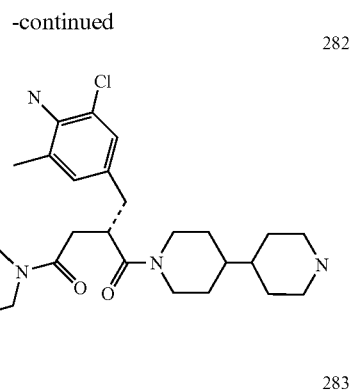
283
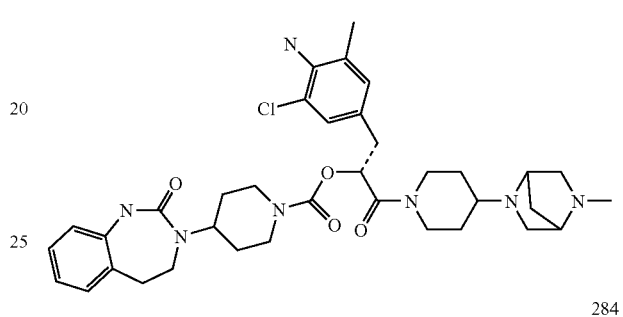
284
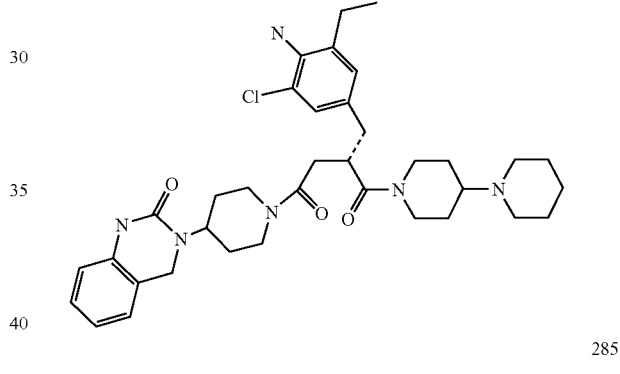
285
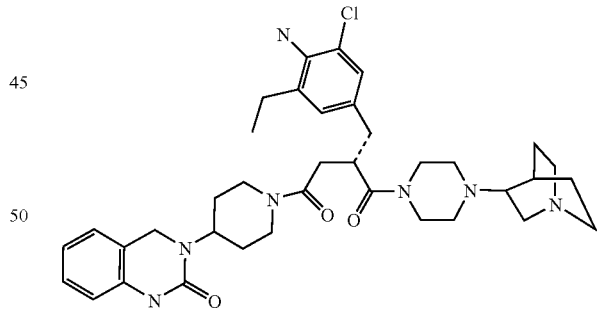
286
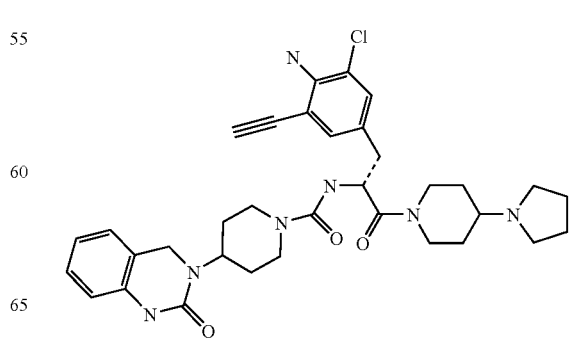

-continued
287
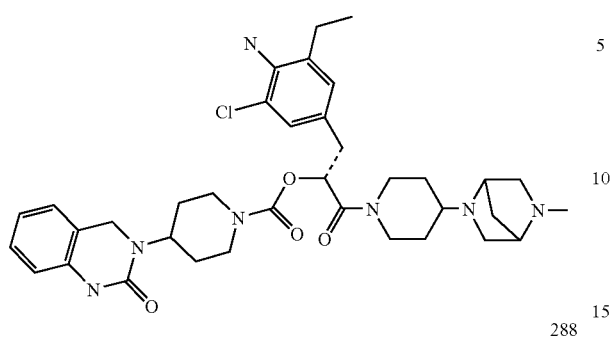
288
292
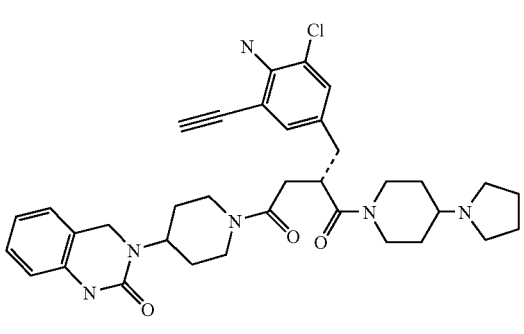
293
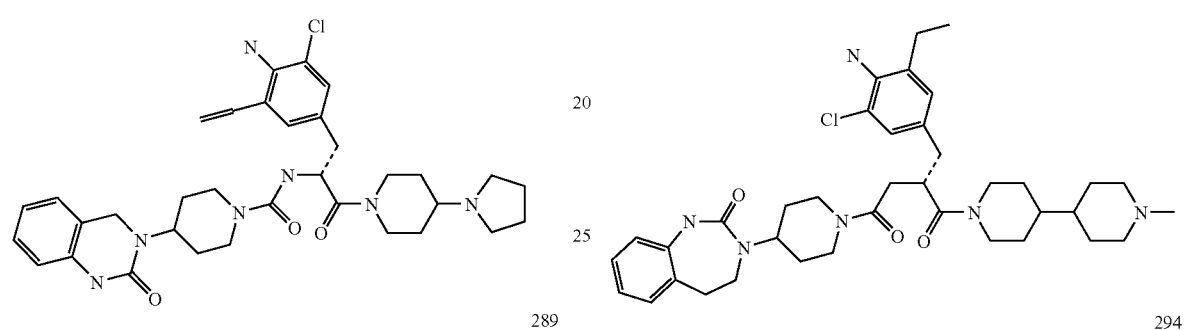
289
294
290
295
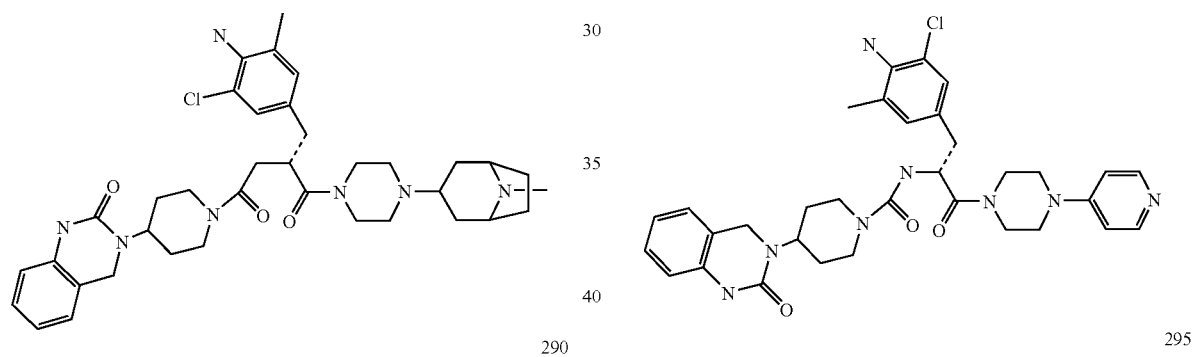
291
296
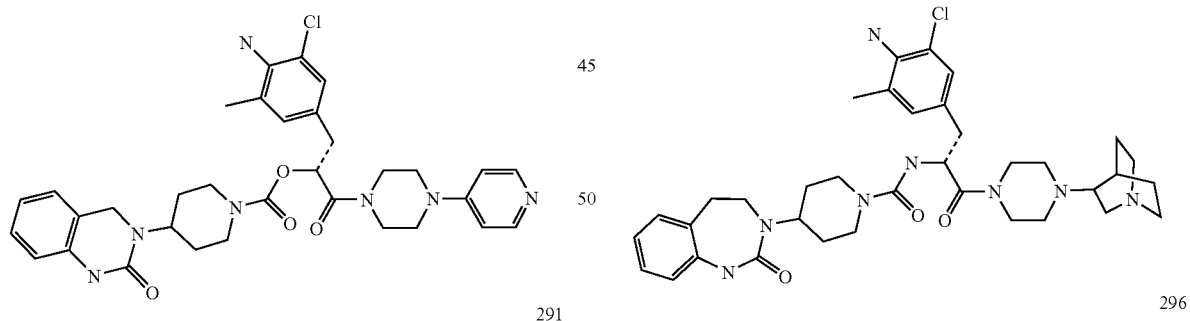
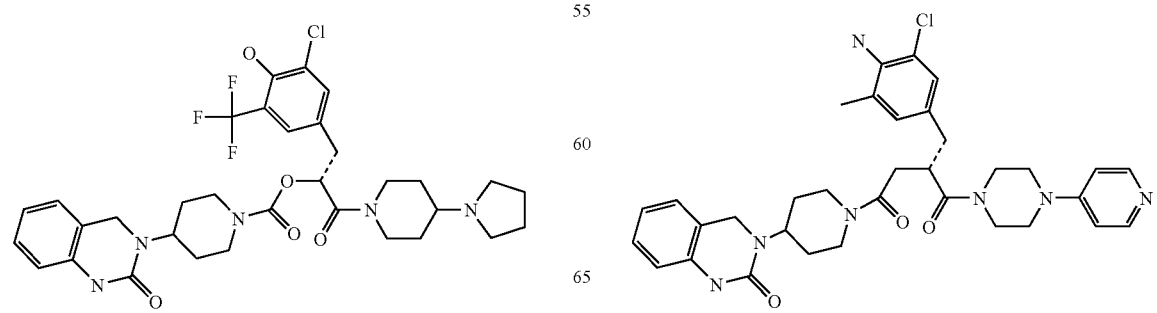

67
-continued
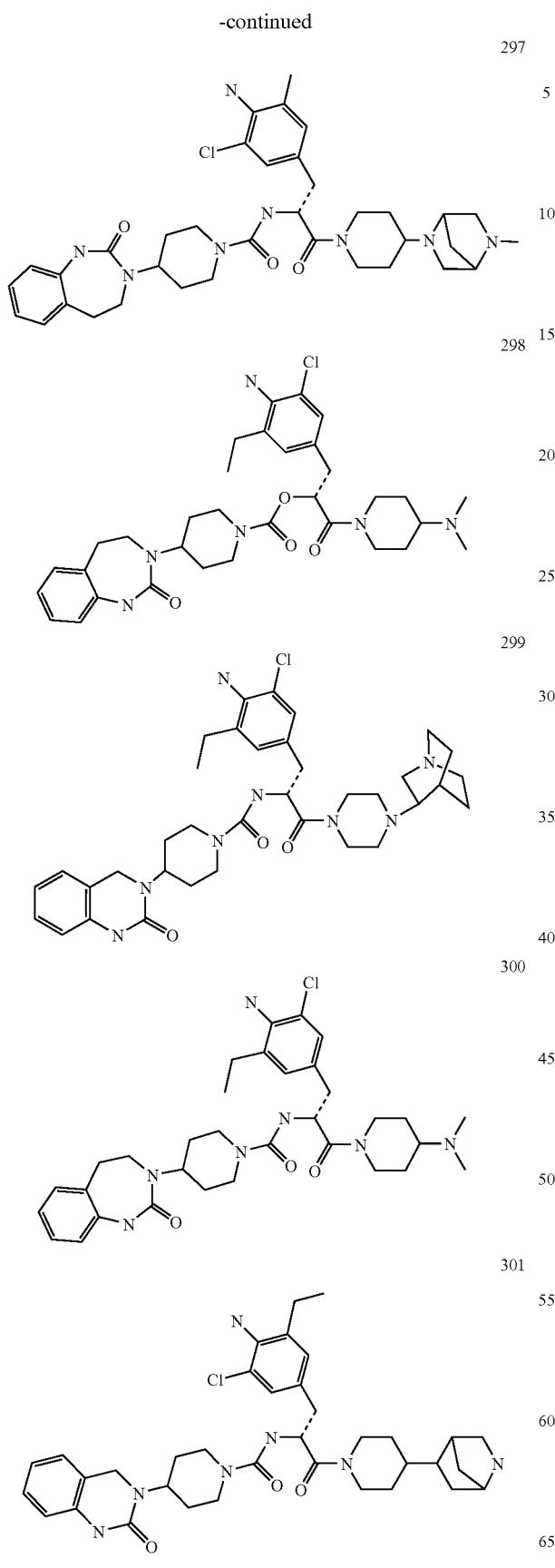
68
-continued
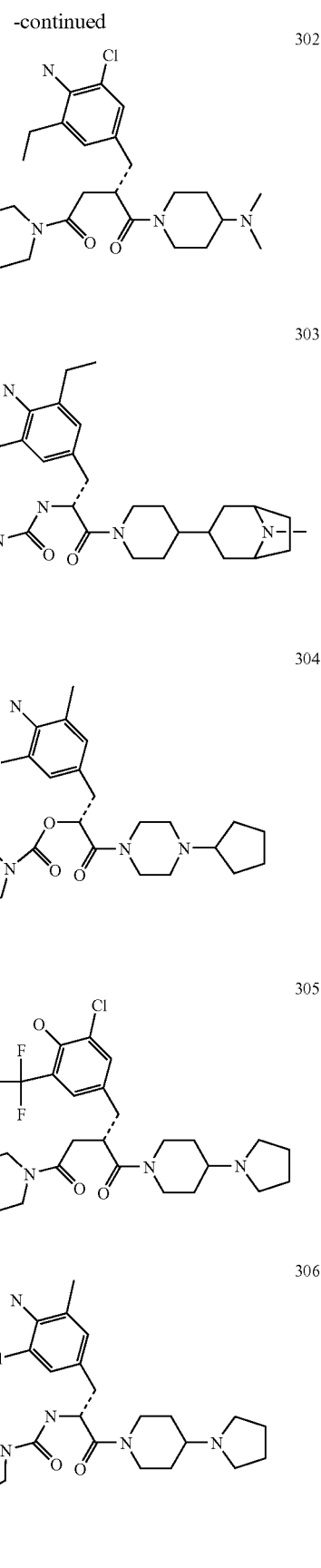

-continued
307
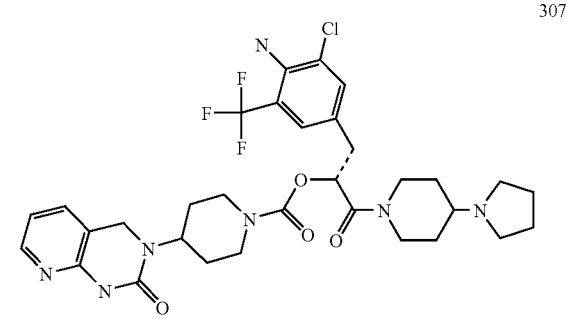
308
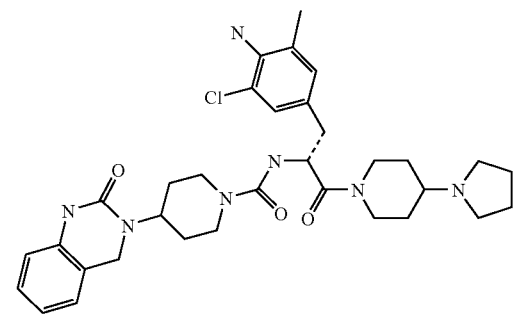
309
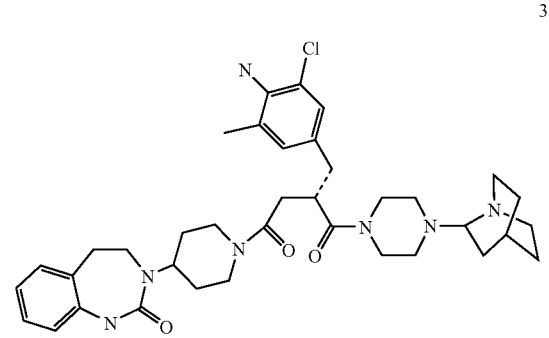
310
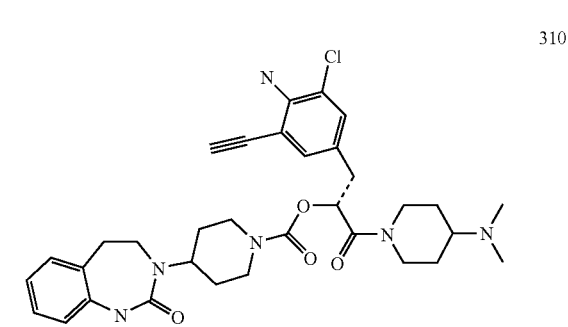
311
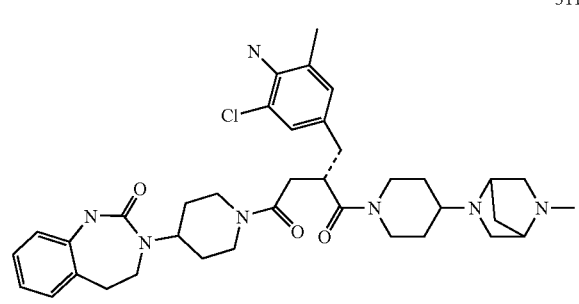
-continued
312
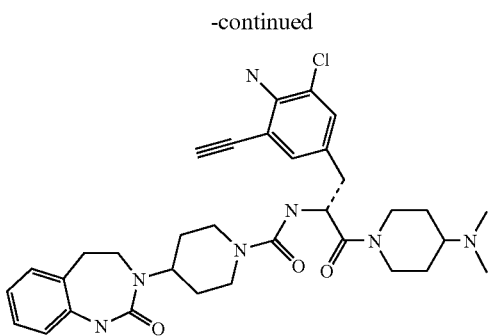
313
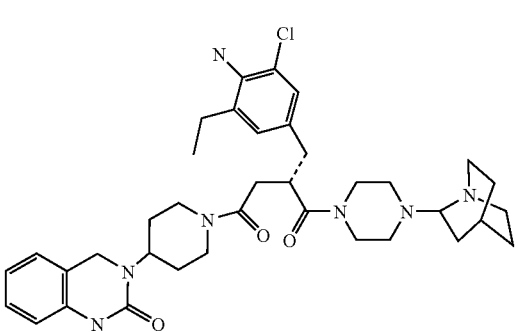
314
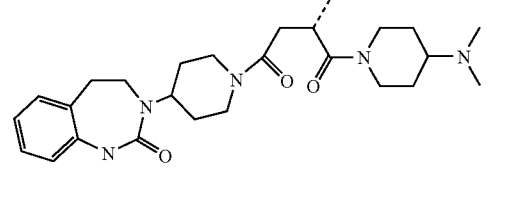
315
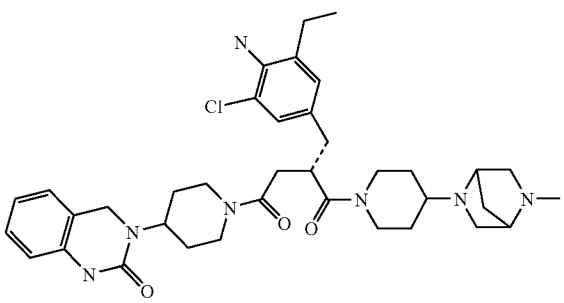
316
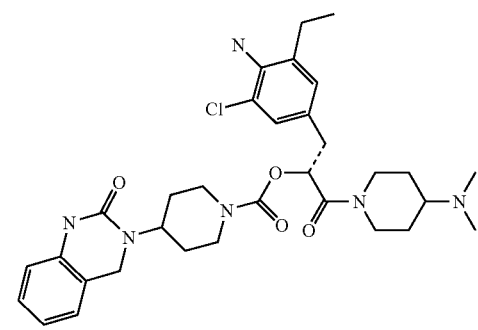

317
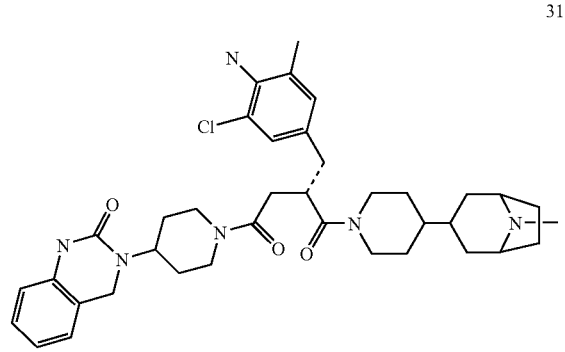
318
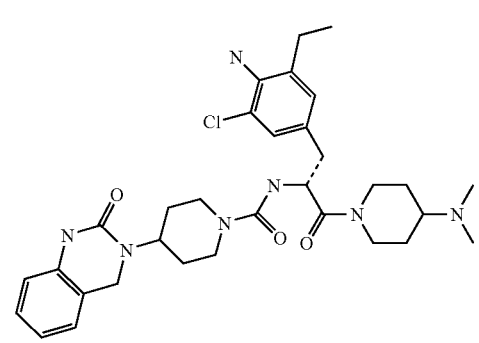
319
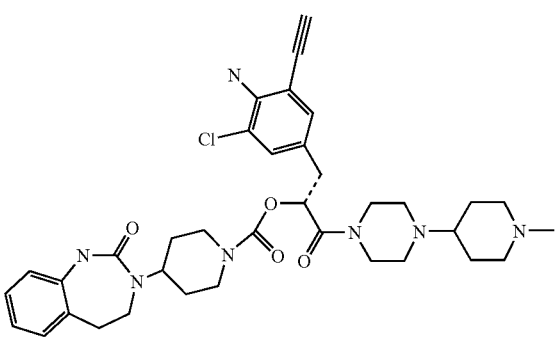
320
321
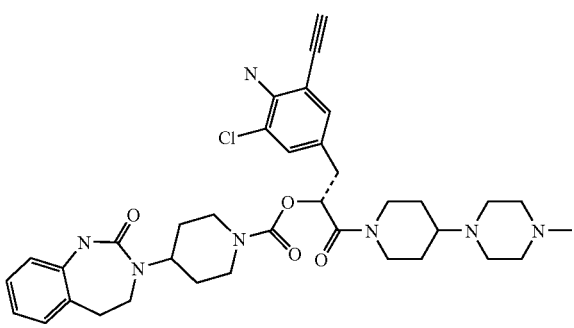
322
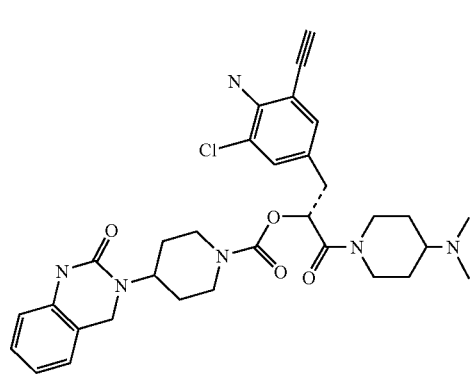
323
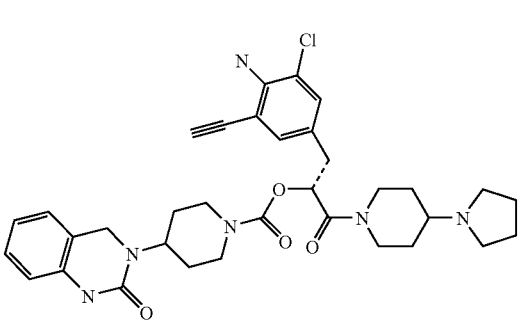
324
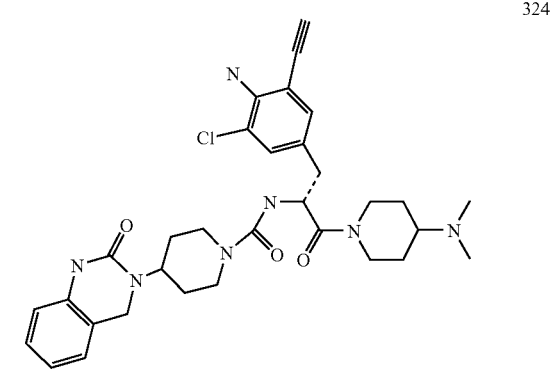

-continued
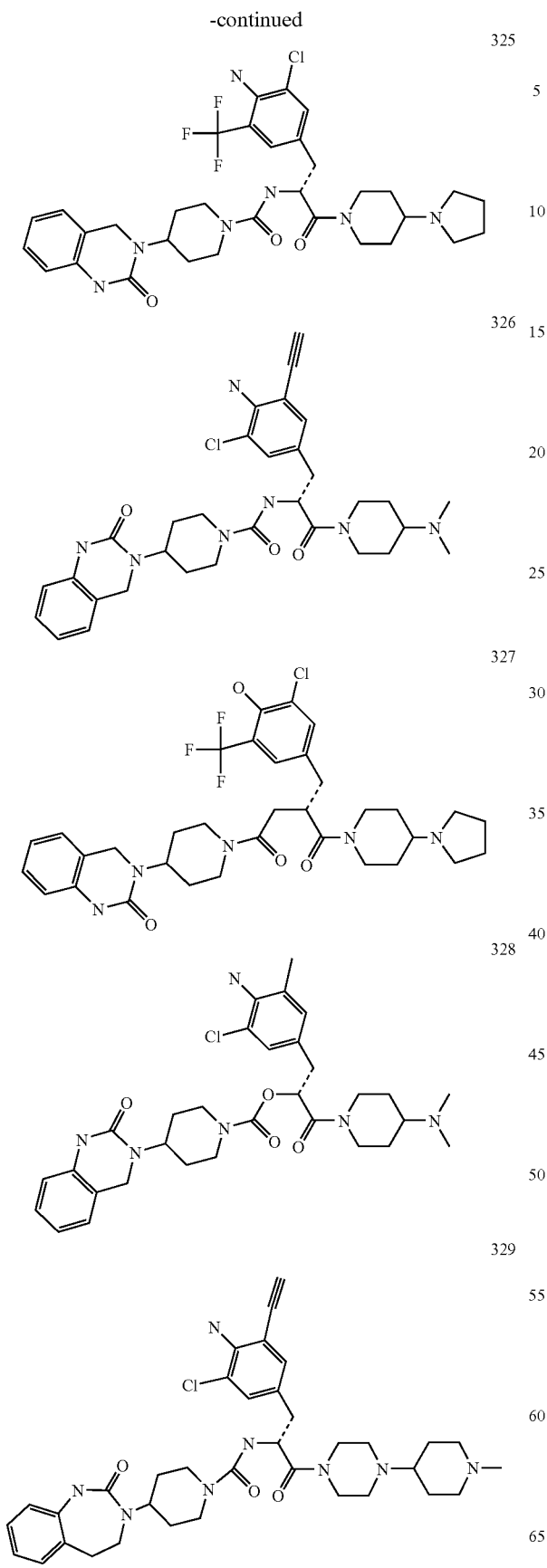
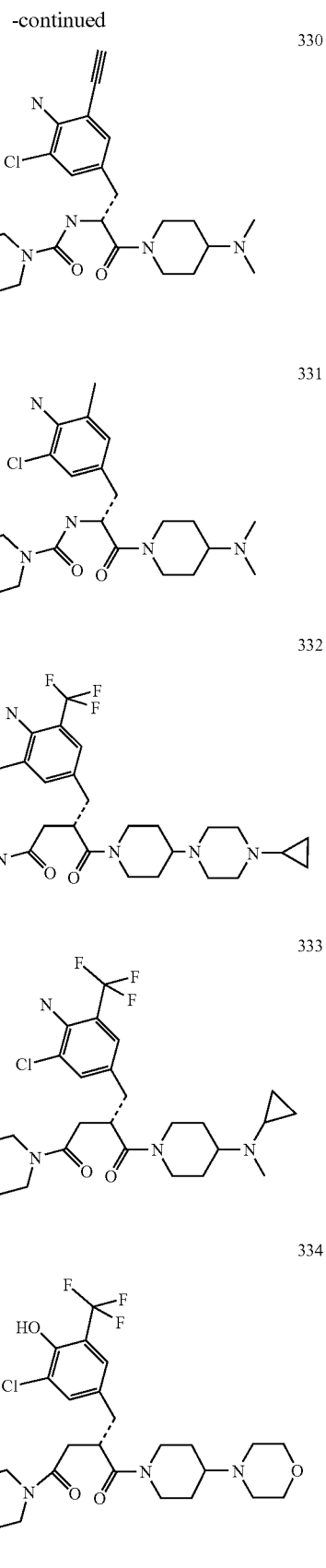

the tautomers, the diastereomers, the enantiomers, the hydrates thereof, the mixtures thereof and the salts thereof as well as the hydrates of the salts, while the compounds (1) (R)-1-(4-amino-3-chloro-5-trifluoromethyl-benzyl)-2-oxo-2-[4-(2-piperidin-1-yl-ethyl)-piperidin-1-yl]-ethyl 4-(2-oxo-1,2,4,5-tetrahydro-benzo[d][1,3]diazepin-3-yl)-piperidine-1-carboxylate, (2) (R)-1-(4-amino-3-chloro-5-trifluoromethyl-benzyl)-2-[4-(1-aza-bicyclo[2.2.2]oct-3-yl)-piperazin-1-yl]-2-oxo-ethyl 4-(2-oxo-1,2,4,5-tetrahydro-benzo[d][1,3]diazepin-3-yl)-piperidine-1-carboxylate, (3) (R)-1-(4-amino-3-chloro-5-trifluoromethyl-benzyl)-2-[4-(5-methyl-2,5-diaza-bicyclo[2.2.1]hept-2-yl)-piperidin-1-yl]-2-oxo-ethyl 4-(2-oxo-1,2,4,5-tetrahydro-benzo[d][1,3]diazepin-3-yl)-piperidine-1-carboxylate, (4) (R)-2-(4-amino-3-chloro-5-trifluoromethyl-phenyl)-1-(5-dimethylamino-pentylcarbamoyl)-ethyl 4-(2-oxo-1,2,4,5-tetrahydro-benzo[d][1,3]diazepin-3-yl)-piperidine-1-carboxylate, (5) (R)-1-(4-amino-3-chloro-5-trifluoromethyl-benzyl)-2-oxo-2-[4-((3R,5S)-3,4,5-trimethyl-piperazin-1-yl)-piperidin-1-yl]-ethyl 4-(2-oxo-1,2,4,5-tetrahydro-benzo[d][1,3]diazepin-3-yl)-piperidine-1-carboxylate, (6) (R)-1-(4-amino-3-chloro-5-trifluoromethyl-benzyl)-2-oxo-2-[4-(3,3,4,5,5-pentamethyl-piperazin-1-yl)-piperidin-1-yl]-ethyl 4-(2-oxo-1,2,4,5-tetrahydro-benzo[d][1,3]diazepin-3-yl)-piperidine-1-carboxylate, (7) (R)-1-(4-amino-3-chloro-5-trifluoromethyl-benzyl)-2-[4-(4-cyclopropyl-piperazin-1-yl)-piperidin-1-yl]-2-oxo-ethyl 4-(2-oxo-1,2,4,5-tetrahydro-benzo[d][1,3]diazepin-3-yl)-piperidine-1-carboxylate, (8) (R)-1-(4-amino-3-chloro-5-trifluoromethyl-benzyl)-2-[4-(1-methyl-piperidin-4-yl)-[1,4]diazepan-1-yl]-2-oxo-ethyl 4-(2-oxo-1,2,4,5-tetrahydro-benzo[d][1,3]diazepin-3-yl)-piperidine-1-carboxylate, (9) (R)-1-(4-amino-3-chloro-5-trifluoromethyl-benzyl)-2-(7-dimethylaminomethyl-1,2,4,5-tetrahydro-benzo[d]azepin-3-yl)-2-oxo-ethyl 4-(2-oxo-1,2,4,5-tetrahydro-benzo[d][1,3]diazepin-3-yl)-piperidine-1-carboxylate,

(10) (R)-1-(4-amino-3-chloro-5-trifluoromethyl-benzyl)-2-[4-(cyclopropyl-methyl-amino)-piperidin-1-yl]-2-oxo-ethyl 4-(2-oxo-1,2,4,5-tetrahydro-benzo[d][1,3]diazepin-3-yl)-piperidine-1-carboxylate,

(11) (R)-1-(4-amino-3-chloro-5-trifluoromethyl-benzyl)-2-[4-(hexahydro-pyrrolo[1,2-a]pyrazin-2-yl)-piperidin-1-yl]-2-oxo-ethyl 4-(2-oxo-1,2,4,5-tetrahydro-benzo[d][1,3]diazepin-3-yl)-piperidine-1-carboxylate,

(12) (R)-1-(4-amino-3-chloro-5-trifluoromethyl-benzyl)-2-[4-(1-ethyl-piperidin-4-yl)-piperazin-1-yl]-2-oxo-ethyl 4-(2-oxo-1,2,4,5-tetrahydro-benzo[d][1,3]diazepin-3-yl)-piperidine-1-carboxylate,

(13) (R)-1-(4-amino-3-chloro-5-trifluoromethyl-benzyl)-2-[4-(8-methyl-8-aza-bicyclo[3.2.1]oct-3-yl)-piperazin-1-yl]-2-oxo-ethyl 4-(2-oxo-1,2,4,5-tetrahydro-benzo[d][1,3]diazepin-3-yl)-piperidine-1-carboxylate,

(14) (R)-1-(4-amino-3-chloro-5-trifluoromethyl-benzyl)-2-[4-(4-methyl-[1,4]diazepan-1-yl)-piperidin-1-yl]-2-oxo-ethyl 4-(2-oxo-1,2,4,5-tetrahydro-benzo[d][1,3]diazepin-3-yl)-piperidine-1-carboxylate,

(15) (R)-1-(4-amino-3-chloro-5-trifluoromethyl-benzyl)-2-(4-cyclopropylmethyl-piperazin-1-yl)-2-oxo-ethyl 4-(2-oxo-1,2,4,5-tetrahydro-benzo[d][1,3]diazepin-3-yl)-piperidine-1-carboxylate,

(16) (R)-1-(4-amino-3-chloro-5-trifluoromethyl-benzyl)-2-(4-azepan-1-yl-piperidin-1-yl)-2-oxo-ethyl 4-(2-oxo-1,2,4,5-tetrahydro-benzo[d][1,3]diazepin-3-yl)-piperidine-1-carboxylate,

(17) (R)-1-(4-amino-3-chloro-5-trifluoromethyl-benzyl)-2-(4-morpholin-4-yl-piperidin-1-yl)-2-oxo-ethyl 4-(2-oxo-1,2,4,5-tetrahydro-benzo[d][1,3]diazepin-3-yl)-piperidine-1 carboxylate,

(18) (R)-1-(4-amino-3-chloro-5-trifluoromethyl-benzyl)-2-(4-imidazol-1-yl-piperidin-1-yl)-2-oxo-ethyl 4-(2-oxo-1,2,4,5-tetrahydro-benzo[d][1,3]diazepin-3-yl)-piperidine-1-carboxylate,

(19) 4-(2-oxo-1,2,4,5-tetrahydro-benzo[d][1,3]diazepin-3-yl)-piperidine-1-carboxylic acid-{(R)-1-(4-amino-3-chloro-5-trifluoromethyl-benzyl)-2-[4-(4-cyclopropyl-piperazin-1-yl)-piperidin-1-yl]-2-oxo-ethyl}-amide,

(20) (R)-1-(4-chloro-3-trifluoromethyl-benzyl)-2-[4-(4-methyl-piperazin-1-yl)-piperidin-1-yl]-2-oxo-ethyl 4-(2-oxo-1,2,4,5-tetrahydro-benzo[d][1,3]diazepin-3-yl)-piperidine-1-carboxylate,

(21) (R)-1-(4-chloro-3-trifluoromethyl-benzyl)-2-[4-(1-methyl-piperidin-4-yl)-piperazin-1-yl]-2-oxo-ethyl 4-(2-oxo-1,2,4,5-tetrahydro-benzo[d][1,3]diazepin-3-yl)-piperidine-1-carboxylate,

(22) 4-(2-oxo-1,2,4,5-tetrahydro-benzo[d][1,3]diazepin-3-yl)-piperidine-1-carboxylic acid-[(R)-1-(4-amino-3-chloro-5-methyl-benzyl)-2-(4-cyclopropyl-piperazin-1-yl)-2-oxo-ethyl]-amide,

(23) 4-(2-oxo-1,2,4,5-tetrahydro-benzo[d][1,3]diazepin-3-yl)-piperidine-1-carboxylic acid-[(R)-1-(4-amino-3-chloro-5-methyl-benzyl)-2-(4-isopropyl-piperazin-1-yl)-2-oxo-ethyl]-amide,

(24) 4-(2-oxo-1,2,4,5-tetrahydro-benzo[d][1,3]diazepin-3-yl)-piperidine-1-carboxylic acid-{(R)-1-(4-amino-3-chloro-5-ethynyl-benzyl)-2-[4-(4-methyl-piperazin-1-yl)-piperidin-1-yl]-2-oxo-ethyl}-amide,

(25) 4-(2-oxo-1,2,4,5-tetrahydro-benzo[d][1,3]diazepin-3-yl)-piperidine-1-carboxylic acid-{(R)-1-(4-amino-3-chloro-5-ethyl-benzyl)-2-[4-(4-methyl-piperazin-1-yl)-piperidin-1-yl]-2-oxo-ethyl}-amide,

(26) (S)-2-(4-amino-3-chloro-5-trifluoromethyl-benzyl)-1-[4-(4-cyclopropyl-piperazin-1-yl)-piperidin-1-yl]-4-[4-(2-oxo-1,2,4,5-tetrahydro-benzo[d][1,3]diazepin-3-yl)-piperidin-1-yl]-butane-1,4-dione,

(27) (S)-2-(4-amino-3-chloro-5-trifluoromethyl-benzyl)-1-[4-(cyclopropyl-methyl-amino)-piperidin-1-yl]-4-[4-(2-oxo-1,2,4,5-tetrahydro-benzo[d][1,3]diazepin-3-yl)-piperidin-1-yl]-butan-1,4-dione,

(28) (S)-2-(3-chloro-4-hydroxy-5-trifluoromethyl-benzyl)-1-(4-morpholin-4-yl-piperidin-1-yl)-4-[4-(2-oxo-1,2,4,5-tetrahydro-benzo[d][1,3]diazepin-3-yl)-piperidin-1-yl]-butane-1,4-dione, the tautomers, the diastereomers, the enantiomers, the hydrates thereof, the mixtures thereof and the salts thereof as well as the hydrates of the salts are of exceptional importance.

The compounds of general formula (I) are prepared by methods known in principle. The following methods have proved particularly useful for preparing the compounds of general formula (I) according to the invention:

(a) In order to prepare compounds of general formula

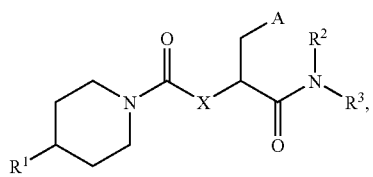

wherein X denotes the oxygen atom or the NH group and A and R¹ to R³ are as hereinbefore defined:

reacting a piperidine of general formula

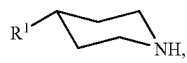

wherein R¹ is as hereinbefore defined,
(i) with a carbonic acid derivative of general formula

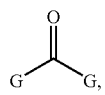

wherein G denotes a nucleofugic group which may be identical or different, preferably the phenoxy, 1H-imidazol-1-yl, 1H-1,2,4-triazol-1-yl, trichloromethoxy or 2,5-dioxopyrrolidin-1-yloxy group, with the proviso that X denotes the NH group, or
(ii) with a carbonic acid derivative of general formula

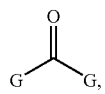

wherein G denotes a nucleofugic group which may be identical or different, preferably the chlorine atom, the p-nitrophenoxy or trichloromethoxy group, with the proviso that X denotes the oxygen atom, and with a compound of general formula

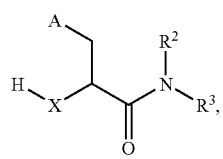

wherein X denotes the oxygen atom or a —NH— group and A, R² and R³ are as hereinbefore defined, with the proviso that R² and R³ do not contain any other free, unprotected, primary or secondary aliphatic amino function.

Any primary or secondary amino function additionally present in the group —NR²R³ is in each case provided with a suitable protective group.

The reactions which are theoretically two-step reactions are usually carried out as one-pot processes, preferably by reacting one of the two components (III) or (V) with equimolar quantities of the carbonic acid derivative of general formula (IV) in a suitable solvent at lower temperature in the first stage, then adding at least equimolar amounts of the other component (III) or (V) and finishing the reaction at elevated temperature. The reactions with bis-(trichloromethyl)-carbonate are preferably carried out in the presence of at least 2 equivalents (based on bis-(trichloromethyl)-carbonate) of a tertiary base, e.g. triethylamine, N-ethyl-diisopropylamine, pyridine, 1,5-diazabicyclo[4.3.0]non-5-ene, 1,4-diazabicyclo[2.2.2]octane or 1,8-diazabicyclo[5.4.0]undec-7-ene. Examples of solvents, which should be anhydrous, include tetrahydrofuran, dioxane, dimethyl formamide, dimethylacetamide, N-methyl-2-pyrrolidone, 1,3-dimethyl-2-imidazolidinone or acetonitrile; if bis-(trichloromethyl)-carbonate is used as the carbonyl component anhydrous chlorohydrocarbons such as dichloromethane, 1,2-dichloroethane or trichloroethylene are preferred. The reaction temperatures for the first reaction step are between −30 and +25° C., preferably −5 and +10° C., for the second reaction step they are between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Präparativen Organischen Chemie, Vol. V, p. 53-93, Verlag Chemie, Weinheim/Bergstr., 1967; P. Majer and R. S. Randad, J. Org. Chem. 59, 1937-1938 (1994); K. Takeda, Y. Akagi, A. Saiki, T. Sukahara and H. Ogura, Tetrahedron Letters 24 (42), 4569-4572 (1983); S. R. Sandler and W. Karo in "Organic Functional Group Preparations", Vol. II, p. 223-245, Academis Press, New York 1971).

(b) In order to prepare compounds of general formula

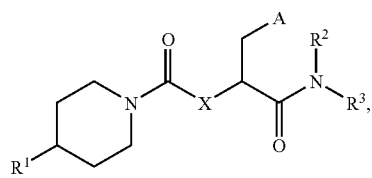

wherein X denotes the methylene group and A and R¹ to R³ are as hereinbefore defined, with the proviso that no other free unprotected primary or secondary aliphatic amino functions are present:

coupling a carboxylic acid of general formula

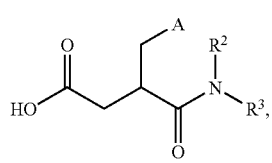

wherein A, R² and R³ are as hereinbefore defined, with a piperidine of general formula

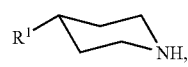

wherein R¹ is as hereinbefore defined.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride of the carboxylic acid of general formula (VI) which is to be coupled and monoisobutyl carbonate is obtained, using isobutyl chlorocarbonate in the presence of bases such as 4-methylmorpholine or 4-ethylmorpholine. The preparation of this mixed anhydride and the coupling with amines are carried out in a one-pot process, using the above-mentioned solvents and at temperatures between −20 and +25° C., preferably 0° C. and +25° C.

(c) In order to prepare compounds of general formula

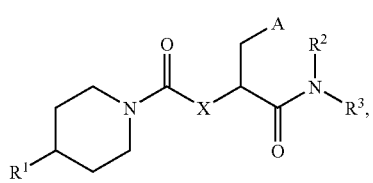

wherein X denotes the methylene group and A and R¹ to R³ are as hereinbefore defined, with the proviso that diese groups do not contain any free unprotected primary or secondary amine:

coupling a compound of general formula

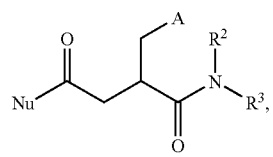

wherein A, R² and R³ are as hereinbefore defined, with the proviso that R² and R³ do not contain any free unprotected primary or secondary amine, and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, while the substitutents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group, with a piperidine of general formula

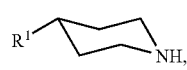

wherein R¹ is as hereinbefore defined.

The reaction is carried out under Schotten-Baumann or Einhom conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2.2.2]octane or 1,8-diazabicyclo[5.4.0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

(d) In order to prepare compounds of general formula

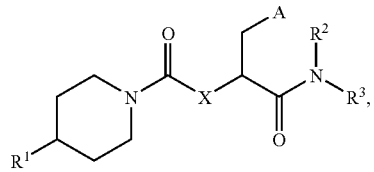

wherein A, X and R¹ to R³ are as hereinbefore defined:

coupling a carboxylic acid of general formula

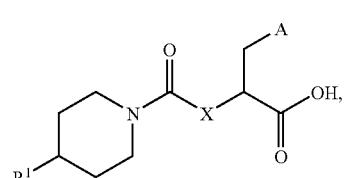

wherein A, X and R¹ are as hereinbefore defined, with an amine of general formula HNR²R³, wherein R² and R³ are as hereinbefore defined, with the proviso that they do not contain any other free unprotected primary or secondary aliphatic amino function.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N' N¹-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58-59; M. Bodanszky, "Principles of Peptide Synthesis", Springer-Verlag 1984, p. 21-27). The Vaughan variant of the mixed anhydride process is preferred (J. R. Vaughan Jr., J. Amer. Chem. Soc. 73, 3547 (1951)), in which the mixed anhydride is obtained from the carboxylic acid of general formula (VIII) which is to be coupled and monoisobutyl carbonate, using isobutyl chlorocarbonate in the presence of bases such as 4-methylmorpholine or 4-ethylmorpholine. The preparation of this mixed anhydride and the coupling with the amines of general formula HNR²R³ are carried out in a one-pot process, using the above-mentioned solvents and at temperatures between −20 and +25° C., preferably 0° C. and +25° C.

(e) In order to prepare compounds of general formula (I)

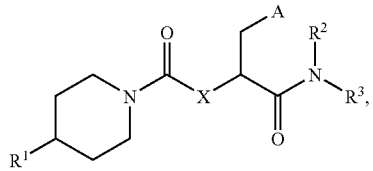

wherein A, X and R¹ to R³ are as hereinbefore defined, with the proviso that no free unprotected primary or secondary amine is present:

coupling a compound of general formula (IX)

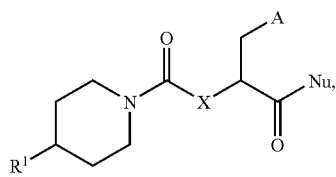

wherein A, X and R¹ are as hereinbefore defined and Nu denotes a leaving group, for example a halogen atom, such as the chlorine, bromine or iodine atom, an alkyl-sulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, while the substitutents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group, with an amine of general formula HNR²R³, wherein R² and R³ are as hereinbefore defined, with the proviso that no other free unprotected primary or secondary aliphatic amino function is present.

The reaction is carried out under Schotten-Baumann or Einhom conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2.2.2] octane or 1,8-diazabicyclo[5.4.0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula (I) according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The starting compounds of general formula (III), if they are not known from the literature or commercially available, are obtained using the processes described in International Patent Application WO 98/11128 and DE 199 52 146. The starting compounds of general formula (IV) are commercially available. Compounds of general formula (V) may be obtained by methods familiar to the peptide chemist from protected phenylalanines and amines of general formula $HNR^2R^3$. The phenyalanine derivatives needed to prepare the optically pure compounds of general formula (V) may be prepared from the compounds of general formula

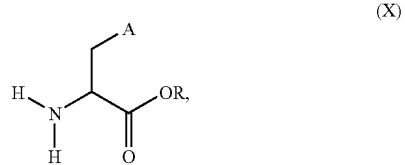

(X)

wherein A is as hereinbefore defined and R denotes an unbranched alkyl group, preferably the methyl or ethyl group, by racemate cleaving.

This racemate cleaving may be carried out using enzymatic methods, while only one enantiomer of the racemate is transformed and the resulting mixture is then separated using physicochemical methods, preferably using chromatographic methods. A suitable enzyme system for this step is the enzyme alkalase 2.4 L FG (Novozymes A/S; DK 2880 Bagsvaerd). The compounds of general formula (X) can then be converted into the enantiomerically pure compounds of general formula (V) using methods familiar to the peptide chemist.

If the group X in compounds of general formula (V) denotes the oxygen atom, the hydroxycarboxylic acids of general formula

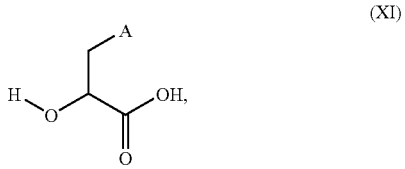

(XI)

wherein A is as hereinbefore defined which are needed for the synthesis may be obtained from compounds of general formula (X), with the proviso that R denotes the hydrogen atom.

With the proviso that the group A does not contain the amino or methylamino group, by diazotising compounds of general formula (X) with a suitable diazotising reagent, preferably sodium nitrite in an acid medium, it is possible to obtain the compounds of general formula (XI). If enantiomerically pure compounds are used the corresponding enantiomerically pure hydroxycarboxylic acid compounds are obtained, the configuration being retained as the reaction proceeds.

Another method of obtaining compounds of general formula (XI) wherein the groups A are as hereinbefore defined comprises alkylating the compound

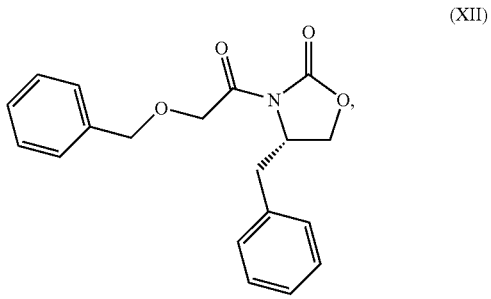

(XII)

with correspondingly substituted benzylchlorides, benzylbromides or benzyliodides of general formula

(XIII)

wherein A is as hereinbefore defined and X denotes a chlorine, bromine or iodine atom, analogously to methods known from the literature (Michael T. Crimmins, Kyle A. Emmitte and Jason D. Katz, Org. Lett. 2, 2165-2167 [2000]).

The diastereomeric products formed may then be separated using physicochemical methods, preferably chromatographic methods. The hydrolytic cleaving of the chiral auxiliary, coupling with amines of general formula $HNR^2R^3$ and cleaving of the benzyl protective group also provides a way of obtaining enantiomerically pure hydroxycarboxylic acid compounds of general formula (V).

Compounds of general formula (XI) wherein the groups A are as hereinbefore defined may also be obtained by boiling down 2-acetylamino-3-phenyl-acrylic acids of formula

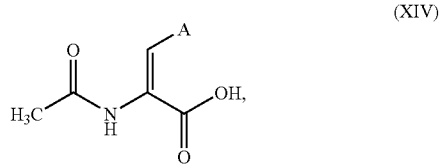

(XIV)

using strong acids and subsequently reducing the 2-hydroxy-3-phenyl-acrylic acids formed.

The starting compounds of general formula (VI) are obtained for example by reacting amines of general formula $HNR^2R^3$ with 2-(alkoxycarbonylmethyl)-3-aryl-propanoic acids and subsequently hydrolytically cleaving the alkyl group. The 2-(alkoxycarbonylmethyl)-3-aryl-propanoic acids needed may be prepared analogously to methods known from the literature (David A. Evans, Leester D. Wu, John J. M. Wiener, Jeffrey S. Johnson, David H. B. Ripin and Jason S. Tedrow, J. Org. Chem. 64, 6411-6417 [1999]; Saul G. Cohen and Aleksander Milovanovic, J. Am. Chem. Soc. 90, 3495-3502 [1968]; Hiroyuki Kawano, Youichi Ishii, Takao Ikariya, Masahiko Saburi, Sadao Yoshikawa, Yasuzo Uchida and Hidenori Kumobayashi, Tetrahedron Letters 28, 1905-1908

[1987]). Carboxylic acids of general formula (VIII) may be prepared by the methods recited in WO 98/11128 from generally available starting materials.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

The present invention relates to racemates if the compounds of general formula (I) have only one chiral element. However, the application also includes the individual diastereomeric pairs of antipodes or mixtures thereof which are obtained if there is more than one chiral element in the compounds of general formula (I), as well as the individual optically active enantiomers of which the above-mentioned racemates are made up.

Also included in the subject matter of this invention are the compounds according to the invention, including the salts thereof, in which one or more hydrogen atoms, for example one, two, three, four or five hydrogen atoms, are replaced by deuterium.

The new compounds of general formula (I) and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 μl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 μl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 μM human CGRP-alpha during incubation.

The concentration binding curves are analysed using computer-aided non-linear curve matching.

The compounds mentioned hereinbefore show IC$_{50}$ values ≦10000 nM in the test described.

B. CGRP Antagonism in SK-N-MC Cells

SK-N-MC cells (1 million cells) are washed twice with 250 μl incubation buffer (Hanks' HEPES, 1 mM 3-isobutyl-1-methylxanthine, 1% BSA, pH 7.4) and pre-incubated at 37° C. for 15 minutes. After the addition of CGRP (10 μl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 μl of 1 M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA$_2$ values of antagonistically acting substances are determined graphically.

The compounds of general formula I exhibit CGRP-antagonistic properties in the in vitro test model described, in a dosage range between $10^{-12}$ and $10^{-5}$ M.

In view of their pharmacological properties the compounds of general formula I and the salts thereof with physiologically acceptable acids are thus suitable for the acute and prophylactic treatment of headaches, particularly migraine or cluster headaches. Moreover, the compounds of general formula I also have a positive effect on the following diseases: non-insulin-dependent diabetes mellitus ("NIDDM"), complex regional pain syndrome (CRPS1), cardiovascular diseases, morphine tolerance, diarrhoea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and resultant reduced blood supply to the tissues, e.g. shock and sepsis. In addition, the compounds according to the invention have a general pain-relieving effect.

The symptoms of menopausal hot flushes caused by vasodilatation and increased blood flow in oestrogen-deficient women and hormone-treated patients with prostate carcinoma are favourably affected by the CGRP-antagonists of the present application in a preventive and acute-therapeutic capacity, this therapeutic approach being distinguished from hormone replacement by the absence of side effects.

The dosage required to achieve a corresponding effect is conveniently 0.01 to 3 mg/kg of body weight, preferably 0.01 to 1 mg/kg of body weight, when administered intravenously or subcutaneously and 0.01 to 20 mg/kg of body weight, preferably 0.1 to 10 mg/kg of body weight when administered orally, and 0.01 to 10 mg/kg of body weight, preferably 0.1 to 10 mg/kg of body weight when administered nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. angiotensin II receptor antagonists, α-agonists and α-antagonists, $5\text{-HT}_{1B/1D}$ agonists, AMPA antagonists, mild analgesics, antidepressants, antiemetics, anti-convulsants, antimuscarinics, β-blockers, calcium antagonists, corticosteroids, ergot alkaloids, histamine-H1 receptor antagonists, neurokinine antagonists, neuroleptics, non-steroidal antiinflammatories, NO-synthase inhibitors, prokinetics, selective serotonin reuptake inhibitors or other anti-migraine agents, which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, azathioprine, diclofenac, diflunisal, fenbufen, fenoprofen, flurbiprofen, ibuprofen, indometacin, ketoprofen, leflunomide, lomoxicam, mefenamic acid, naproxen, phenylbutazone, piroxicam, sulphasalazine, tenoxicam, zomepirac or the pharmaceutically acceptable salts thereof as well as meloxicam and other selective COX2-inhibitors, such as for example rofecoxib and celecoxib.

It is also possible to use candesartan, eprosartan, irbesartan, losartan, olmesartan, tasosartan, telmisartan, valsartan, duloxetine, ergotamine, dihydroergotamine, metoclopramide, domperidone, diphenhydramine, cyclizine, promethazine, chlorpromazine, vigabatrin, timolol, isometheptene, pizotifen, botox, gabapentin, topiramate, riboflavin, montelukast, lisinopril, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, lidocaine or diltiazem and other $5\text{-HT}_{1B/1D}$-agonists such as, for example, almotriptan, avitriptan, donitriptan, eletriptan, frovatriptan, naratriptan, rizatriptan, sumatriptan and zolmitriptan and the physiologically acceptable salts thereof.

The dosage of these active substances is expediently 1/5 of the lowest recommended dose to 1/1 of the normally recommended dose, i.e. for example 20 to 100 mg of sumatriptan.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Experimental Section

As a rule, IR, $^1$H-NMR and/or mass spectra have been obtained for the compounds prepared.

Unless otherwise stated, $R_f$ values are obtained using ready-made silica gel TLC plates 60 F254 (E. Merck, Darmstadt, Item no. 1.05714) without chamber saturation. The $R_f$ values obtained under the name Alox were determined using ready-made aluminium oxide TLC plates 60 F254 (E. Merck, Darmstadt, Item no. 1.05713) without chamber saturation The ratios given for the eluants relate to units by volume of the solvent in question. The units by volume specified for $NH_3$ refer to a concentrated solution of $NH_3$ in water.

Unless otherwise stated, the acid, base and salt solutions used for working up the reaction solutions are aqueous systems of the concentrations specified.

For chromatographic purification, silica gel made by Millipore (MATREX™, 35-70 μm) is used. For chromatographic purification, Alox (E. Merck, Darmstadt, standardised aluminium oxide 90, 63-200 μm, Item no. 1.01097.9050) is used.

The HPLC data provided are measured using the parameters specified below:

Analytical column: Zorbax column (Agilent Technologies), SB (Stable Bond) C18; 3.5 μm; 4.6×75 mm; column temperature: 30° C.; flow: 0.8 mL/min; injection volume: 5 μL; detection at 254 nm Method A:

| time (min) | percent by volume of water (with 0.1% formic acid) | percent by volume of acetonitrile (with 0.1% formic acid) |
|---|---|---|
| 0 | 90 | 10 |
| 9 | 10 | 90 |
| 10 | 10 | 90 |
| 11 | 90 | 10 |

In preparative HPLC purifications as a rule the same gradients are used as were used to collect the analytical HPLC data.

The products are collected under mass control and the fractions containing the product are combined and freeze-dried.

If no detailed information is given as to the configuration, it is not clear whether it is a pure enantiomer or whether partial or even complete racemisation has occurred.

The following abbreviations are used in the description of the experiments:
abs. absolute
Boc tert.-butoxycarbonyl
CDI N,N'-carbonyldiimidazole
CDT 1,1'-carbonyldi-(1,2,4-triazol)
cyc cyclohexane
DCM dichloromethane
DMAP 4-dimethylaminopyridine
DMF N,N-dimethylformamide
EtOAc ethyl acetate
EtOH ethanol
semiconc. semiconcentrated
HCl hydrochloric acid
HOAC acetic acid
HOBt 1-hydroxybenzotriazole-hydrate
i. vac. under vacuum (in vacuo)
KOH potassium hydroxide
conc. concentrated MeOH methanol
NaCl sodium chloride
NaOH sodium hydroxide
NMP N-methylpyrrolidone
org. organic
PE petroleum ether
RT ambient temperature
TBME tert.-butyl-methylether
TBTU 2-(1H-benzotriazol-1-yl)-1,1,3,3-tetramethyluronium-tetrafluoroborate
TFA trifluoroacetic acid
THF tetrahydrofuran

EXAMPLE 1

(R)-1-(4-amino-3-chloro-5-trifluoromethyl-benzyl)-2-oxo-2-[4-(2-piperidin-1-yl-ethyl)-piperidin-1-yl]-ethyl 4-(2-oxo-1,2,4,5-tetrahydro-benzo[d][1,3]diazepin-3-yl)-piperidine-1-carboxylate

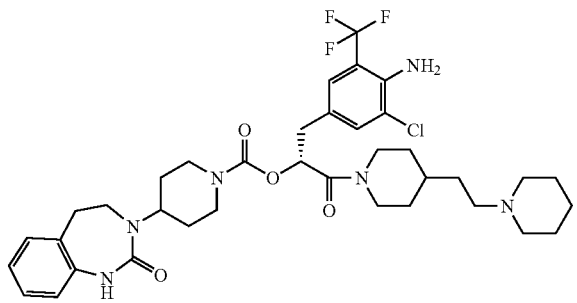

(1a) (E)-2-acetylamino-3-(4-amino-3-chloro-5-trifluoromethyl-phenyl)-acrylic Acid A mixture of 50.0 g (224 mmol) 4-amino-3-chloro-5-trifluoromethyl-benzaldehyde, 39.3 g (335 mmol) N-acetylglycine, 27.5 g (335 mmol) sodium acetate and 200 ml acetic anhydride was stirred for 2 hours in an oil bath at an oil bath temperature of 128° C. After cooling to an oil bath temperature of 90° C. 100 ml of water were added dropwise and the resulting suspension was added to a mixture of 1000 ml of water and 500 ml of toluene. The precipitate formed was suction filtered, washed with 300 ml of toluene and 500 ml of water and dried overnight at 60° C. in the circulating air dryer.

Yield: 51.0 g (71% of theory) ESI-MS: (M+H)$^+$=323/325 (Cl)

(1b) (E)-3-(4-amino-3-chloro-5-trifluoromethyl-phenyl)-2-hydroxy-acrylic Acid 51.0 g (158 mmol) (E)-2-acetylamino-3-(4-amino-3-chloro-5-trifluoromethyl-phenyl)-acrylic acid, dissolved in 408 ml NMP, were combined with 612 ml aqueous 4-molar hydrochloric acid solution and stirred for 3 hours at a bath temperature of 130° C. stirred. The reaction mixture was cooled and poured onto 2000 ml of water with stirring. The precipitate formed was suction filtered, washed with 400 ml of water, dried overnight at 60° C. and recrystallised from 1000 ml boiling toluene.

Yield: 24.2 g (54% of theory) MS: (M)$^+$=281/283 (Cl)

(1c) (R)-3-(4-amino-3-chloro-5-trifluoromethyl-phenyl)-2-hydroxy-propionic Acid 33.5 g (104.3 mmol) (−)-DIP-chloride dissolved in 195 ml THF was added under protective nitrogen gas to a mixture of 24.5 g (86.9 mmol) (E)-3-(4-amino-3-chloro-5-trifluoromethyl-phenyl)-2-hydroxy-acrylic acid, 12.1 ml (86.9 mmol) triethylamine and 98 ml THF cooled to −20° C. The reaction mixture was stirred for 1.5 hours at −20° C., brought to ambient temperature and evaporated down under reduced pressure. The residue was combined with 200 ml aqueous 1-molar sodium hydroxide solution and 150 ml TBME and stirred thoroughly. The aqueous phase was separated off, acidified with 2-molar hydrochloric acid solution with stirring and extracted twice with 250 ml TBME. The combined organic phases were filtered through activated charcoal and evaporated down under reduced pressure. The residue was heated to boiling with 500 ml of water and the hot solution was filtered clear through Celite. The precipitate formed at ambient temperature was suction filtered and dried at 65° C. in the circulating air dryer.

Yield: 14.3 g (58% of theory) MS: (M+H)$^+$=284/286 (Cl)

(1d) ethyl (R)-3-(4-amino-3-chloro-5-trifluoromethyl-phenyl)-2-hydroxy-propionate A mixture of 14.3 g (50.0 mmol) (R)-3-(4-amino-3-chloro-5-trifluoromethyl-phenyl)-2-hydroxy-propionic acid and 100 ml of ethanol was combined with 100 ml of an approx. 12-molar ethanolic hydrochloric acid solution and stirred overnight. The reaction mixture was evaporated down under reduced pressure.

Yield: 15.7 g (100% of theory) MS: (M+H)$^+$=312/314 (Cl)

(1e) (R)-2-(4-amino-3-chloro-5-trifluoromethyl-phenyl)-1-ethoxycarbonyl-ethyl 4-(2-oxo-1,2,4,5-tetrahydro-benzo[d][1,3]diazepin-3-yl)-piperidine-1-carboxylate 5.2 g (25.6 mmol) 4-nitrophenyl chloroformate were added under protective nitrogen gas to a mixture of 3.1 g (25.6 mmol) DMAP and 70 ml of pyridine and stirred for 1.5 hours at ambient temperature. Then 8.0 g (25.7 mmol) ethyl (R)-3-(4-amino-3-chloro-5-trifluoromethyl-phenyl)-2-hydroxy-propionate, dissolved in 30 ml of pyridine, were slowly added dropwise at ambient temperature, the reaction mixture was stirred for 2 hours at ambient temperature, 6.3 g (25.6 mmol) 3-piperidin-4-yl-1,3,4,5-tetrahydro-1,3-benzdiazepin-2-one were added as a solid substance and the mixture was stirred overnight at ambient temperature. The reaction mixture was evaporated down under reduced pressure and distributed between 200 ml of ethyl acetate and 200 ml aqueous 10% citric acid solution. The organic phase washed twice with 200 ml 10% citric acid solution and five times with 150 ml 15% aqueous potassium carbonate solution, dried over sodium sulphate and evaporated down under reduced pressure. The residue was purified by column chromatography.

Yield: 5.0 g (33% of theory) MS: (M+H)$^+$=583/585 (Cl)

(1f) (R)-2-(4-amino-3-chloro-5-trifluoromethyl-phenyl)-1-carboxyethyl 4-(2-oxo-1,2,4,5-tetrahydro-benzo[d][1,3]diazepin-3-yl)-piperidine-1 carboxylate A solution of 804 mg (33.5 mmol) lithium hydroxide dissolved in 80 ml of water was added dropwise to a mixture of 13.0 g (22.3 mmol) (R)-2-(4-amino-3-chloro-5-trifluoromethyl-phenyl)-1-ethoxycarbonyl-ethyl 4-(2-oxo-1,2,4,5-tetrahydro-benzo[d]-[1,3]diazepin-3-yl)-piperidine-1-carboxylate and 120 ml THF. The mixture was stirred for 3 hours at ambient temperature, freed from THF under reduced pressure, combined with 150 ml of water, and acidified by the addition of aqueous 4-molar hydrochloric acid solution. Then the aqueous phase was extracted with 300 ml of ethyl acetate, the organic phase was dried and evaporated down under reduced pressure. The residue was recrystallised from 50 ml isopropanol.

Yield: 5.3 g (43% of theory)

(1g) (R)-1-(4-amino-3-chloro-5-trifluoromethyl-benzyl)-2-oxo-2-[4-(2-piperidin-1-yl-ethyl)-piperidin-1-yl]-ethyl 4-(2-oxo-1,2,4,5-tetrahydro-benzo[d][1,3]diazepin-3-yl)-piperidine-1-carboxylate A mixture of 100 mg (0.18 mmol) (R)-2-(4-amino-3-chloro-5-trifluoromethyl-phenyl)-1-carboxyethyl 4-(2-oxo-1,2,4,5-tetrahydro-benzo[d][1,3]diazepin-3-yl)-piperidine-1-carboxylate, 35.3 mg (0.18 mmol) 4-(2-piperidin-1-yl-ethyl)-piperidine, 64.2 mg (0.20 mmol) TBTU, 0.028 ml (0.20 mmol) triethylamine and 2.0 ml DMF was stirred for 12 hours at ambient temperature. The reaction mixture was purified by column chromatography.

Yield: 84 mg (64% of theory) MS: $(M+H)^+$=733/735 (Cl) retention time HPLC: 6.5 min (method A)

The following compounds were prepared analogously from in each case 100 mg (R)-2-(4-amino-3-chloro-5-trifluoromethyl-phenyl)-1-carboxy-ethyl 4-(2-oxo-1,2,4,5-tetrahydro-benzo[d][1,3]diazepin-3-yl)-piperidine-1-carboxylate and the corresponding amount of amine:

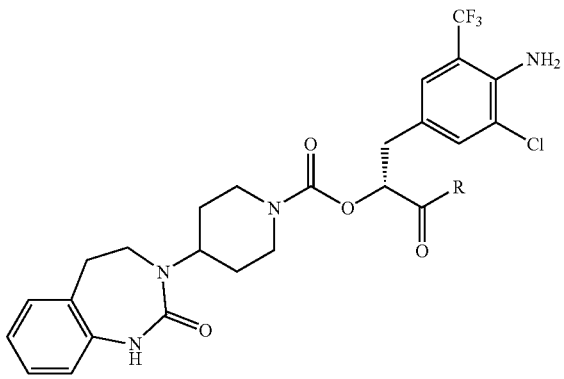

| Example | R | Yield (%) | Mass spectrum | retention time HPLC (method) |
|---|---|---|---|---|
| 1.1 | | 15 | 732/734 $[M + H]^+$ | 6.0 min (A) |

(R)-1-(4-amino-3-chloro-5-trifluoromethyl-benzyl)-2-[4-(1-aza-bicyclo[2.2.2]oct-3-yl)-piperazin-1-yl]-2-oxo-ethyl 4-(2-oxo-1,2,4,5-tetrahydro-benzo[d][3]diazepin-3-yl)-piperidine-1-carboxylate

| 1.2 | | 74 | 732/734 $[M + H]^+$ | 5.5 min (A) |

(R)-1-(4-amino-3-chloro-5-trifluoromethyl-benzyl)-2-[4-(5-methyl-2,5-diaza-bicyclo-[2.2.1]hept-2-yl)-piperidin-1-yl]-2-oxo-ethyl 4-(2-oxo-1,2,4,5-tetrahydro-benzo[d][1,3]diazepin-3-yl)-piperidine-1-carboxylate

| 1.3 | | 92 | 667/669 $[M + H]^+$ | 5.9 min (A) |

(R)-2-(4-amino-3-chloro-5-trifluoromethyl-phenyl)-1-(5-dimethylamino-pentylcarbamoyl)-ethyl 4-(2-oxo-1,2,4,5-tetrahydro-benzo[d][1,3]diazepin-3-yl)-piperidine-1-carboxylate

| | | | | |
|---|---|---|---|---|
| 1.4 | 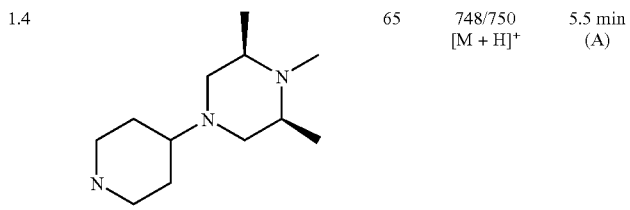 | 65 | 748/750 [M + H]+ | 5.5 min (A) |

(R)-1-(4-amino-3-chloro-5-trifluoromethyl-benzyl)-2-oxo-2-[4-((3R,5S)-3,4,5-trimethyl-piperazin-1-yl)-piperidin-1-yl]-ethyl 4-(2-oxo-1,2,4,5-tetrahydro-benzo[d][1,3]diazepin-3-yl)-piperidine-1-carboxylate

| | | | | |
|---|---|---|---|---|
| 1.5 | 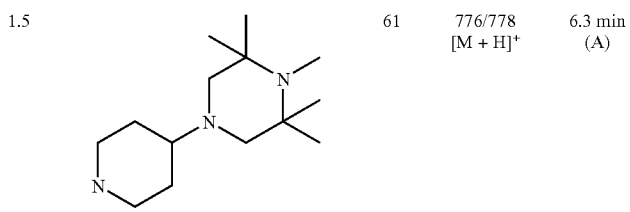 | 61 | 776/778 [M + H]+ | 6.3 min (A) |

(R)-1-(4-amino-3-chloro-5-trifluoromethyl-benzyl)-2-oxo-2-[4-(3,3,4,5,5-pentamethyl-piperazin-1-yl)-piperidin-1-yl]-ethyl 4-(2-oxo-1,2,4,5-tetrahydro-benzo[d][1,3]diazepin-3-yl)-piperidine-1-carboxylate

| | | | | |
|---|---|---|---|---|
| 1.6 | 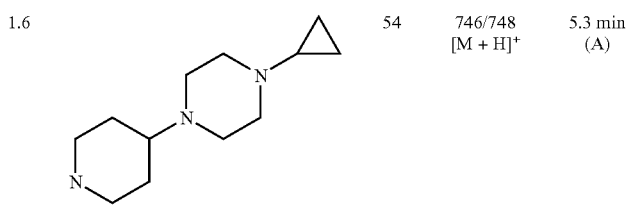 | 54 | 746/748 [M + H]+ | 5.3 min (A) |

(R)-1-(4-amino-3-chloro-5-trifluoromethyl-benzyl)-2-[4-(4-cyclopropyl-piperazin-1-yl)-piperidin-1-yl]-2-oxo-ethyl 4-(2-oxo-1,2,4,5-tetrahydro-benzo[d][1,3]diazepin-3-yl)-piperidine-1-carboxylate

| | | | | |
|---|---|---|---|---|
| 1.7 | 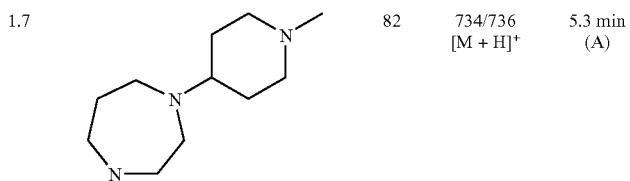 | 82 | 734/736 [M + H]+ | 5.3 min (A) |

(R)-1-(4-amino-3-chloro-5-trifluoromethyl-benzyl)-2-[4-(1-methyl-piperidin-4-yl)-[1,4]diazepan-1-yl]-2-oxo-ethyl 4-(2-oxo-1,2,4,5-tetrahydro-benzo[d][1,3]diazepin-3-yl)-piperidine-1-carboxylate

| | | | | |
|---|---|---|---|---|
| 1.8 | 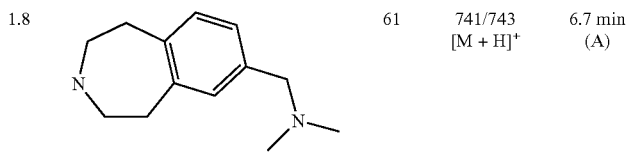 | 61 | 741/743 [M + H]+ | 6.7 min (A) |

(R)-1-(4-amino-3-chloro-5-trifluoromethyl-benzyl)-2-(7-dimethylaminomethyl-1,2,4,5-tetrahydro-benzo[d]azepin-3-yl)-2-oxo-ethyl 4-(2-oxo-1,2,4,5-tetrahydro-benzo[d][1,3]diazepin-3-yl)-piperidine-1-carboxylate -continued

| | | | | |
|---|---|---|---|---|
| 1.9 | 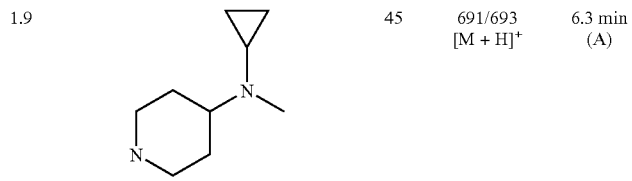 | 45 | 691/693 [M + H]⁺ | 6.3 min (A) |

(R)-1-(4-amino-3-chloro-5-trifluoromethyl-benzyl)-2-[4-(cyclopropyl-methyl-amino)-piperidin-1-yl]-2-oxo-ethyl 4-(2-oxo-1,2,4,5-tetrahydro-benzo[d][1,3]diazepin-3-yl)-piperidine-1-carboxylate

| 1.10 | 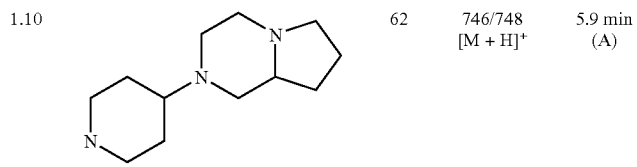 | 62 | 746/748 [M + H]⁺ | 5.9 min (A) |
|---|---|---|---|---|

(R)-1-(4-amino-3-chloro-5-trifluoromethyl-benzyl)-2-[4-(hexahydro-pyrrolo[1,2-a]-pyrazin-2-yl)-piperidin-1-yl]-2-oxo-ethyl 4-(2-oxo-1,2,4,5-tetrahydro-benzo[d][1,3]diazepin-3-yl)-piperidine-1-carboxylate

| 1.11 | 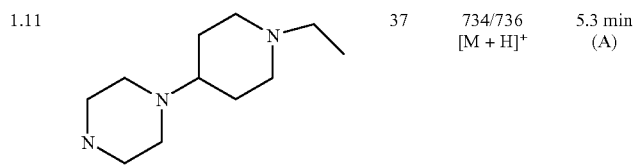 | 37 | 734/736 [M + H]⁺ | 5.3 min (A) |
|---|---|---|---|---|

(R)-1-(4-amino-3-chloro-5-trifluoromethyl-benzyl)-2-[4-(1-ethyl-piperidin-4-yl)-piperazin-1-yl]-2-oxo-ethyl 4-(2-oxo-1,2,4,5-tetrahydro-benzo[d][1,3]diazepin-3-yl)-piperidine-1-carboxylate

| 1.12 | 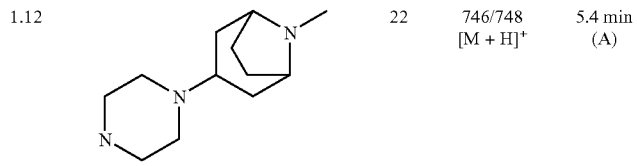 | 22 | 746/748 [M + H]⁺ | 5.4 min (A) |
|---|---|---|---|---|

(R)-1-(4-amino-3-chloro-5-trifluoromethyl-benzyl)-2-[4-(8-methyl-8-aza-bicyclo[3.2.1]oct-3-yl)-piperazin-1-yl]-2-oxo-ethyl 4-(2-oxo-1,2,4,5-tetrahydro-benzo[d][1,3]diazepin-3-yl)-piperidine-1-carboxylate

| 1.13 | 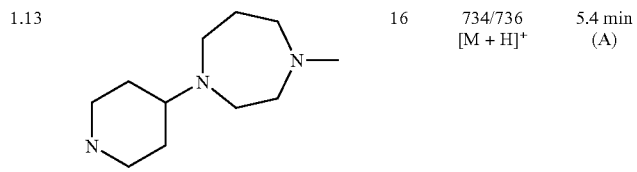 | 16 | 734/736 [M + H]⁺ | 5.4 min (A) |
|---|---|---|---|---|

(R)-1-(4-amino-3-chloro-5-trifluoromethyl-benzyl)-2-[4-(4-methyl-[1,4]diazepan-1-yl)-piperidin-1-yl]-2-oxo-ethyl 4-(2-oxo-1,2,4,5-tetrahydro-benzo[d][1,3]diazepin-3-yl)-piperidine-1-carboxylate

| 1.14 |  | 88 | 677/679 [M + H]⁺ | 5.4 min (A) |
|---|---|---|---|---|

(R)-1-(4-amino-3-chloro-5-trifluoromethyl-benzyl)-2-(4-cyclopropylmethyl-piperazin-1-yl)-2-oxo-ethyl 4-(2-oxo-1,2,4,5-tetrahydro-benzo[d][1,3]diazepin-3-yl)-piperidine-1-carboxylate

| | | | | |
|---|---|---|---|---|
| | -continued | | | |
| 1.15 | 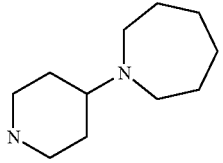 | 53 | 719/721 [M + H]+ | 6.5 min (A) |

(R)-1-(4-amino-3-chloro-5-trifluoromethyl-benzyl)-2-(4-azepan-1-yl-piperidin-1-yl)-2-oxo-ethyl 4-(2-oxo-1,2,4,5-tetrahydro-benzo[d][1,3]diazepin-3-yl)-piperidine-1-carboxylate

| 1.16 | 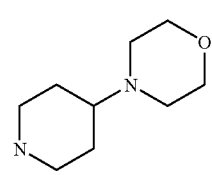 | 68 | 707/709 [M + H]+ | 6.0 min (A) |
|---|---|---|---|---|

(R)-1-(4-amino-3-chloro-5-trifluoromethyl-benzyl)-2-(4-morpholin-4-yl-piperidin-1-yl)-2-oxo-ethyl 4-(2-oxo-1,2,4,5-tetrahydro-benzo[d][1,3]diazepin-3-yl)-piperidine-1-carboxylate

| 1.17 | 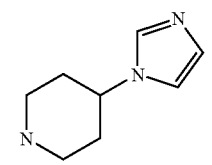 | 33 | 688/690 [M + H]+ | 6.2 min (A) |
|---|---|---|---|---|

(R)-1-(4-amino-3-chloro-5-trifluoromethyl-benzyl)-2-(4-imidazol-1-yl-piperidin-1-yl)-2-oxo-ethyl 4-(2-oxo-1,2,4,5-tetrahydro-benzo[d][1,3]diazepin-3-yl)-piperidine-1-carboxylate

EXAMPLE 2

4-(2-oxo-1,2,4,5-tetrahydro-benzo[d][1,3]diazepin-3-yl)-piperidine-1-carboxylic acid-{(R)-1-(4-amino-3-chloro-5-trifluoromethyl-benzyl)-2-[4-(4-cyclopropyl-piperazin-1-yl)-piperidin-1-yl]-2-oxo-ethyl}-amide

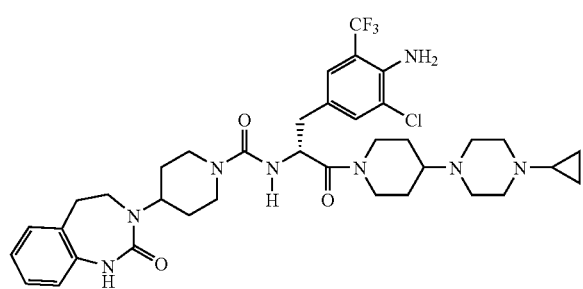

(2a) ethyl (R)-2-amino-3-(4-amino-3-chloro-5-trifluoromethyl-phenyl)-propionate

A solution of 3.5 g (10.97 mmol) (R)-2-amino-3-(4-amino-3-chloro-5-trifluoromethyl-phenyl)-propionic acid in 100 mL EtOH and 70 mL ethanolic hydrochloric acid solution (11.5 M) was stirred overnight at RT. The mixture was evaporated down i. vac., the residue was taken up in 150 mL water, combined with 30 mL 15% $K_2CO_3$ solution, extracted with 150 mL EtOAc, the organic phase was separated off and dried over $Na_2SO_4$. After the desiccant and solvent had been eliminated the desired product was obtained.

Yield: 3.5 g (92% of theory) ESI-MS: (M+H)+=311/313 (Cl)

(2b) ethyl (R)-3-(4-amino-3-chloro-5-trifluoromethyl-phenyl)-2-{[4-(2-oxo-1,2,4,5-tetrahydro-1,3-benzdiazepin-3-yl)-piperidine-1-carbonyl]-amino}-propionate 1.8 g (11.0 mmol) CDT were added to a solution of 3.2 g (10.2 mmol) ethyl (R)-2-amino-3-(4-amino-3-chloro-5-trifluoromethyl-phenyl)-propionate and 1.8 mL (10.3 mmol) ethyldiisopropylamine in 150 mL THF cooled to 0° C. and the reaction mixture was stirred for 45 min at this temperature and after removal of the ice bath stirred for a further 30 min. Then 2.5 g (10.2 mmol) 3-piperidin-4-yl-1,3,4,5-tetrahydro-1,3-benzdiazepin-2-one, suspended in 50 mL THF was added. 40 mL DMF were added to the reaction solution and this was stirred for 2 h at 80° C. The mixture was evaporated down i. vac., combined with 200 mL EtOAc and 200 mL 10% citric acid solution, the organic phase was separated off, extracted with 150 mL $NaHCO_3$ solution and dried over $Na_2SO_4$. After the desiccant and solvent had been eliminated the desired product was obtained.

Yield: 5.9 g (100% of theory) ESI-MS: (M+H)+=582/584 (Cl) $R_f$: 0.4 (silica gel, EtOAc)

(2c) (R)-3-(4-amino-3-chloro-5-trifluoromethyl-phenyl)-2-{[4-(2-oxo-1,2,4,5-tetrahydro-1,3-benzdiazepin-3-yl)-piperidine-1-carbonyl]-amino}-propionic acid A solution of 0.64 g (15 mmol) lithium hydroxide hydrate in 100 mL water was added to a suspension of 6.0 g (10.31 mmol) ethyl (R)-3-(4-amino-3-chloro-5-trifluoromethyl-phenyl)-2-{[4-(2-oxo-1,2,4,5-tetrahydro-1,3-benzdiazepin-3-yl)-piperidine-1-carbonyl]-amino}-propionate in 50 mL THF. In each case 100 mL water and THF were again added to this suspension, and a solution formed after 5 min. This was stirred for 1 hour at RT, the THF was eliminated i.vac., the remainder was diluted with 100 mL water and 1 M aqueous hydrochloric acid solution was added dropwise while cooling with ice until an acid reaction was obtained. The precipitated substance was filtered, washed with water and dried in the air.
Yield: 5.5 g (96% of theory) ESI-MS: (M+H)+=554/556 (Cl)

(2d) 4-(2-oxo-1,2,4,5-tetrahydro-benzo[d][1,3]diazepin-3-yl)-piperidine-1-carboxylic acid-{(R)-1-(4-amino-3-chloro-5-trifluoromethyl-benzyl)-2-[4-(4-cyclopropyl-piperazin-1-yl)-piperidin-1-yl]-2-oxo-ethyl}-amide 321 mg (1.0 mmol) TBTU, 0.28 mL (2.0 mmol) triethylamine and 200 mg (0.9 mmol) 1-cyclopropyl-4-piperidin-4-yl-piperazine were added to a solution of 500 mg (0.90 mmol) (R)-3-(4-amino-3-chloro-5-trifluoromethyl-phenyl)-2-{[4-(2-oxo-1,2,4,5-tetrahydro-1,3-benzodiazepin-3-yl)-piperidine-1-carbonyl]-amino}-propionic acid in 100 mL THF and the reaction mixture was stirred overnight at RT. The reaction solution was evaporated down under reduced pressure, the residue was distributed between 150 ml of ethyl acetate and 150 ml of 15% aqueous potassium carbonate solution, the organic phase was separated off, dried over sodium sulphate and evaporated down under reduced pressure. The residue was then purified by column chromatography (silica gel, gradient from methylene chloride/methanol/ammonia from 100/0/0 to 0/90/10 within 60 minutes). The corresponding fractions were evaporated down under reduced pressure, the residue was triturated with 50 ml diisopropylether, suction filtered and dried.
Yield: 440 mg (65% of theory) ESI-MS: (M+H)+=746/748 (Cl) R$_f$: 0.55 (methylene chloride/methanol/ammonia=90/10/1)

EXAMPLE 3

(R)-1-(4-chloro-3-trifluoromethyl-benzyl)-2-[4-(4-methyl-piperazin-1-yl)-piperidin-1-yl]-2-oxo-ethyl 4-(2-oxo-1,2,4,5-tetrahydro-benzo[d][1,3]diazepin-3-yl)-piperidine-1-carboxylate

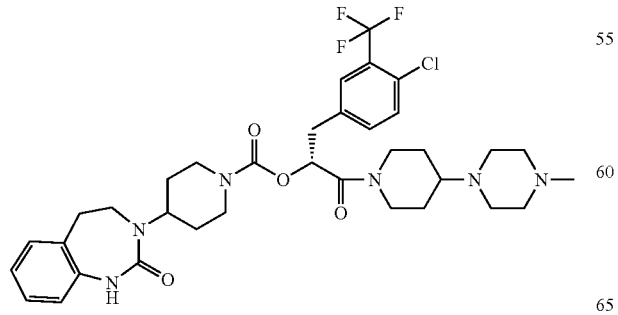

(3a) (E)-2-acetylamino-3-(4-chloro-3-trifluoromethyl-phenyl)-acrylic Acid

Prepared analogously to Example 1a.
Yield: 75% of theory ESI-MS: (M+H)+=308/310 (Cl)

(3b) (E)-3-(4-chloro-3-trifluoromethyl-phenyl)-2-hydroxy-acrylic Acid

Prepared analogously to Example 1b.
Yield: 55% of theory MS: (M−H)−=265/267 (Cl)

(3c) (R)-3-(4-chloro-3-trifluoromethyl-phenyl)-2-hydroxy-propionic Acid

Prepared analogously to Example 1c.
Yield: 64% of theory ESI-MS: (M−H)−=267/269 (Cl)

(3d) methyl (R)-3-(4-chloro-3-trifluoromethyl-phenyl)-2-hydroxy-propionate

Prepared analogously to Example 1d.
Yield: 78% of theory ESI-MS: (M)+=282/284 (Cl)

(3e) (R)-2-(4-chloro-3-trifluoromethyl-phenyl)-1-methoxycarbonyl-ethyl 4-(2-oxo-1,2,4,5-tetrahydro-benzo[d][1,3]diazepin-3-yl)-piperidine-1-carboxylate Prepared analogously to Example 1e.
Yield: 22% of theory ESI-MS: (M+H)+=554/556 (Cl)

(3f) (R)-2-(4-chloro-3-trifluoromethyl-phenyl)-1-carboxyethyl 4-(2-oxo-1,2,4,5-tetrahydro-benzo[d][1,3]diazepin-3-yl)-piperidine-1-carboxylate Prepared analogously to Example 1f.
Yield: 77% of theory ESI-MS: (M+H)+=540/542 (Cl)

(3g) (R)-1-(4-chloro-3-trifluoromethyl-benzyl)-2-[4-(4-methyl-piperazin-1-yl)-piperidin-1-yl]-2-oxo-ethyl 4-(2-oxo-1,2,4,5-tetrahydro-benzo[d][1,3]diazepin-3-yl)-piperidine-1-carboxylate Prepared an analogously to Example 1g.
Yield: 40% of theory ESI-MS: (M+H)+=705/707 (Cl) R$_f$: 0.4 (methylene chloride/cyclohexane/methanol/ammonia=70/15/15/2)

EXAMPLE 3.1

(R)-1-(4-chloro-3-trifluoromethyl-benzyl)-2-[4-(1-methyl-piperidin-4-yl)-piperazin-1-yl]-2-oxo-ethyl 4-(2-oxo-1,2,4,5-tetrahydro-benzo[d][1,3]diazepin-3-yl)-piperidine-1-carboxylate

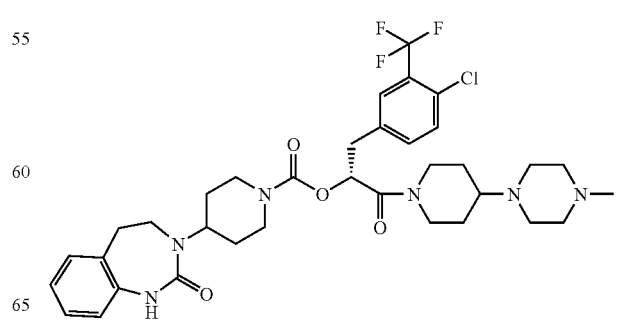

Prepared analogously to Example 3g.

Yield: 26% of theory ESI-MS: (M+H)⁺=705/707 (Cl) $R_f$: 0.4 (methylene chloride/cyclohexane/methanol/ammonia=70/15/15/2)

EXAMPLE 4

4-(2-oxo-1,2,4,5-tetrahydro-benzo[d][1,3]diazepin-3-yl)-piperidine-1-carboxylic acid-[(R)-1-(4-amino-3-chloro-5-methyl-benzyl)-2-(4-cyclopropyl-piperazin-1-yl)-2-oxo-ethyl]-amide

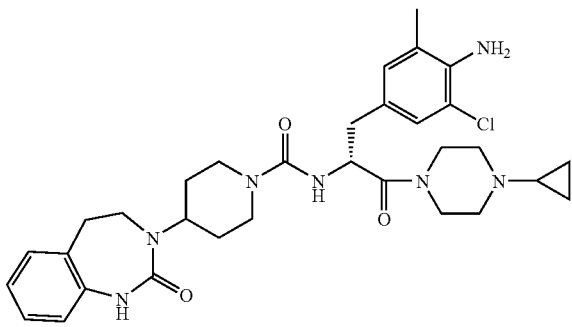

(4a) methyl (E)-2-acetylamino-3-(4-amino-3-chloro-5-methyl-phenyl)-acrylate

Under protective nitrogen gas 2.02 g (9.0 mmol) palladium (II)acetate and 2.82 g (9.0 mmol) tri-o-tolylphosphine were added to a mixture of 25.0 g (113 mmol) 4-bromo-2-chloro-6-methyl-aniline, 19.9 g (136 mmol) methyl 2-acetamidoacrylate, 350 ml triethylamine and 150 ml acetonitrile at ambient temperature. The reaction mixture was stirred for 18 hours at 80° C., evaporated down under reduced pressure, the residue was combined with 600 ml dichloromethane and water and filtered off from the insoluble precipitate. The organic phase was dried over sodium sulphate, evaporated down under reduced pressure and then combined with 200 ml of ethyl acetate/cyclohexane (3/1). The insoluble fraction was suction filtered and the mother liquor was purified by column chromatography through silica gel. The corresponding fractions were evaporated down under reduced pressure and combined with the insolublen fraction suction filtered previously.

Yield: 20.7 g (64% of theory) MS: (M–H)⁻=281/283 (Cl)

(4b) methyl 2-acetylamino-3-(4-amino-3-chloro-5-methyl-phenyl)-propionate 20.6 g (73.0 mmol) methyl (E)-2-acetylamino-3-(4-amino-3-chloro-5-methyl-phenyl)-acrylate, 0.445 g (0.90 mmol) bis(1,5-cyclooctadiene)-di-rhodium(I)-dichloride, 0.744 g (1.8 mmol) 1,3-bis(diphenylphosphino)-propane were dissolved in 400 ml degassed methanol and 12 ml degassed triethylamine and then hydrogenated at ambient temperature under 3 bar hydrogen pressure. The reaction mixture was evaporated down under reduced pressure and taken up in ethyl acetate. The insoluble precipitate was removed by suction filtering and the filtrate was evaporated down under reduced pressure. The residue was purified by column chromatography.

Yield: 21.1 g (quantitative) MS: (M+H)⁺=285/287 (Cl)

(4c) methyl (R)-2-acetylamino-3-(4-amino-3-chloro-5-methyl-phenyl)-propionate 22 mL Alcalase 2.4 L FG (Novozymes ANS; DK 2880 Bagsvaerd) were added to a solution of 27.3 g (178 mmol) disodium hydrogen phosphate dihydrate in 1000 mL water at 37° C. and the pH was adjusted to 7.5 by the addition of sodium dihydrogen phosphate dihydrate. Then 21.1 g (74 mmol) methyl 2-acetylamino-3-(4-amino-3-chloro-5-methyl-phenyl)-propionate dissolved in 210 mL acetone was added dropwise with stirring at 37° C. The pH of the reaction mixture was kept constantly in the range from pH 7.4 to pH 7.6 by the addition of 1 M NaOH. After the addition had ended the mixture was stirred for 3 h at 37° C. The reaction mixture was combined with 500 ml 15% potassium carbonate solution and extracted twice with 250 ml dichloromethane. The combined organic extracts were dried over sodium sulphate, evaporated down under reduced pressure and purified by column chromatography over silica gel.

Yield: 2.57 g (12% of theory) ESI-MS: (M+H)⁺=285/287 (Cl)

(4d) ethyl (R)-2-amino-3-(4-amino-3-chloro-5-methyl-phenyl)-propionate

A mixture of 2.6 g (9.0 mmol) methyl (R)-2-acetylamino-3-(4-amino-3-chloro-5-methyl-phenyl)-propionate and 15 ml 4-molar hydrochloric acid solution was refluxed for 6 hours gekocht, the reaction mixture was evaporated down under reduced pressure and stirred for 3 days at ambient temperature with 15 ml of 12 molar ethanolic hydrochloric acid solution. The reaction mixture was evaporated to dryness, the residue was taken up with 50 ml of water and extracted with 50 ml of ethyl acetate. The aqueous phase was made alkaline by the addition of potassium carbonate and repeatedly extracted with ethyl acetate. The combined ethyl acetate extracts were dried over sodium sulphate and evaporated down under reduced pressure.

Yield: 2.09 g (90% of theory) ESI-MS: (M+H)⁺=257/259 (Cl)

(4e) ethyl (R)-3-(4-amino-3-chloro-5-methyl-phenyl)-2-{[4-(2-oxo-1,2,4,5-tetrahydro-benzo[d][1,3]diazepin-3-yl)-piperidine-1-carbonyl]-amino}-propionate An ice-cooled mixture of 2.09 g (8.1 mmol) ethyl (R)-2-amino-3-(4-amino-3-chloro-5-methyl-phenyl)-propionate and 100 ml DMF was combined with 1.6 g (9.7 mmol) CDT and stirred for 30 minutes while cooling with ice. Then while cooling with ice 2.0 g (8.1 mmol) 3-piperidin-4-yl-1,3,4,5-tetrahydro-benzo[d][1,3]diazepin-2-one, dissolved in 80 ml DMF, was added dropwise and the mixture was stirred for 12 hours at ambient temperature. The reaction mixture was poured onto 300 ml ice water, the precipitate was suction filtered and dried in the circulating air dryer at 30° C.

Yield: 4.1 g (95% of theory) ESI-MS: (M+H)⁺=528/530 (Cl)

(4f) (R)-3-(4-amino-3-chloro-5-methyl-phenyl)-2-{[4-(2-oxo-1,2,4,5-tetrahydro-benzo[d][1,3]diazepin-3-yl)-piperidine-1-carbonyl]-amino}-propionic acid The mixture of 4.1 g (7.8 mmol) ethyl (R)-3-(4-amino-3-chloro-5-methyl-phenyl)-2-{[4-(2-oxo-1,2,4,5-tetrahydro-benzo[d][1,3]diazepin-3-yl)-piperidine-1-carbonyl]-amino}-propionate, 60 ml of methanol and 60 ml THF was combined with a solution of 1.5 g (36.8 mmol) lithium hydroxide in 30 ml of water and stirred for 20 hours at 40° C. The reaction mixture was evaporated down under reduced pressure, the residue was taken up in 50 ml of water and acidified by the addition of 2-molar hydrochloric acid solution. The resulting precipitate was suction filtered and dried at 35° C. in the circulating air dryer.

Yield: 3.6 g (94% of theory) ESI-MS: $(M+H)^+$=500/502 (Cl)

(4g) 4-(2-oxo-1,2,4,5-tetrahydro-benzo[d][1,3]diazepin-3-yl)-piperidine-1-carboxylic acid-[(R)-1-(4-amino-3-chloro-5-methyl-benzyl)-2-(4-cyclopropyl-piperazin-1-yl)-2-oxo-ethyl]-amide 0.1 ml diisopropylethylamine, 64.2 mg (0.20 mmol) TBTU and 27.0 mg (0.20 mmol) HOBt was added to a mixture of 100 mg (0.20 mmol) (R)-3-(4-amino-3-chloro-5-methyl-phenyl)-2-([4-(2-oxo-1,2,4,5-tetrahydro-benzo[d][1,3]diazepin-3-yl)-piperidine-1-carbonyl]-amino)-propionic acid, 10 ml THF and 1 ml DMF, the mixture was stirred for 15 hours at ambient temperature and then combined with 80 mg (0.60 mmol) 1-cyclopropyl-piperazine. The reaction mixture was stirred for 3 hours at ambient temperature, combined with 20 ml semisaturated sodium hydrogen carbonate solution and extracted twice with 20 ml of ethyl acetate. The combined organic phases were washed once with 20 ml saturated saline solution, dried over sodium sulphate and evaporated down under reduced pressure. The residue was purified by column chromatography through silica gel.

Yield: 89.5 mg (74% of theory) ESI-MS: $(M+H)^+$=608/610 (Cl)

EXAMPLE 4.1

4-(2-oxo-1,2,4,5-tetrahydro-benzo[d][1,3]diazepin-3-yl)-piperidine-1-carboxylic acid-[(R)-1-(4-amino-3-chloro-5-methyl-benzyl)-2-(4-isopropyl-piperazin-1-yl)-2-oxo-ethyl]-amide

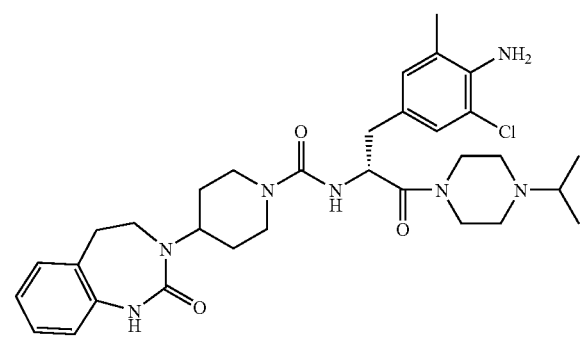

Prepared analogously to Example 4g.
Yield: 65% of theory) ESI-MS: $(M+H)^+$=610/612 (Cl)

EXAMPLE 5

4-(2-oxo-1,2,4,5-tetrahydro-benzo[d][1,3]diazepin-3-yl)-piperidine-1-carboxylic acid-{(R)-1-(4-amino-3-chloro-5-ethynyl-benzyl)-2-[4-(4-methyl-piperazin-1-yl)-piperidin-1-yl]-2-oxo-ethyl}-amide

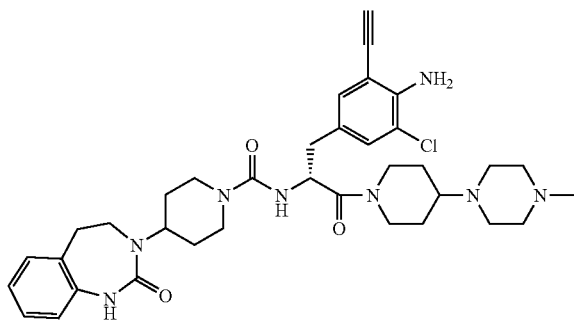

(5a) methyl (E)-2-acetylamino-3-(4-amino-3-chloro-phenyl)-acrylate

Prepared analogously to Example 4a.
Yield: 56% of theory MS: $(M+H)^+$=269/271 (Cl)

(5b) methyl 2-acetylamino-3-(4-amino-3-chloro-phenyl)-propionate

Prepared analogously to Example 4b.
Yield: 100% of theory (5c) methyl (R)-2-acetylamino-3-(4-amino-3-chloro-phenyl)-propionate Prepared analogously to Example 4c.
Yield: 39% of theory MS: $(M+H)^+$=271/273 (Cl)

(5d) ethyl (R)-2-amino-3-(4-amino-3-chloro-phenyl)-propionate

Prepared analogously to Example 4d.
Yield: 80% of theory MS: $(M+H)^+$=243/245 (Cl)

(5e) ethyl (R)-2-amino-3-(4-amino-3-chloro-5-iodo-phenyl)-propionate

A solution of 1.85 g (7.6 mmol) (R)-2-amino-3-(4-amino-3-chloro-phenyl)-propionate ethyl was added dropwise to a mixture of 1.95 g (7.7 mmol) iodine, 2.4 g (7.7 mmol) silver sulphate and 70 ml of ethanol. The reaction mixture was stirred for 4 days at ambient temperature, again combined with a solution of 195 mg (0.77 mmol) iodine and 240 mg (0.77 mmol) silver sulphate in 10 ml of ethanol and stirred for a further 3 days. The reaction mixture was filtered, the filtrate was evaporated down under reduced pressure, combined with 100 ml 15% potassium carbonate solution and extracted twice with 100 ml of ethyl acetate. The combined organic phases were dried over sodium sulphate, evaporated down and purified by chromatography over silica gel.

Yield: 1.5 g (54% of theory) MS: $(M+H)^+$=369/371 (Cl)

(5f) ethyl (R)-2-amino-3-(4-amino-3-chloro-5-trimethylsilanylethynyl-phenyl)-propionate Under protective argon gas a mixture of 235 mg (0.64 mmol) ethyl (R)-2-amino-3-(4-amino-3-chloro-5-iodo-phenyl)-propionate, 45.9 mg (0.064 mmol) bis-(triphenylphosphine)-palladium(II)-dichloride, 6.0 mg (0.032 mmol) copper(I)-iodide and 15 ml triethylamine was combined with 0.19 ml (1.32 mmol) trimethylsilylacetylene and stirred for 3 hours at ambient temperature. The reaction mixture was combined with 30 ml of water and extracted with 40 ml of ethyl acetate. The organic phase was dried over sodium sulphate, evaporated down under reduced pressure and the residue was purified by column chromatography through silica gel.

Yield: 168 mg (78% of theory) MS: $(M+H)^+ = 339/341$ (Cl)

(5g) ethyl (R)-3-(4-amino-3-chloro-5-trimethylsilanylethynyl-phenyl)-2-{[4-(2-oxo-1,2,4,5-tetrahydro-benzo[d][1,3]diazepin-3-yl)-piperidine-1-carbonyl]-amino}-propionate Prepared analogously to Example 4e.
Yield: 89% of theory ESI-MS: $(M+H)^+ = 610/612$ (Cl)

(5h) (R)-3-(4-amino-3-chloro-5-ethynyl-phenyl)-2-{[4-(2-oxo-1,2,4,5-tetrahydro-benzo[d][1,3]diazepin-3-yl)-piperidine-1-carbonyl]-amino}-propionic acid Prepared analogously to Example 4f.
Yield: 91% of theory ESI-MS: $(M+H)^+ = 510/512$ (Cl)

(5i) 4-(2-oxo-1,2,4,5-tetrahydro-benzo[d][1,3]diazepin-3-yl)-piperidine-1-carboxylic acid-{(R)-1-(4-amino-3-chloro-5-ethynyl-benzyl)-2-[4-(4-methyl-piperazin-1-yl)-piperidin-1-yl]-2-oxo-ethyl}-amide Prepared analogously to Example 4g.
Yield: 75% of theory ESI-MS: $(M+H)^+ = 675/677$ (Cl) retention time (HPLC): 5.4 min (method A)

EXAMPLE 6

4-(2-oxo-1,2,4,5-tetrahydro-benzo[d][1,3]diazepin-3-yl)-piperidine-1-carboxylic acid-{(R)-1-(4-amino-3-chloro-5-ethyl-benzyl)-2-[4-(4-methyl-piperazin-1-yl)-piperidin-1-yl]-2-oxo-ethyl}-amide

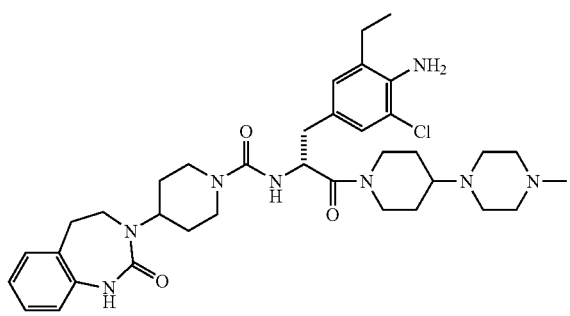

54 mg (73.0 mmol) 4-(2-oxo-1,2,4,5-tetrahydro-benzo[d][1,3]diazepin-3-yl)-piperidine-1-carboxylic acid-{(R)-1-(4-amino-3-chloro-5-ethynyl-benzyl)-2-[4-(4-methyl-piperazin-1-yl)-piperidin-1-yl]-2-oxo-ethyl}-amide, 10 mg (0.02 mmol) of bis(1,5-cyclooctadiene)-di-rhodium(I)-dichloride, 16.5 mg (0.04 mmol) 1,3-bis(diphenylphosphino)-propane were dissolved in 10 ml degassed methanol and 0.1 ml degassed triethylamine and then hydrogenated for 2 hours at ambient temperature and 3 bar hydrogen pressure. The reaction mixture was evaporated down under reduced pressure and taken up in ethyl acetate. The insoluble precipitate was removed by suction filtering and the filtrate was evaporated down under reduced pressure. The residue was purified by column chromatography.

Yield: 23.3 mg (43% of theory) MS: $(M+H)^+ = 679/681$ (Cl) retention time (HPLC): 5.4 min (method A)

EXAMPLE 7

(S)-2-(4-amino-3-chloro-5-trifluoromethyl-benzyl)-1-[4-(4-cyclopropyl-piperazin-1-yl)-piperidin-1-yl]-4-[4-(2-oxo-1,2,4,5-tetrahydro-benzo[d][1,3]diazepin-3-yl)-piperidin-1-yl]-butane-1,4-dione

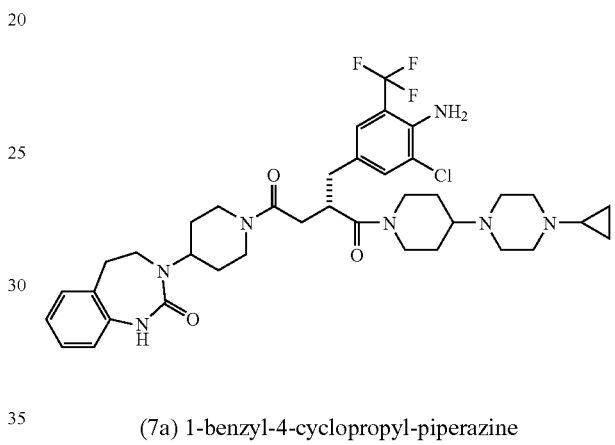

(7a) 1-benzyl-4-cyclopropyl-piperazine

A mixture of 1.946 ml (10.5 mmol) benzylpiperidone, 3.0 g (10.4 mmol) 1-cyclopropyl-piperazine and 300 ml DCM, stirred and cooled in the ice bath, was combined batchwise with 5.58 g (25.0 mmol) sodiumacetoxyborohydride and stirred overnight at RT. The reaction mixture was then combined with 60 ml 1-molar sodium hydroxide solution, the organic phase was separated off and evaporated down under reduced pressure. The residue was purified by column chromatography through Alox (eluant: petroleum ether/ethyl acetate=4/1).

Yield: 1.50 g (48% of theory) MS: $(M)^+ = 300 R_f: 0.75$ (PE/EtOAc=1/1)

(7b) 1-cyclopropyl-4-piperidin-4-yl-piperazine 1.5 g (5.0 mmol) 1-benzyl-4-cyclopropyl-piperazine in 50 ml of methanol was hydrogenated for 7 hours at RT under 5 bars pressure with the addition of 250 mg palladium on charcoal (10%). The catalyst was filtered off, the mother liquor was evaporated down under reduced pressure.

Yield: 1.05 g (100% of theory) MS: $(M)^+ = 210$

(7c) (S)-2-(4-amino-3-chloro-5-trifluoromethyl-benzyl)-1-[4-(4-cyclopropyl-piperazin-1-yl)-piperidin-1-yl]-4-[4-(2-oxo-1,2,4,5-tetrahydro-benzo[d][1,3]diazepin-3-yl)-piperidin-1-yl]-butane-1,4-dione A mixture of 499 mg (0.90 mmol) (S)-2-(4-amino-3-chloro-5-trifluoromethyl-benzyl)-4-oxo-4-[4-(2-oxo-1,2,4,5-tetrahydro-benzo[d][1,3]diazepin-3-yl)-piperidin-1-yl]-butanoic acid, 199 mg (0.95 mmol) 1-cyclopropyl-4- piperidin-4-yl-piperazine, 321 mg (1.00 mmol) TBTU, 0.277 ml triethylamine and 100 ml THF was stirred overnight at ambient temperature. The reaction mixture was evaporated down under reduced pressure and the residue was distributed between 150 ml of ethyl acetate and 150 ml 15% potassium carbonate solution. The organic phase was separated off, dried and evaporated down under reduced pressure. The residue was purified by column chromatography through silica gel.

Yield: 360.0 mg (54% of theory) MS: (M+H)⁺=744/746 (Cl) $R_f$: 0.55 (DCM/MeOH/aqu. ammonia=90/10/1)

EXAMPLE 8

(S)-2-(4-amino-3-chloro-5-trifluoromethyl-benzyl)-1-[4-(cyclopropyl-methyl-amino)-piperidin-1-yl]-4-[4-(2-oxo-1,2,4,5-tetrahydro-benzo[d][1,3]diazepin-3-yl)-piperidin-1-yl]-butan-1,4-dione

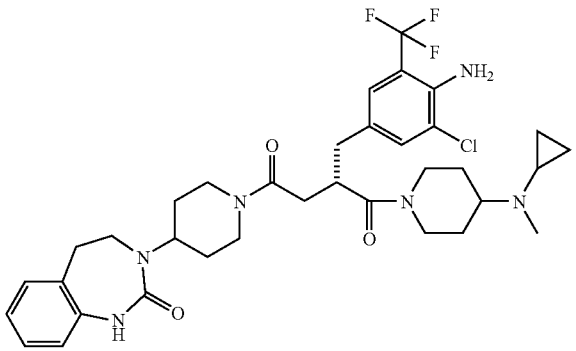

A mixture of 500 mg (0.90 mmol) (S)-2-(4-amino-3-chloro-5-trifluoromethyl-benzyl)-4-oxo-4-[4-(2-oxo-1,2,4,5-tetrahydro-benzo[d][1,3]diazepin-3-yl)-piperidin-1-yl]-butanoic acid, 207 mg (0.91 mmol) cyclopropyl-methyl-piperidin-4-yl-amine dihydrochloride, 385 mg (1.20 mmol) TBTU, 0,695 ml triethylamine, 50 ml DMF and 50 ml THF was stirred overnight at ambient temperature. The reaction mixture was freed from THF under reduced pressure and stirred into 200 ml of 15% potassium carbonate solution. The resulting solid precipitate was suction filtered, dried and then purified by column chromatography through silica gel.

Yield: 450.0 mg (72% of theory) MS: (M+H)⁺=689/691 (Cl) $R_f$: 0.55 (DCM/MeOH/aqu. ammonia=85/15/1.5)

EXAMPLE 9

(S)-2-(3-chloro-4-hydroxy-5-trifluoromethyl-benzyl)-1-(4-morpholin-4-yl-piperidin-1-yl)-4-[4-(2-oxo-1,2,4,5-tetrahydro-benzo[d][1,3]diazepin-3-yl)-piperidin-1-yl]-butane-1,4-dione

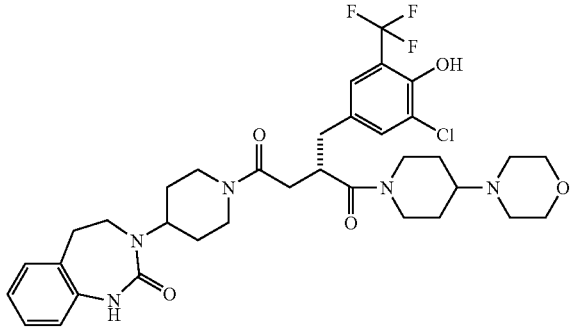

(9a) 4-hydroxy-3-trifluoromethyl-benzoic Acid

A mixture of 10.0 g (45.4 mmol) 4-methoxy-3-trifluoromethyl-benzoic acid and 75 g (649 mmol) pyridine hydrochloride was stirred for 5 hours at 180° C. under nitrogen gas. The reaction mixture was then poured onto 1 L of 10% citric acid solution, extracted with 500 ml EtOAc, the organic phase washed with 1 L water, dried and evaporated down under reduced pressure.

Yield: 11.7 g crude product ESI-MS: (M+H)⁻=205 retention time HPLC: 6.1 min (method A)

(9b) 3-chloro-4-hydroxy-5-trifluoromethyl-benzoic Acid

A mixture of 11.7 g (57 mmol) 4-hydroxy-3-trifluoromethyl-benzoic acid and 40 ml acetic acid was combined dropwise with 5.15 ml (63 mmol) sulphurylchloride, with stirring at a bath temperature of 40° C., and stirred for 2 hours at 40° C. Then another 2.5 ml (31 mmol) sulphurylchloride were added and the mixture was stirred for 4 hours at 60° C. The reaction mixture was poured onto 300 ml of water and extracted with 200 ml EtOAc. The organic phase washed twice with 500 ml of water, dried and evaporated down under reduced pressure. The residue was stirred with 80 ml petroleum ether, the precipitate was suction filtered, washed with 20 ml petroleum ether and dried.

Yield: 7.7 g (56% of theory) ESI-MS: (M+H)⁺=239/241 (Cl) retention time HPLC: 6.5 min (method A)

(9c) 2-chloro-4-hydroxymethyl-6-trifluoromethyl-phenol 7.7 g (32 mmol) 3-chloro-4-hydroxy-5-trifluoromethyl-benzoic acid dissolved in 100 ml THF were combined with 5.76 g (36 mmol) carbonyldiimidazole and stirred for 1 hour at 40° C. Then the mixture was cooled to ambient temperature and slowly added under a nitrogen atmosphere to a stirred solution of 3.78 g (100 mmol) sodium borohydride in 40 ml of water and stirred for a further 2 hours at ambient temperature. The reaction mixture was diluted with 200 ml of water, acidified with 50 ml semiconcentrated hydrochloric acid and extracted twice with EtOAc. The combined organic phases were dried over sodium sulphate, filtered and evaporated down under reduced pressure.

Yield: 5.9 g (81% of theory) ESI-MS: (M+H)⁺=225/227 (Cl) $R_f$: 0.85 (EtOAc)

(9d) 3-chloro-4-hydroxy-5-trifluoromethyl-benzaldehyde 30.0 g (345 mmol) manganese dioxide was added batchwise, with stirring, to a mixture of 5.90 g (26 mmol) 2-chloro-4-hydroxymethyl-6-trifluoromethyl-phenol and 100 ml dichloromethane and stirred for 2 hours at ambient temperature. The reaction mixture was suction filtered to remove the solid, the solution was evaporated down under reduced pressure and further reacted as the crude product.

(9e) 1-methyl 2-[1-(3-chloro-4-hydroxy-5-trifluoromethyl-phenyl)-meth-(Z)-ylidene]-succinate A mixture of 3.0 g (14.4 mmol) 3-chloro-4-hydroxy-5-trifluoromethyl-benzaldehyde and 100 ml THF was combined with 10.48 g (26.7 mmol) monomethyl 3-(triphenyl-λ5-phosphanylidene)-dipentanoate and stirred for 6 days at 42° C. The reaction mixture was evaporated down under reduced pressure, the residue was taken up in water and EtOAc. The organic phase was separated off, washed with water and extracted three times with 15% potassium carbonate solution. The combined aqueous extracts were washed with EtOAc, combined with 200 ml EtOAc and acidified with stirring by the addition of conc. hydrochloric acid. The organic phase was separated off, dried over sodium sulphate, filtered and evaporated down under reduced pressure. The residue was purified by column chromatography through silica gel (eluant: PE/EtOAc=1/1).

Yield: 2.5 g (55% of theory) ESI-MS: $(M+H)^+=337/339$ (Cl) $R_f$: 0.75 (EtOAc)

(9f) 1-methyl (S)-2-(3-chloro-4-hydroxy-5-trifluoromethyl-benzyl)-succinate 2.3 g (6.7 mmol) 1-methyl 2-[1-(3-chloro-4-hydroxy-5-trifluoromethyl-phenyl)-meth-(Z)-ylidene]-succinate was dissolved in a degassed solution of 30 ml of methanol and 2.5 ml triethylamine and combined with 100 mg (−)-1,2-bis-((2R,5R)-2,5-diethyl-phospholano)benzene-(cyclooctadiene)-rhodium-(I) tetrafluoroborate. The reaction solution was hydrogenated for 8 hours at RT under 50 bar hydrogen. The reaction mixture was evaporated down under reduced pressure, the residue was dissolved in 100 ml EtOAc and washed twice with 70 ml of 2-molar hydrochloric acid. The organic phase was then extracted three times with 15% potassium carbonate solution, the combined aqueous phases were acidified with conc. hydrochloric acid and extracted twice with EtOAc. The combined organic phases were dried over sodium sulphate, filtered and evaporated down under reduced pressure.

Yield: 1.7 g (74% of theory) ESI-MS: $(M+H)^+=341/343$ (Cl) retention time HPLC: 7.1 min (method A)

(9g) methyl (S)-2-(3-chloro-4-hydroxy-5-trifluoromethyl-benzyl)-4-oxo-4-[4-(2-oxo-1,2,4,5-tetrahydro-benzo[d][1,3]diazepin-3-yl)-piperidin-1-yl]-butanoate A mixture of 1.19 g (4.9 mmol) 1-methyl (S)-2-(3-chloro-4-hydroxy-5-trifluoromethyl-benzyl)-succinate, 1.56 g (4.9 mmol) TBTU, 0.73 ml (5.0 mmol) triethylamine, 1.65 g (4.8 mmol) 3-piperidin-4-yl-1,3,4,5-tetrahydro-benzo[d][1,3]diazepin-2-one and 30 ml DMF was stirred for 12 hours at RT. The reaction mixture was evaporated down under reduced pressure, the residue was taken up in 200 ml EtOAc and washed with 200 ml 10% citric acid solution and 50 ml saturated aqueous sodium hydrogen carbonate solution. The organic phase was dried and evaporated down under reduced pressure.

Yield: 1.8 g (65% of theory) ESI-MS: $(M+H)^+=568/570$ (Cl) retention time HPLC: 8.1 min (method A)

(9h) (S)-2-(3-chloro-4-hydroxy-5-trifluoromethyl-benzyl)-4-oxo-4-[4-(2-oxo-1,2,4,5-tetrahydro-benzo[d][1,3]diazepin-3-yl)-piperidin-1-yl]-butanoic Acid 1.8 g methyl (S)-2-(3-chloro-4-hydroxy-5-trifluoromethyl-benzyl)-4-oxo-4-[4-(2-oxo-1,2,4,5-tetrahydro-benzo[d][1,3]diazepin-3-yl)-piperidin-1-yl]-butanoate dissolved in 50 ml THF was combined with a solution of 115.2 mg (4.8 mmol) lithium hydroxide in 50 ml of water and stirred overnight at RT. The reaction mixture was evaporated down under reduced pressure, combined with 150 ml of water and washed with 150 ml EtOAc. The aqueous phase was acidified with conc. hydrochloric acid and extracted with 150 ml EtOAc. The organic phase was separated off, dried and evaporated down under reduced pressure.

Yield: 1.5 g (85% of theory) ESI-MS: $(M+H)^+=554/556$ (Cl) retention time HPLC: 7.2 min (method A)

(9i) (S)-2-(3-chloro-4-hydroxy-5-trifluoromethyl-benzyl)-1-(4-morpholin-4-yl-piperidin-1-yl)-4-[4-(2-oxo-1,2,4,5-tetrahydro-benzo[d][1,3]diazepin-3-yl)-piperidin-1-yl]-butan-1,4-dione Prepared analogously to Example (1 g) from 70 mg (0.126 mmol) (S)-2-(3-chloro-4-hydroxy-5-trifluoromethyl-benzyl)-4-oxo-4-[4-(2-oxo-1,2,4,5-tetrahydro-benzo[d][1,3]diazepin-3-yl)-piperidin-1-yl]-butanoic acid and 22 mg (0.130 mmol) 4-piperidin-4-yl-morpholine.

Yield: 47 mg (53% of theory) ESI-MS: $(M+H)^+=706/708$ (Cl) retention time HPLC: 6.0 min (method A)

The following Examples describe the preparation of pharmaceutical formulations which contain as active substance any desired compound of general formula (I):

EXAMPLE I

Capsules for Powder Inhalation Containing 1 mg of Active Ingredient

Composition:

1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

EXAMPLE II

Inhalable Solution for Respimat® Containing 1 mg of Active Ingredient

Composition:

1 puff contains:

| | |
|---|---|
| active ingredient | 1.0 mg |
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

EXAMPLE III

Inhalable Solution for Nebulisers Containing 1 mg of Active Ingredient

Composition:

1 vial contains:

| active ingredient | 0.1 g |
|---|---|
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

EXAMPLE IV

Propellant Gas-Operated Metering Aerosol Containing 1 mg of Active Ingredient

Composition:

1 puff contains:

| active ingredient | 1.0 mg |
|---|---|
| lecithin | 0.1% |
| propellant gas ad | 50.0 μl |

Method of Preparation:

The micronised active ingredient is homogeneously suspended in the mixture of lecithin and propellant gas. The suspension is transferred into a pressurised container with a metering valve.

EXAMPLE V

Nasal Spray Containing 1 mg of Active Ingredient

Composition:

| active ingredient | 1.0 mg |
|---|---|
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

EXAMPLE VI

Injectable Solution Containing 5 mg of Active Substance Per 5 ml

Composition:

| active substance | 5 mg |
|---|---|
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

EXAMPLE VII

Injectable Solution Containing 100 mg of Active Substance Per 20 ml

Composition:

| active substance | 100 mg |
|---|---|
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

EXAMPLE VIII

Lyophilisate Containing 10 mg of Active Substance

Composition:

| Active substance | 10 mg |
|---|---|
| Mannitol | 300 mg |
| human serum albumin | 20 mg |

Preparation:

Mannitol is dissolved in water for injections (WfI); human serum albumin is added; active ingredient is dissolved with heating; made up to specified volume with WfI; transferred into vials; freeze-dried.

Solvent for Lyophilisate:

| Polysorbate 80 = Tween 80 | 20 mg |
|---|---|
| mannitol | 200 mg |
| water for injections ad | 10 ml |

Preparation:
Polysorbate 80 and mannitol are dissolved in water for injections (WfI); transferred into ampoules.

EXAMPLE IX

Tablets Containing 20 mg of Active Substance

Composition:

| active substance | 20 mg |
|---|---|
| lactose | 120 mg |
| maize starch | 40 mg |
| magnesium stearate | 2 mg |
| Povidone K 25 | 18 mg |

Preparation:
Active substance, lactose and maize starch are homogeneously mixed; granulated with an aqueous solution of Povidone; mixed with magnesium stearate; compressed in a tablet press; weight of tablet 200 mg.

EXAMPLE X

Capsules Containing 20 mg Active Substance

Composition:

| active substance | 20 mg |
|---|---|
| maize starch | 80 mg |
| highly dispersed silica | 5 mg |
| magnesium stearate | 2.5 mg |

Preparation:
Active substance, maize starch and silica are homogeneously mixed; mixed with magnesium stearate; the mixture is packed into size for 3 hard gelatine capsules in a capsule filling machine.

EXAMPLE XI

Suppositories Containing 50 mg of Active Substance

Composition:

| active substance | 50 mg |
|---|---|
| hard fat (Adeps solidus) q.s. ad | 1700 mg |

Preparation:
Hard fat is melted at about 38° C.; ground active substance is homogeneously dispersed in the molten hard fat; after cooling to about 35° C. it is poured into chilled moulds.

EXAMPLE XII

Injectable Solution Containing 10 mg of Active Substance Per 1 ml

Composition:

| active substance | 10 mg |
|---|---|
| mannitol | 50 mg |
| human serum albumin | 10 mg |
| water for injections ad | 1 ml |

Preparation:
Mannitol is dissolved in water for injections (WfI); human serum albumin is added; active ingredient is dissolved with heating; made up to specified volume with WfI; transferred into ampoules under nitrogen gas.

What is claimed is:
1. A compound selected from the group consisting of:
   (1) (R)-1-(4-amino-3-chloro-5-trifluoromethyl-benzyl)-2-oxo-2-[4-(2-piperidin-1-yl-ethyl)-piperidin-1-yl]-ethyl 4-(2-oxo-1,2,4,5-tetrahydro-benzo[d][1,3]diazepin-3-yl)-piperidine-1-carboxylate,
   (2) (R)-1-(4-amino-3-chloro-5-trifluoromethyl-benzyl)-2-[4-(1-aza-bicyclo-[2.2.2]oct-3-yl)-piperazin-1-yl]-2-oxo-ethyl 4-(2-oxo-1,2,4,5-tetrahydro-benzo [d][1,3]diazepin-3-yl)-piperidine-1-carboxylate,
   (3) (R)-1-(4-amino-3-chloro-5-trifluoromethyl-benzyl)-2-[4-(5-methyl-2,5-diaza-bicyclo[2.2.1]hept-2-yl)-piperidin-1-yl]-2-oxo-ethyl 4-(2-oxo-1,2,4,5-tetrahydro-benzo[d][1,3]diazepin-3-yl)-piperidine-1-carboxylate,
   (4) (R)-2-(4-amino-3-chloro-5-trifluoromethyl-phenyl)-1-(5-dimethylamino-pentylcarbamoyl)-ethyl 4-(2-oxo-1,2,4,5-tetrahydro-benzo[d][1,3]diazepin-3-yl)-piperidine-1-carboxylate,
   (5) (R)-1-(4-amino-3-chloro-5-trifluoromethyl-benzyl)-2-oxo-2-[4-((3R,5S)-3,4,5-trimethyl-piperazin-1-yl)-piperidin-1-yl]-ethyl 4-(2-oxo-1,2,4,5-tetrahydro-benzo[d][1,3]diazepin-3-yl)-piperidine-1-carboxylate,
   (6) (R)-1-(4-amino-3-chloro-5-trifluoromethyl-benzyl)-2-oxo-2-[4-(3,3,4,5,5-pentamethyl-piperazin-1-yl)-piperidin-1-yl]-ethyl 4-(2-oxo-1,2,4,5-tetrahydro-benzo[d][1,3]diazepin-3-yl)-piperidine-1-carboxylate,
   (7) (R)-1-(4-amino-3-chloro-5-trifluoromethyl-benzyl)-2-[4-(4-cyclopropyl-piperazin-1-yl)-piperidin-1-yl]-2-oxo-ethyl 4-(2-oxo-1,2,4,5-tetrahydro-benzo[d][1,3]diazepin-3-yl)-piperidine-1-carboxylate,
   (8) (R)-1-(4-amino-3-chloro-5-trifluoromethyl-benzyl)-2-[4-(1-methyl-piperidin-4-yl)-[1,4]diazepan-1-yl]-2-oxo-ethyl 4-(2-oxo-1,2,4,5-tetrahydro-benzo[d][1,3]diazepin-3-yl)-piperidine-1-carboxylate,
   (9) (R)-1-(4-amino-3-chloro-5-trifluoromethyl-benzyl)-2-(7-dimethylaminomethyl-1,2,4,5-tetrahydro-benzo[d]azepin-3-yl)-2-oxo-ethyl 4-(2-oxo-1,2,4,5-tetrahydro-benzo[d][1,3]diazepin-3-yl)-piperidine-1-carboxylate,
   (10) (R)-1-(4-amino-3-chloro-5-trifluoromethyl-benzyl)-2-[4-(cyclopropyl-methyl-amino)-piperidin-1-yl]-2-oxo-ethyl 4-(2-oxo-1,2,4,5-tetrahydro-benzo[d][1,3]diazepin-3-yl)-piperidine-1-carboxylate,
   (11) (R)-1-(4-amino-3-chloro-5-trifluoromethyl-benzyl)-2-[4-(hexahydro-pyrrolo-[1,2-a]pyrazin-2-yl)-piperidin-1-yl]-2-oxo-ethyl 4-(2-oxo-1,2,4,5-tetrahydro-benzo[d][1,3]diazepin-3-yl)-piperidine-1-carboxylate,
   (12) (R)-1-(4-amino-3-chloro-5-trifluoromethyl-benzyl)-2-[4-(1-ethyl-piperidin-4-yl)-piperazin-1-yl]-2-oxo- ethyl 4-(2-oxo-1,2,4,5-tetrahydro-benzo[d][1,3]diazepin-3-yl)-piperidine-1-carboxylate,
(13) (R)-1-(4-amino-3-chloro-5-trifluoromethyl-benzyl)-2-[4-(8-methyl-8-aza-bicyclo[3.2.1]oct-3-yl)-piperazin-1-yl]-2-oxo-ethyl 4-(2-oxo-1,2,4,5-tetrahydro-benzo[d][1,3]diazepin-3-yl)-piperidine-1-carboxylate,
(14) (R)-1-(4-amino-3-chloro-5-trifluoromethyl-benzyl)-2-[4-(4-methyl-[1,4]di-azepan-1-yl)-piperidin-1-yl]-2-oxo-ethyl 4-(2-oxo-1,2,4,5-tetrahydro-benzo[d][1,3]diazepin-3-yl)-piperidine-1-carboxylate,
(15) (R)-1-(4-amino-3-chloro-5-trifluoromethyl-benzyl)-2-(4-cyclopropylmethyl-piperazin-1-yl)-2-oxo-ethyl 4-(2-oxo-1,2,4,5-tetrahydro-benzo[d][1,3]diazepin-3-yl)-piperidine-1-carboxylate,
(16) (R)-1-(4-amino-3-chloro-5-trifluoromethyl-benzyl)-2-(4-azepan-1-yl-piperidin-1-yl)-2-oxo-ethyl 4-(2-oxo-1,2,4,5-tetrahydro-benzo[d][1,3]diazepin-3-yl)-piperidine-1-carboxylate,
(17) (R)-1-(4-amino-3-chloro-5-trifluoromethyl-benzyl)-2-(4-morpholin-4-yl-piperidin-1-yl)-2-oxo-ethyl 4-(2-oxo-1,2,4,5-tetrahydro-benzo[d][1,3]diazepin-3-yl)-piperidine-1-carboxylate,
(18) (R)-1-(4-amino-3-chloro-5-trifluoromethyl-benzyl)-2-(4-imidazol-1-yl-piperidin-1-yl)-2-oxo-ethyl 4-(2-oxo-1,2,4,5-tetrahydro-benzo[d][1,3]diazepin-3-yl)-piperidine-1-carboxylate,
(19) (R)-1-(4-chloro-3-trifluoromethyl-benzyl)-2-[4-(4-methyl-piperazin-1-yl)-piperidin-1-yl]-2-oxo-ethyl 4-(2-oxo-1,2,4,5-tetrahydro-benzo[d][1,3]diazepin-3-yl)-piperidine-1-carboxylate, and
(20) (R)-1-(4-chloro-3-trifluoromethyl-benzyl)-2-[4-(1-methyl-piperidin-4-yl)-piperazin-1-yl]-2-oxo-ethyl 4-(2-oxo-1,2,4,5-tetrahydro-benzo[d][1,3]diazepin-3-yl)-piperidine-1-carboxylate,
or a tautomer or salt thereof.

2. A physiologically acceptable salt of a compound according to claim 1.

3. A pharmaceutical composition containing a compound according to claim 1 or a physiologically acceptable salt thereof, together with one or more inert carriers and/or diluents.

4. A method for treating migraine or cluster headaches which comprises administering to a host in need of such treatment a therapeutically effective amount of a compound according to claim 1 or a physiologically acceptable salt thereof.

5. A method for treating non-insulin-dependent diabetes mellitus (NIDDM) which comprises administering to a host in need of such treatment a therapeutically effective amount of a compound according to claim 1 or a physiologically acceptable salt thereof.

* * * * *